(12) United States Patent
Dabrowiak et al.

(10) Patent No.: US 11,865,035 B2
(45) Date of Patent: Jan. 9, 2024

(54) TRANSPORT BATTERY FOR USE WITH PORTABLE THERMAL MANAGEMENT SYSTEM

(71) Applicant: Zoll Circulation, Inc., San Jose, CA (US)

(72) Inventors: Jeremy Thomas Dabrowiak, Santa Clara, CA (US); Richard Allen Smith, Campbell, CA (US); Christo Petrov Pamichev, Cupertino, CA (US); David R. Deam, San Ramon, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 545 days.

(21) Appl. No.: 16/835,232

(22) Filed: Mar. 30, 2020

(65) Prior Publication Data
US 2020/0330263 A1 Oct. 22, 2020

Related U.S. Application Data

(60) Provisional application No. 62/832,875, filed on Apr. 11, 2019, provisional application No. 62/832,785, (Continued)

(51) Int. Cl.
*F25B 49/02* (2006.01)
*A61F 7/00* (2006.01)
(Continued)

(52) U.S. Cl.
CPC .......... *A61F 7/0085* (2013.01); *F25B 49/022* (2013.01); *H02J 7/0013* (2013.01);
(Continued)

(58) Field of Classification Search
CPC ............ A61F 7/0085; A61F 2007/0078; A61F 2007/0096; A61F 2007/126; F25B 49/022;
(Continued)

(56) References Cited

U.S. PATENT DOCUMENTS 9,099,877 B2   8/2015  Deam
9,492,633 B2  11/2016  Dabrowiak
(Continued)

OTHER PUBLICATIONS

CN 107101411 (English translation) (Year: 2017).*

*Primary Examiner* — Jonathan Bradford
(74) *Attorney, Agent, or Firm* — ZOLL Circulation, Inc.

(57) ABSTRACT

A portable system for managing the temperature of a patient during transport includes a heater/cooler configured to be in fluid communication with a heat transfer catheter or a heat transfer surface pad; a pump for circulating heat exchange fluid; an alternating current power supply; and a processor configured to indicate if the alternating current power supply connection to the source of alternating current is interrupted.

(Continued)

A rechargeable battery may be configured to provide power to the system when the alternating power supply is not connected to a source of alternating current. If the system is powered on and the connection to the alternating current source is interrupted, the system may automatically switch to receiving power from the rechargeable battery. The processor may alert an operator of the interruption of the connection to the alternating current source and indicate to the operator the amount of energy remaining in the battery.

19 Claims, 32 Drawing Sheets

Related U.S. Application Data filed on Apr. 11, 2019, provisional application No. 62/826,958, filed on Mar. 29, 2019.

(51) Int. Cl.
  *H02J 7/00* (2006.01)
  *H02J 9/06* (2006.01)
  *A61F 7/12* (2006.01)

(52) U.S. Cl.
  CPC ............ *H02J 7/0042* (2013.01); *H02J 9/06* (2013.01); *A61F 2007/0078* (2013.01); *A61F 2007/0096* (2013.01); *A61F 2007/126* (2013.01); *F25B 2600/025* (2013.01); *F25B 2600/0251* (2013.01); *F25B 2700/151* (2013.01); *F25B 2700/2103* (2013.01); *H02J 2310/23* (2020.01)

(58) Field of Classification Search
  CPC ........ F25B 2600/025; F25B 2600/0251; F25B 2700/151; F25B 2700/2103; H02J 7/0013; H02J 7/0042; H02J 9/06
  See application file for complete search history.

(56) References Cited

U.S. PATENT DOCUMENTS

| | | | |
|---|---|---|---|
| 2002/0019654 A1* | 2/2002 | Ellis | A61F 7/007 607/98 |
| 2010/0162741 A1* | 7/2010 | Friday, Jr. | F25B 25/005 700/282 |
| 2011/0133551 A1* | 6/2011 | Moller | H04L 12/10 307/11 |
| 2013/0079855 A1 | 3/2013 | Helkowski | |
| 2013/0079856 A1 | 3/2013 | Dabrowiak | |
| 2013/0090708 A1 | 4/2013 | Dabrowiak | |
| 2013/0178923 A1 | 7/2013 | Dabrowiak | |
| 2014/0094880 A1 | 4/2014 | Lim | |
| 2014/0094882 A1 | 4/2014 | Lim | |
| 2014/0094883 A1 | 4/2014 | Lim | |
| 2014/0172158 A1* | 6/2014 | Paradissis | F25D 29/00 700/232 |
| 2014/0216098 A1* | 8/2014 | Heinrich | F25D 29/003 62/448 |
| 2017/0209304 A1* | 7/2017 | Zumbrunnen | A61F 7/0085 |
| 2018/0001746 A1* | 1/2018 | Vehr | B60H 1/3205 |
| 2018/0185192 A1 | 7/2018 | Mazzone | |
| 2018/0185193 A1 | 7/2018 | Mazzone | |
| 2018/0207024 A1 | 7/2018 | Dabrowiak | |
| 2018/0214303 A1 | 8/2018 | Dabrowiak | |
| 2018/0325725 A1 | 11/2018 | Dabrowiak | |
| 2019/0133820 A1 | 5/2019 | Jacobsen | |

* cited by examiner

TRANSPORT BATTERY FOR USE WITH PORTABLE THERMAL MANAGEMENT SYSTEM

CLAIM OF PRIORITY

This application claims priority under 35 U.S.C. § 119(e) to U.S. Provisional Application Ser. No. 62/826,958, filed on Mar. 29, 2019, U.S. Provisional Application Ser. No. 62/832,785, filed on Apr. 11, 2019, and U.S. Provisional Application Ser. No. 62/832,875, filed on Apr. 11, 2019, the entire contents of each of which are hereby incorporated by reference.

TECHNICAL FIELD

The present disclosure relates generally to the fields of medicine and engineering, and more particularly to devices, systems and methods for controlling a patient's body temperature by endovascular or surface heating, and also to portable battery systems designed to power the devices when they are not being powered by alternating current.

BACKGROUND

In various clinical situations, it is desirable to warm, cool or otherwise control the body temperature of a subject. For example, hypothermia can be induced in humans and some animals for the purpose of protecting various organs and tissues (e.g., heart, brain, kidneys) against the effects of ischemic, anoxic or toxic insult. For example, animal studies and/or clinical trials suggest that mild hypothermia can have neuroprotective and/or cardioprotective effects in animals or humans who suffer from ischemic cardiac events (e.g., myocardial infract, acute coronary syndromes, etc.), post-anoxic coma after cardiopulmonary resuscitation, traumatic brain injury, stroke, subarachnoid hemorrhage, fever and neurological injury. Whole body hypothermia can ameliorate the toxic effects of radiographic contrast media on the kidneys (e.g., radiocontrast nephropathy) of patients with pre-existing renal impairment who undergo angiography procedures.

One method for inducing hypothermia is by intravascular temperature management (IVTM) wherein a heat exchange catheter is inserted into a blood vessel and a thermal exchange fluid is circulated through a heat exchanger positioned on the portion of the catheter that is inserted in the blood vessel. As the thermal exchange fluid circulates through the catheter's heat exchanger, it exchanges heat with blood flowing past the heat exchange in the blood vessel. Such technique can be used to cool the subject's flowing blood thereby resulting in a lowering of the subject's core body temperature to some desired target temperature. IVTM is also capable of warming the body and/or of controlling body temperature to maintain a monitored body temperature at some selected temperature. If a controlled rate of re-warming or re-cooling from the selected target temperature is desired, that too can be accomplished by carefully controlling the amount of heat added or removed from the body and thereby controlling the temperature change of the patient.

It is believed that the sooner a patient is cooled after ischemic insult, the better the therapy outcome. In many cases, thermal treatment should begin when the patient is placed into an ambulance. Moreover, once thermal treatment has begun, the thermal treatment should be continued when the patient is moved to another location of a care institution, such as, for example, when a patient arrives in an emergency room, and then needs to be transported from the emergency room to a catheterization laboratory, or when the patient is moved from one location to an intensive care unit, or when the patient is moved from one room to another.

SUMMARY

In accordance with the present disclosure, there is provided a heat exchange system for warming or cooling the body of a human or animal subject, such system comprising an extracorporeal control system that is connectable to one or more changeable component(s) such as, for example, an endovascular heat exchange catheter, a body surface heat exchange pad, tubing, a cassette through which thermal exchange fluid circulates, other disposable components, and the like. When the changeable component(s) is/are connected to the extracorporeal control system, the system is useable to effect heat exchange with the subject's body.

In another aspect, the changeable component(s) may include machine-readable encoded information. The extracorporeal control system includes a reader that receives and reads the encoded information. The extracorporeal control system uses such encoded information to identify, qualify, confirm or control the operation of the changeable component(s). The encoded information may be stored in any suitable electronic storage medium and may be embedded in a chip or microchip mounted on or in the changeable component(s). Examples of the types of encoded information that may be stored include but are not limited to; unique identifier(s) for the changeable components (e.g., manufacturer identification, part number, lot number, etc.), indications of whether the changeable component(s) have previously been used (e.g., an encoded indication of first use), indications of whether the changeable component(s) is/are expired (e.g., encoded expiration date), operational characteristic(s) of the changeable component(s) (e.g., encoded indications of the size, type, volume, etc. of the changeable component(s). Examples of the types of information storage that may be utilized include but are not necessarily limited to: non-volatile random access memory (RAM), non-volatile flash memory, electrically erasable programmable read-only memory (EEPROM) or ferroelectric random access memory (FRAM). The extracorporeal control system may comprises a controller (e.g., a processor) programmed to take one or more actions in response to the encoded information. For example, the controller may be programmed to determine whether the encoded information meets a prerequisite requirement and to proceed with warming or cooling of the subject's body only if said prerequisite requirement is met.

In another aspect, the disclosed heat exchange system includes a thermal exchange engine for warming or cooling a thermal exchange fluid. Such thermal exchange engine comprises thermal exchange plates or evaporators which are alternately coolable by circulation of refrigerant through the plates and warmable by heaters positioned on or in the plates. A cassette receiving space is located between the temperature controlled plates and is configured for receiving a cassette or heat exchanger. The cassette comprises a frame and an expandable vessel, such as, for example, a bag or other expandable fluid containing vessel. The expandable vessel is fillable with thermal exchange fluid, for example, after the cassette has been inserted into the cassette receiving space. Heat is thereby transferred between the refrigerant and the thermal exchange fluid or the heater(s) and the thermal exchange fluid. In some embodiments, outer surface (s) of the expandable vessel may be coated with a release material, covered with a layer of releasable material or otherwise treated or modified to deter sticking of the expandable vessel to the adjacent thermal exchange plates. In some other aspects, surface(s) of the thermal exchange plates and/or surfaces of the expandable vessel or a layer on a surface of the expandable vessel' may be textured or provided with holes, groves or other surface features to deter sticking of the expandable vessel to the adjacent thermal exchange plates. In some aspects, the cassette may comprise a housing attached to an insertable portion (for example, the frame and expandable vessel) by a hinged attachment such that the cassette may be disposed in a folded or dosed configuration prior to use and converted to an unfolded or open configuration at the time of use. Such hinged connection between the housing and the insertable portion may be constructed so that, once unfolded or opened, the cassette locks in the unfolded or open configuration. In some aspects, a plurality of hooks located in the console or system may be initially positioned in retracted positions allowing insertion of the insertable portion into the cassette receiving space between the thermal exchange plates and, thereafter, may be moved to advanced positions wherein they hold the insertable portion of the cassette within the cassette receiving space.

In still another aspect, the disclosed heat exchange system includes a system configured to circulate warmed or cooled thermal exchange fluid through a body heat exchanger to warm or cool the body or a human or animal subject, wherein the system comprises a first display device which receives signals from one or more temperature sensors and displays temperature data based on signals received from said one or more temperature sensors. The first display device is connectable, by wired or wireless connectivity, to a second display device, such as, for example, a bedside monitor, central unit monitor, remote monitor, and the like, so as to transmit said signals received from said one or more temperature sensors from the first display device to the second display device. The system further comprises circuitry for minimizing or eliminating any effect of ambient temperature on such signals as they are transmitted from the first display device to the second display device. In some embodiments, the signals transmitted from the first display device to the second display device may comprise signals representative of sensed temperatures, such as patient body temperature, temperature of thermal exchange fluid flowing to the body heat exchanger, temperature of thermal exchange fluid flowing from the body heat exchanger, and the like.

In yet another aspect, the disclosed heat exchange system includes a portable heat exchange system that may be transported by ambulance, car, truck, or other method of conveyance, so that treatment of a patient with the portable heat exchange system when emergency personnel first reach the location of the patient. In such an aspect, the portable heat exchange system will be powered by one or more batteries transportably mounted to the portable heat exchange system in a manner that allows the batteries to be replaced, either singly or all at once as needed. In another aspect, the heat exchange system may include a controller having a processor connected to various circuits for monitoring the charge status of each of the one or more batteries configured to power the heat exchange system, and for automatically switching from alternating current to battery-supplied direct current if the alternating current supply is interrupted. In yet another aspect, the processor may monitor the energy capacity of the battery or batteries, and determine when the indicated charge status of a battery is out of sync with its actual charge status. In such an aspect, the processor controls the battery to be drained completely, and then, controls a charging circuit to recharge the battery, while monitoring the charging process to determine the actual amount of energy being stored in the battery. When the battery is completely recharged, the indicated charge status of the battery is synchronized to the actual energy capacity of the battery so as to provide the operator with a correct charge status.

In still another aspect, when more than one battery is determined to need synchronization, the processor controls the synchronization process, staggering the synchronization process so that at least one battery is available for powering the heat exchange device at all times.

In accordance with one embodiment, there is provided a portable system for managing the temperature of a patient during transport, including, a heater/cooler configured to be in fluid communication with a heat transfer catheter configured for insertion into a patient or a heat transfer surface pad; a pump for circulating heat exchange fluid between the heater/cooler and the heat transfer catheter or surface pad; an alternating current power supply configured to provide power to the system when the alternating power supply is connected to a source of alternating current; a processor configured to monitor the alternating current power supply and to cause an indication to be displayed on an indicator on a console if the alternating current power supply connection to the source of alternating current is interrupted; wherein the system is configured to be connected to at least one rechargeable battery or the system includes at least one rechargeable battery, the at least one rechargeable battery configured to provide power to the system when the alternating power supply is not connected to a source of alternating current, wherein the at least one rechargeable battery is capable of powering the system such that the system can deliver at least 50 watts of cooling power; wherein if the system is powered on and wherein the connection to the alternating current source is interrupted, the system automatically switches to receiving power from the at least one rechargeable battery; and wherein the processor, responsive to the interruption of the connection to the alternating current source, transmits a signal to the indicator to alert an operator of the system to the interruption of the connection to the alternating current source and also provides an indication to the operator of the amount of energy remaining in the at least one rechargeable battery.

The rechargeable battery may provide 90-100 Watt-hours of power. The rechargeable battery may be capable of powering the system such that the system can deliver at least 150 watts of cooling power for at least 10 minutes. The rechargeable battery may be capable of powering the system such that the system can deliver 150-700 watts of cooling power for 10-90 minutes. The rechargeable battery may be capable of powering the system such that the system can deliver 600-700 watts of cooling power for at least 10 minutes. When the alternating current power supply is connected to the alternating current power source, the processor may control the alternating current power supply to provide power to the system to operate the system and also to provide power to charge the at least one rechargeable battery.

In another aspect, the system may include a portable housing and a battery pack, wherein the at least one rechargeable battery is mounted in the battery pack, and the battery pack is mounted to the portable housing. The system may automatically switch from the alternating current supply to the battery to provide power to the system without interruption.

In accordance with the disclosure, an embodiment may include a refrigeration circuit having a compressor configured to cool a heat exchange fluid circulating between the heat/cooler and the heat transfer catheter or heat transfer surface pad, and wherein the processor responsive to the interruption of a connection with the alternating current source, controls the compressor to a low speed and to monitors a current draw by the system, and monitors an amount of stored energy in each of the at least one batteries and provides an indication of the amount of energy remaining in each of the at least one batteries to be displayed individually on the console to the operator. In an embodiment, the system may include a main power switch, the main power switch configured to provide power to the console when the main power switch is in a power on state, and to interrupt power to the console when the main power switch is in a power off state. If the alternating current supply is connected to the alternating current source, and the main power switch is in the power off state, the alternating current source may provide power to a charging circuit to charge the at least one rechargeable battery.

In an embodiment, the alternating current power supply may have a direct current output used to power the console and to charge the at least one rechargeable battery, and the processor may monitor a current draw on the direct current output, and adjusts the current to charge the battery in accordance with the power needs of the console so as to limit the current draw from the direct current output. The alternating current power supply may have a 24 volt direct current output, the 24 volt direct current output used to power the console and to charge the at least one rechargeable battery, and wherein the processor monitors a current draw on the 24 volt direct current output and adjusts the current to charge the battery in accordance with the power needs of the console so as to limit the current draw from the 24 voltage direct current output to 10 amps. In another aspect or embodiment, the processor may adjust the current available for charging the at least one rechargeable battery at least once a second. In another embodiment, the processor may adjust the current available for charging the at least one rechargeable battery at a periodic time interval, such as, for example, the periodic time interval being in a range of 0.1 to 10.0 seconds. In yet another embodiment, the processor may be operably connected to the at least one rechargeable battery via a communication bus, the communication bus having a connector for connecting to the at least one rechargeable battery, and the connector may be configured to engage a connector disposed on the at least one rechargeable battery.

In accordance with the disclosure, an embodiment includes a battery pack having at least one bay, the bay sized to receive one rechargeable battery. In an embodiment, the at least one rechargeable battery may have a height dimension of 29-31 cm, a width dimension of 8-10 cm, and a length dimension of 5-7 cm. In another embodiment, the at least one rechargeable battery may have a height dimension of 21-23 cm, a width dimension of 13-15 cm, and a length dimension of 6-8 cm.

In one embodiment in accordance with the disclosure, the processor may control the system to fully deplete the at least one rechargeable battery when the system is not connected to the source of alternating current. In one embodiment, the system may not be connected to the source of alternating current and the system may not be powered on when the system depletes the at least one rechargeable battery.

In accordance with the disclosure, one embodiment may include a portable housing and at least one battery other than the at least one rechargeable battery of the battery pack, the at least one battery mounted within the portable housing. In an embodiment, the at least one battery mounted within the portable housing may not be removable from within the portable housing.

In an embodiment, the processor may be configured to alter or select an operating mode of the system depending on a measured amount of stored energy in the at least one rechargeable battery when the system is disconnected from the source of the alternating current. In an embodiment, the system has a plurality of operating modes, and the processor may be configured to select an operating mode from the plurality of operating modes depending on the amount of energy stored in the at least one rechargeable battery.

In an embodiment, the processor may be configured to determine how much energy is stored in the at least one rechargeable battery, monitor a current draw on the at least rechargeable battery by the system, and select an operation mode from the plurality of operating modes to optimize the power draw on the at least one rechargeable battery to maximize the time the at least one rechargeable battery can provide power to the system. In an embodiment, the processor may be configured to alter the rate of cooling or warming. In an embodiment, the plurality of operating modes may include a maintenance mode and a max cooling mode.

In accordance with the disclosure, a processor may be configured to monitor the amount of current that the alternating current source is capable of providing, and to select or alter a charging mode in response to the measured amount of current and current draw by the system. The charging mode may be a trickle mode, a high-speed charge mode, less than a full charge mode, and/or a full charge mode. In an embodiment, the charging mode may be a trickle mode when the system is treating a patient. In an embodiment, the charging mode may be a trickle mode when the system is treating a patient, but the processor switches the charging mode to a full charge mode or a high-speed mode when the system is powered off or placed in a stand-by mode.

In accordance with the disclosure, there is provided a portable system for managing the temperature of a patient during transport, including a heater/cooler configured to be in in fluid communication with a heat transfer catheter or a heat transfer surface pad, the heater/cooler including a pump for circulating heat exchange fluid between the heater/cooler and the heat transfer catheter or a heat transfer surface pad; wherein the system is configured to connect to a plurality of rechargeable batteries or includes a battery carrier having a plurality of rechargeable batteries which may be mounted therein, each of the plurality of rechargeable batteries having an associated capacity value, the capacity value being related to an amount of energy stored in the battery available to power the system; an alternating current power supply configured to provide power when the alternating power supply is connected to a source of alternating current; a memory for storing the capacity value for each of the plurality of rechargeable batteries, a processor in operable communication with the memory and programmed to: monitor the capacity value of each of the plurality of rechargeable batteries, determine if the stored capacity value of one or more of the plurality of rechargeable batteries needs to be synchronized with a measured value of the capacity value, control a charging circuit, while leaving at least one rechargeable battery available to provide power to the system, to determine a measured capacity for each of the remaining one or more of the plurality of rechargeable batteries by draining the charge in the remaining one or more of the plurality of rechargeable batteries, and then fully charging the remaining one or more of the plurality of rechargeable batteries, measuring the amount of energy stored in each of the remaining one or more of the plurality of rechargeable batteries, and synchronizing the measured amount of energy stored in the remaining one or more of the plurality of rechargeable batteries with the capacity value stored in the memory for the at least one or more of the plurality of rechargeable batteries; and one or more indicators mounted on a console and in operable communication with the processor, each of the one or more indicators controlled by the processor to indicate a capacity of one or more of the plurality of rechargeable batteries In an embodiment, the synchronization may be performed without operator intervention. In an embodiment, the processor may monitor the voltage of each of the rechargeable batteries undergoing synchronization to control the synchronization of the stored capacity value of the battery. In an embodiment, there may also include a gas gauge circuit configured to provide an indication of a level of charge of the one or more rechargeable batteries undergoing synchronization, the gas gauge circuit indicating a level of charge for the one or more rechargeable batteries undergoing synchronization based on the monitored voltage of the rechargeable battery.

In an embodiment, the processor may control the synchronization of the remaining at least one or more rechargeable batteries to stop synchronization of the one or more rechargeable batteries when the system is being operated to heat or cool a patient. In an embodiment, the system may include a housing, and wherein a battery carrier may be mounted to a portion of the housing.

In an embodiment, the processor may be programmed to control charging of the plurality of rechargeable batteries such that different ones of the plurality of rechargeable batteries are charged at different charging currents. In an embodiment, the processor may be programmed to control the charging of the plurality of batteries such that charging a rechargeable battery during synchronization is done at a different current than is used to charge a battery not undergoing synchronization.

In an embodiment, the processor may store a value representative of a last time a rechargeable battery is synchronized for each of the plurality of rechargeable batteries; and wherein the processor periodically compares a current time with the stored last time a rechargeable battery is synchronized to determine if the rechargeable battery requires synchronization. In an embodiment, synchronization may only be performed when the alternating power supply is connected to a source of alternating current.

In accordance with the disclosure, there is provided a portable system for managing the temperature of a patient during transport, including a heater/cooler configured to be in fluid communication with a heat transfer catheter insertable in a patient; a pump for circulating heat exchange fluid between the heater/cooler and the heat transfer catheter; an alternating current power supply configured to provide power when the alternating power supply is connected to a source of alternating current; wherein the system is configured to be connected to or the system includes at least one rechargeable battery configured to provide power to the system when the connection to the source of alternating current is interrupted or not connected; a processor programmed to control operation of the heater/cooler and the pump, the heater/cooler and pump being powered by the alternating current power supply or the rechargeable battery; the rechargeable battery being capable of providing power to the system such that the heater/cooler provides at least 200 watts of cooling power to the patient or to the heat exchange fluid for at least 20 minutes.

In an embodiment, the processor may be configured to charge the rechargeable battery when power is being supplied to the system by the alternating current power supply. In an embodiment, the system may also include a housing, and the rechargeable battery may be disposed in a battery holding container, and the battery holding container may be mounted to a portion of the housing. In an embodiment, the rechargeable battery may be capable of powering the system such that the system can deliver 600-700 watts of cooling power for at least 10 minutes. In an embodiment, the alternating current power supply may be connected to the alternating current power source, and the processor may control the alternating current power supply to provide power to the system to operate the system and also to provide power to charge the at least one rechargeable battery.

In an embodiment, the system may also include a refrigeration circuit having a compressor configured to cool a heat exchange fluid circulating between the heat/cooler and the heat transfer catheter or heat transfer surface pad, and wherein the processor is responsive to the interruption of a connection with the alternating current source to control the compressor to a low speed and to monitor a current draw by the heat exchange system, to monitor an amount of stored energy in at least one rechargeable battery, and to display an indication of the amount of energy remaining in the rechargeable battery on the console to the operator. In an embodiment, the system may also include a main power switch, the main power switch configured to provide power to the console when the main power switch is in a power on state, and to interrupt power to the console when the main power switch is in a power off state. In an embodiment, if the alternating current supply is connected to the alternating current source, and the main power switch is in the power off state, the alternating current source may provide power to a charging circuit to charge the at least one rechargeable battery. In an embodiment, the alternating current power supply may also have a direct current output used to power the console and to charge the at least one rechargeable battery, and wherein the processor may monitor a current draw on the direct current output and the processor may adjust the current to charge the battery in accordance with the power needs of the console so as to limit the current draw from the direct current output. In an embodiment, the alternating current power supply may have a 24 volt direct current output, the 24 volt output used to power the console and to charge the at least one rechargeable battery, and wherein the processor may monitor a current draw on the 24 volt direct current output, and may adjust the current to charge the battery in accordance with the power needs of the console so as to limit the current draw from the 24 voltage direct current output to 10 amps. In an embodiment, the processor may adjust the current available for charging the at least one rechargeable battery at least once a second. In an embodiment, the processor may adjust the current available for charging the at least one rechargeable battery at a periodic time interval, the periodic time interval being in a range of 0.1 to 10.0 seconds.

In an embodiment, the processor may be operably connected to the at least one rechargeable battery via a communication bus, the communication bus having a connector for the at least one rechargeable battery, the connectors configured to engage a connector disposed on the at least one rechargeable battery. In an embodiment, the battery holding container may include at least one bay, the bay sized to receive one rechargeable battery. In an embodiment, the rechargeable battery may have a height dimension of 29-31 cm, a width dimension of 8-10 cm, and a length dimension of 5-7 cm. In an embodiment, the rechargeable battery may have a height dimension of 21-23 cm, a width dimension of 13-15 cm, and a length dimension of 6-8 cm. In an embodiment, the rechargeable battery may be configured to power the system on when the system is not connected to the source of alternating current. In an embodiment, the rechargeable battery may be configured to power the system on and initiate treatment. In an embodiment, the rechargeable battery may be configured to power the system in a MAX cooling mode. In an embodiment, if the processor does not receive confirmation from an operator that the system should be powered on, the processor may power off the system.

In an embodiment, the processor may be configured to alter or select an operating mode of the system depending on a measured amount of stored energy in the at least one rechargeable battery when the system is disconnected from the source of the alternating current. In an embodiment, the system may have a plurality of operating modes, and the processor may be configured to select an operating mode from the plurality of operating modes depending on the amount of energy stored in the at least one rechargeable battery. In an embodiment, the processor may be configured to determine how much energy is stored in the at least one rechargeable battery, monitor a current draw on the at least rechargeable battery by the system, and select an operation mode from the plurality of operating modes to optimize the power draw on the at least one rechargeable battery to maximize the time the at least one rechargeable battery can provide power to the system. In an embodiment, the processor may be configured to alter the rate of cooling or warming. In an embodiment, the plurality of operating modes may include a maintenance mode and a max cooling mode. In an embodiment, the processor may be configured to monitor the amount of current that the alternating current source is capable of providing, and select or alter a charging mode in response to the measured amount of current and current draw by the system. In an embodiment, the charging mode may be a trickle mode. In an embodiment, the charging mode may be a high-speed charge mode. In an embodiment, the charging mode may be less than a full charge mode. In an embodiment, the charging mode may be a full charge mode. In an embodiment, the charging mode may be a trickle mode when the system is treating a patient. In an embodiment, the charging mode may be a trickle mode when the system is treating a patient, but the processor may switch the charging mode to a full charge mode or a high-speed mode when the system is powered off or placed in a stand-by mode.

In accordance with the disclosure, an embodiment provides a transportable rechargeable battery, including at least one rechargeable battery having one or more battery cells enclosed by a housing; the at least one rechargeable battery connected to one or more connectors mounted on or disposed in a surface of the housing, wherein the rechargeable battery has a height dimension of 21-30 cm, a width dimension of 8-15 cm, and a length dimension of 5-8 cm; and a battery receiver having one or more connectors mounted on or disposed in a surface of the battery receiver, the battery receiver and the one or more connectors configured to receive the at least one rechargeable battery such that the one or more connectors mounted on or disposed in the surface of the housing are engaged with the one or more connectors mounted on or disposed in the surface of the battery receiver when the at least one rechargeable battery is mounted in the battery receiver; wherein the transportable rechargeable battery is configured for attachment to a transportable temperature management system and to power the system to provide treatment to a patient during transport of the patient from one location to another location. The battery receiver may have a dedicated bay for receiving the at least one transportable rechargeable battery. In an embodiment, the at least one rechargeable battery may provide 90-100 Watt-hours of power and is capable of powering the transportable temperature management system such that the system provides a cooling power of 400-600 watts. In an embodiment, the at least one rechargeable battery may provide 90-100 Watt-hours of power and is capable of powering the transportable temperature management system such that the system provides a cooling power of 400-600 watts for at least 10 minutes. In an embodiment, the at least one rechargeable battery may be a Lithium-Ion battery.

In some aspects, the processor is configured to cause the heater/cooler to operate in a low-power mode when the alternating current power supply connection to the source of alternating current is interrupted. In some implementations, the system includes a compressor connected to the heater/cooler. The compressor is configured to cool the heater/cooler. In some implementations, causing the heater/cooler to operate in a low-power mode includes causing the compressor cycle between an ON state and an OFF state.

In some implementations, the processor is configured to monitor a temperature of the heater/cooler. The processor is configured to cycle the compressor to the ON state when the temperature exceeds an upper threshold and until the temperature is below a lower threshold. In some implementations, the processor is configured to cycle the compressor to the OFF state when the temperature is below the lower threshold and until the temperature exceeds the upper threshold.

In some implementations, the upper threshold is above 16 degrees Celsius. The lower threshold is about 5 degrees Celsius. In some implementations, the upper threshold and the lower threshold are based on one or more operating parameters of the heater/cooler. In some implementations, the upper threshold and the lower threshold are based a desired patient temperature, a patient physiology, or both. In some implementations, causing the heater/cooler to operate in a low-power mode comprises causing the compressor to operate at a slower speed relative to a typical operating speed of the compressor.

In some implementations, the processor is configured to access a data profile specifying a given operation of the compressor. The processor is configured to determine a projection specifying how long the battery is capable of powering the system. In some implementations, the data profile specifies at least one of: a frequency of cycling the compressor to an ON state and an OFF state, a threshold temperature of the heater/cooler for activating or deactivating the compressor, and a speed for operating the compressor.

In some implementations, system includes an uninterruptable power supply (UPS). Automatically switching to receiving power from the at least one rechargeable battery includes automatically supplying power from a battery of the UPS when the alternating current source is interrupted or is insufficient for a load of the system. The processor is configured to receive a signal sent by the UPS indicating that the UPS is supplying power from the battery. The processor is configured to cause the heater/cooler to operate in a low-power mode in response to receiving the signal.

In an aspect, a portable system for managing the temperature of a patient during transport includes a heater/cooler configured to be in fluid communication with a heat transfer catheter configured for insertion into a patient or a heat transfer surface pad. The system includes a control console comprising a processor configured to control operation of the heater/cooler. The processor is configured to receive a low-power signal indicating that a connection to a source of alternating current is interrupted and power is supplied by a battery. The processor is configured to cause the heater/cooler to operate in a low-power mode in response to receiving the low-power signal.

In some implementations, the system includes an alternating current power supply configured to provide power to the control console and the heater/cooler, wherein the alternating current power supply receives power from a source of alternating current. The alternating current power supply is configured to send the low-power signal to the processor.

In some implementations, an uninterruptable power supply (UPS) provides alternating current to the alternating current power supply and receives power from the source of alternating current, wherein the processor is configured to receive a signal sent by the UPS indicating a connection to the source of alternating current is interrupted and a UPS battery is supplying power.

In some implementations, the system includes at least one battery. The processor is configured to switch to receive power from the battery in response to receiving the low-power signal. In some implementations, causing the heater/cooler to operate in a low-power mode comprises causing a compressor of the heater/cooler to cycle between an ON state and an OFF state.

Other features and advantages of the present invention will become apparent from the following detailed description, taken in conjunction with the accompanying drawings, which illustrate, by way of example, the principles of the invention.

BRIEF DESCRIPTION OF THE DRAWINGS

The following detailed description and examples are provided for the purpose of non-exhaustively describing some, but not necessarily all, examples or embodiments of the disclosed heat exchange system, and shall not limit the scope of the disclosed heat exchange system in any way.

DETAILED DESCRIPTION

Figure 1:
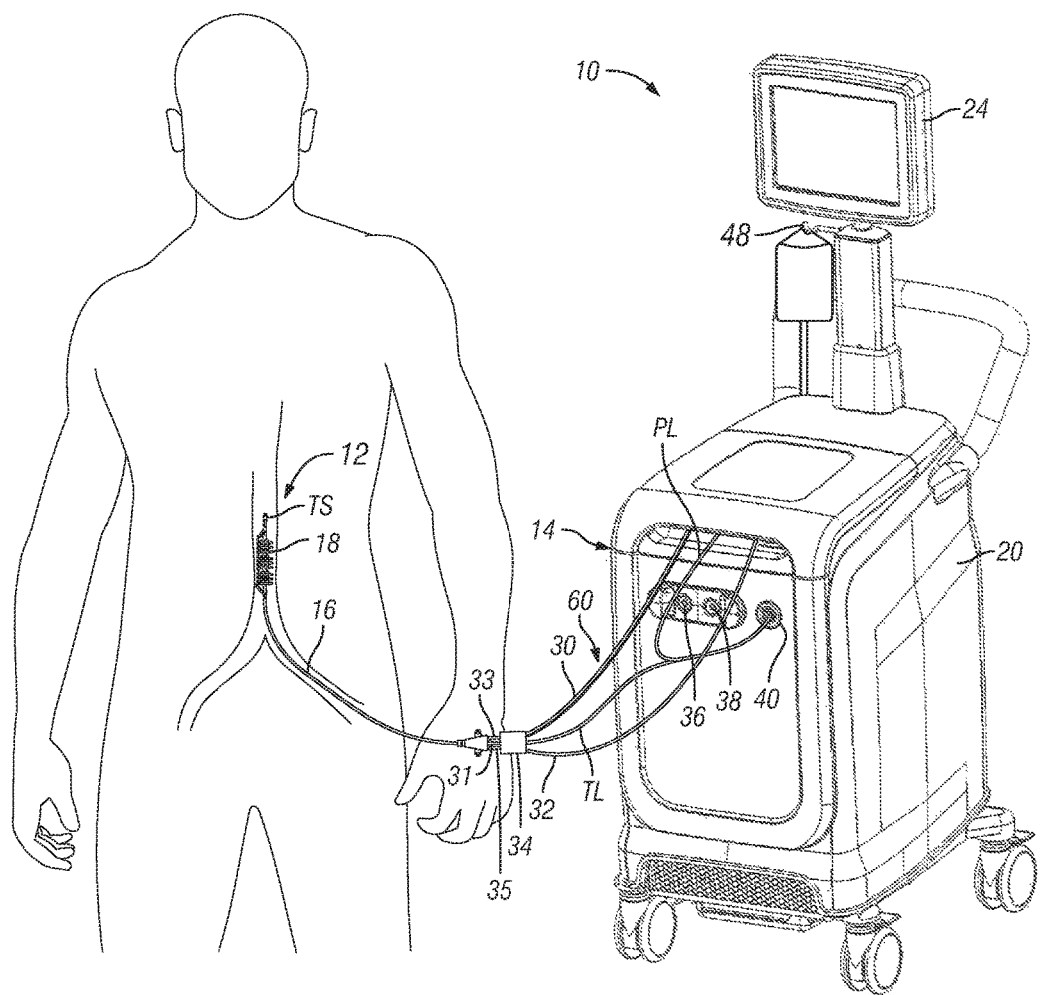
FIG. 1 shows one embodiment of an endovascular heat exchange system comprising an endovascular heat exchange catheter, an extracorporeal control console and a tubing/cassette/sensor module assembly useable for operatively connecting the heat exchange catheter to the control console.

The following detailed description and the accompanying drawings to which it refers are intended to describe some, but not necessarily all, examples or embodiments of the disclosed heat exchange system. The described embodiments are to be considered in all respects only as illustrative and not restrictive. The contents of this detailed description and the accompanying drawings do not limit the scope of the disclosed heat exchange system in any way.

It is believed that the sooner a patient is cooled after ischemic insult, the better the therapy outcome. In many cases, thermal treatment will begin when the patient is placed into an ambulance. Thus, it is advantageous to provide a means to thermally treat these patients in the ambulance, with thermal treatment continuing when the patient reaches a care facility. Being able to automatically switch between alternating current to direct current power is also advantageous whenever a patient needs to be transported from one location in a care facility to another location, and thermal treatment needs to continue while the patient is being transported, such as, for example, when a patient arrives in an emergency room, and then needs to be transported from the emergency room to a catheterization laboratory, when the patient is moved from one location to an intensive care unit, or when the patient is moved from one room to another in the care facility.

It is also advantageous for the heat exchange system to be capable of automatically determining when the actual capacity of one or more of the batteries used to power the heat exchange system needs to be measured so that the system can re-learn the actual capacity of the battery so that a battery capacity indicator may be synchronized with the actual capacity of the battery so that an operator may determine the correct charge status of the one or more batteries in a manner so that at least one of the batteries is always ready to power the heat exchange system.

A further advantage of the various exemplary embodiments of the heat exchange system disclosed herein is that the batteries and battery management system described herein may provide as much as 600 watts of cooling power for as long as 30 minutes while the system is disconnected from an alternating current source and powered solely by battery during transport of a patient from one location to another.

As explained herein, a heat exchange catheter system such as is described below has the unique ability to cool an adult human subject's body to a hypothermic temperature below 34 degrees C., and preferably between 32 degrees C. and 34 degrees C. or 32 degrees or below, in approximately 20 minutes. This rapid induction of hypothermia allows caregivers to select an appropriate time to perform a reperfusion procedure after the subjects body temperature has been lowered to the target temperature. Prior studies have indicated that if hypothermia below 35 degrees C. is effected prior to reperfusion, the severity of reperfusion injury, and hence the size or severity of any permanent tissue infarction, is reduced. Applicant has performed a pilot study using a protocol for deterrence of reperfusion injury in human subjects presenting at hospital emergency departments suffering from acute ST elevation myocardial infarction (STEMI). In this pilot study, subjects were randomized into hypothermia and non-hypothermia (control) groups. Subjects in the hypothermia group received standard anti-shivering medication and a heat exchange catheter was placed in the inferior vena cava (IVC). A high power heat exchange catheter system was then used to rapidly cool the body of each subject in the hypothermia group to a temperature below 34 degrees C. within <90 minutes of the subject's arrival in the emergency department. Each subject then underwent percutaneous coronary Intervention (PCI) resulting in reperfusion of the ischemic myocardium. The subjects in the hypothermia group had a body temperatures at the time of reperfusion (i.e., measured at PCI wire crossing) of 33.6+1.0 degrees C.

Following completion of the reperfusion procedure, hypothermia was maintained in each hypothermia group subject for a period of three hours at a target temperature setting of 32 degrees C. Thereafter, the hypothermia group subjects were gradually rewarmed to a body temperature of 36 degrees C.

Four to six days after the event, each subject underwent cardiac magnetic resonance imaging (cMR) and infarct size divided by left ventricular mass (IS/LVM) was determined. On average, subjects in the hypothermia group had a 7.1% absolute change in IS/LVM and approximately a 30% relative reduction compared to the non-hypothermia controls. A 5% absolute change in IS/LVM is generally viewed as a good clinical outcome.

The results of this pilot study, when compared with previously reported data, suggests that 1) cooling of the subject's body temperature at a faster rate (i.e., made possible by using a high cooling power system) results in reduced infarct size measured as IS/LVM, 2) There appears to be a dose-response relationship whereby lower body temperature at the time of reperfusion correlates with greater protection against reperfusion injury and, thus, smaller infarct size.

As will be understood, beginning heat exchange treatment as early after the ischemic event has occurred is beneficial to the patient. Accordingly, it is appreciated that a heat exchange device that may operate while powered by direct current provided by one or more batteries, such as the device, system, and methods described herein is advantageous.

Such a system will be described below in reference to a heat exchange system configured to be powered by alternating current, such as available from the type of power connections available in an emergency room or care facility environment, but modified to also be powered using direct current provided by a battery or batteries when a connection to an alternating current power source is not available.

Referring now to the drawings in detail, in which like reference numerals indicate like or corresponding elements among the several figures, there is shown in FIG. 1 one embodiment of an intravascular or endovascular heat exchange system 10 in operation to control the body temperature of a human subject. Such systems are described in U.S. patent application Ser. Nos. 15/594,541 and 16/052,551 incorporated by reference in their entirety herein. This endovascular heat exchange system 10 generally comprises an endovascular heat exchange catheter 12, an extracorporeal control console 14, a tubing/cassette/sensor module assembly 60 or cassette assembly which facilitates connection of the catheter 12 to the control console 14 and a temperature sensor TS. In at least some embodiments, the catheter 12, tubing/cassette/sensor module assembly 60 or cassette assembly and temperature sensor TS may be disposable items intended for a single use, while the control console 14 may be a non-disposable device intended for multiple uses.

In the embodiment shown, the endovascular heat exchange catheter 12 comprises an elongate catheter body 16 and a heat exchanger 18 positioned on a distal portion of the catheter body 16. Inflow and outflow lumens (not shown) are present within the catheter body 16 to facilitate circulation of a thermal exchange fluid (e.g., sterile 0.9% sodium chloride solution or other suitable thermal exchange fluid) through the heat exchanger 18. Optionally, the catheter shaft 16 may also include a working lumen (not shown) which extends through the catheter body 16 and terminates distally at an opening in the distal end of the catheter body 16. Such working lumen may serve as a guidewire lumen to facilitate insertion and position of the catheter 12 and/or may be used after insertion of the catheter 12 for delivery of fluids, medicaments or other devices. For example, as shown in FIG. 1, in some embodiments, the temperature sensor TS may be inserted through the catheter's working lumen and advanced out of the distal end opening to a location beyond the distal end of the catheter body 16. Alternatively, in other embodiments, the temperature sensor TS may be positioned at various other locations on or in the subject's body to sense the desired body temperature(s). Various heat exchange catheters may be used in the embodiments described herein.

Non-limiting examples of other heat exchange catheters and related apparatus that may be used are described in U.S. Pat. No. 9,492,633, and United States Patent Application Publications Nos. 2013/0090708, 2013/0178923, 2013/0079855, 2013/0079856, 2014/0094880, 2014/0094882, 2014/0094883, and unpublished, co-pending U.S. patent application Ser. Nos. 15/395,858, 15/395,923 and 15/412,390, the entire disclosure of each such patent and application being expressly incorporated herein by reference. Other examples of catheters that may be used in cooperation with this disclosed heat exchange system include those commercially available from ZOLL Circulation, Inc., San Jose, Calif., such as the Cool Line® Catheter, Icy® Catheter, Quattro® Catheter, Solex 7® Catheter, InnerCool® RTx Accutrol Catheter and the InnerCool RTx Standard Catheter. Additionally incorporated herein by reference is the entire disclosure of U.S. patent application Ser. No. 15/594,539 entitled Advanced Systems and Methods for Patent Body Temperature Control, filed on May 12, 2017.

The extracorporeal control console 14 generally comprises a main housing 20 and a console head 24. As subsequently described in detail, the main housing 20 contains various apparatus and circuitry for warming/cooling thermal exchange fluid to controlled temperature(s) and for pumping such warmed or cooled thermal exchange fluid through the catheter 18 to effectively modify and/or control the subject's body temperature. The console head 24 comprises a display device or user interface, such as a touch screen system, whereby certain information may be input by, and certain information may be displayed to, users of the system 10. On the housing 20 there are provided a first connection port 40 for connection of a temperature sensor TS that is inserted through the heat exchange catheter 12 as shown in FIG. 1 as well as other connection ports 36, 38 for connection of additional or alternative types of temperature sensors and/or other apparatus.

Figure 3:
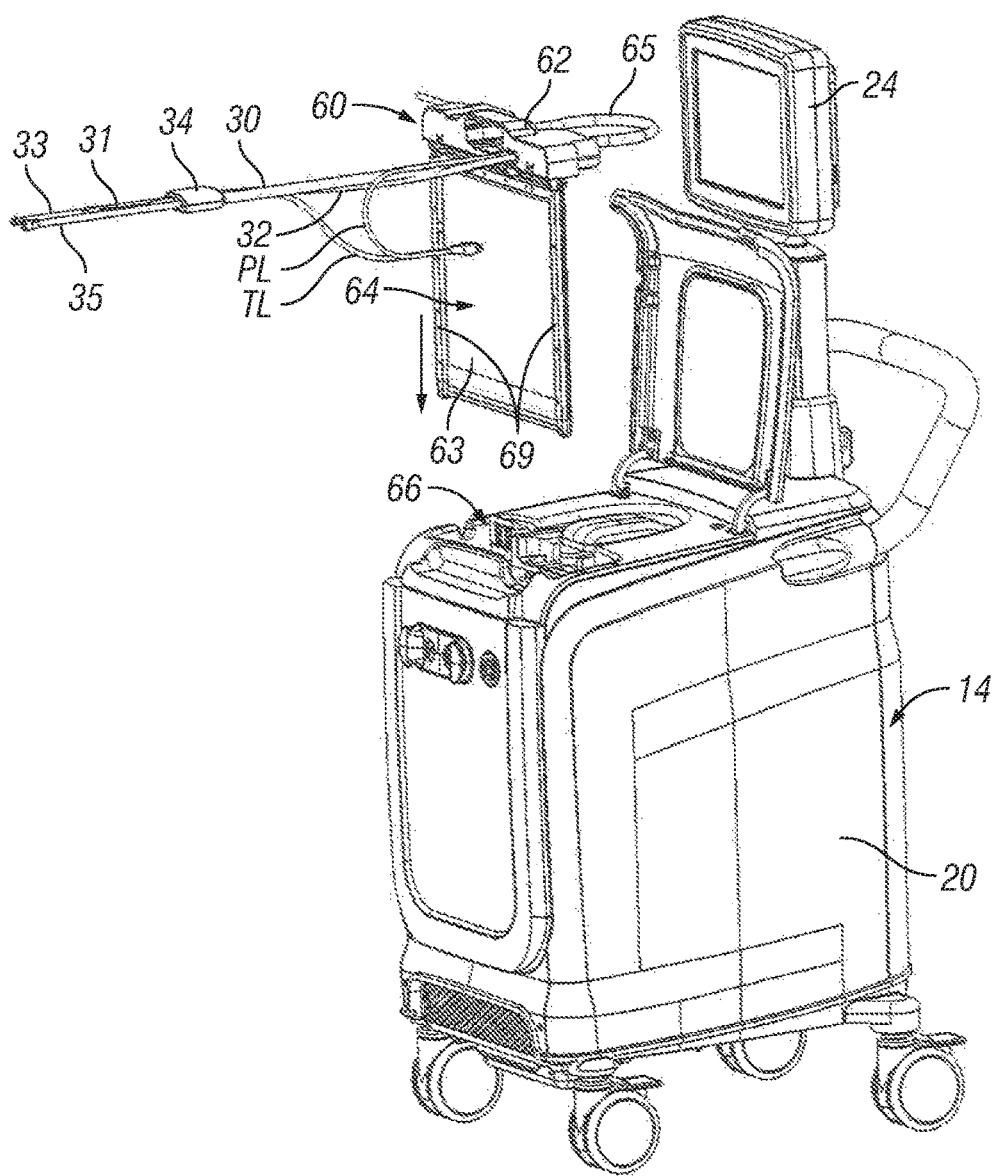
FIG. 3 is an exploded view of the control console with its access cover in an open position and the tubing/cassette/sensor module assembly staged for insertion in, and operative connection to, the control console.
Figure 4:
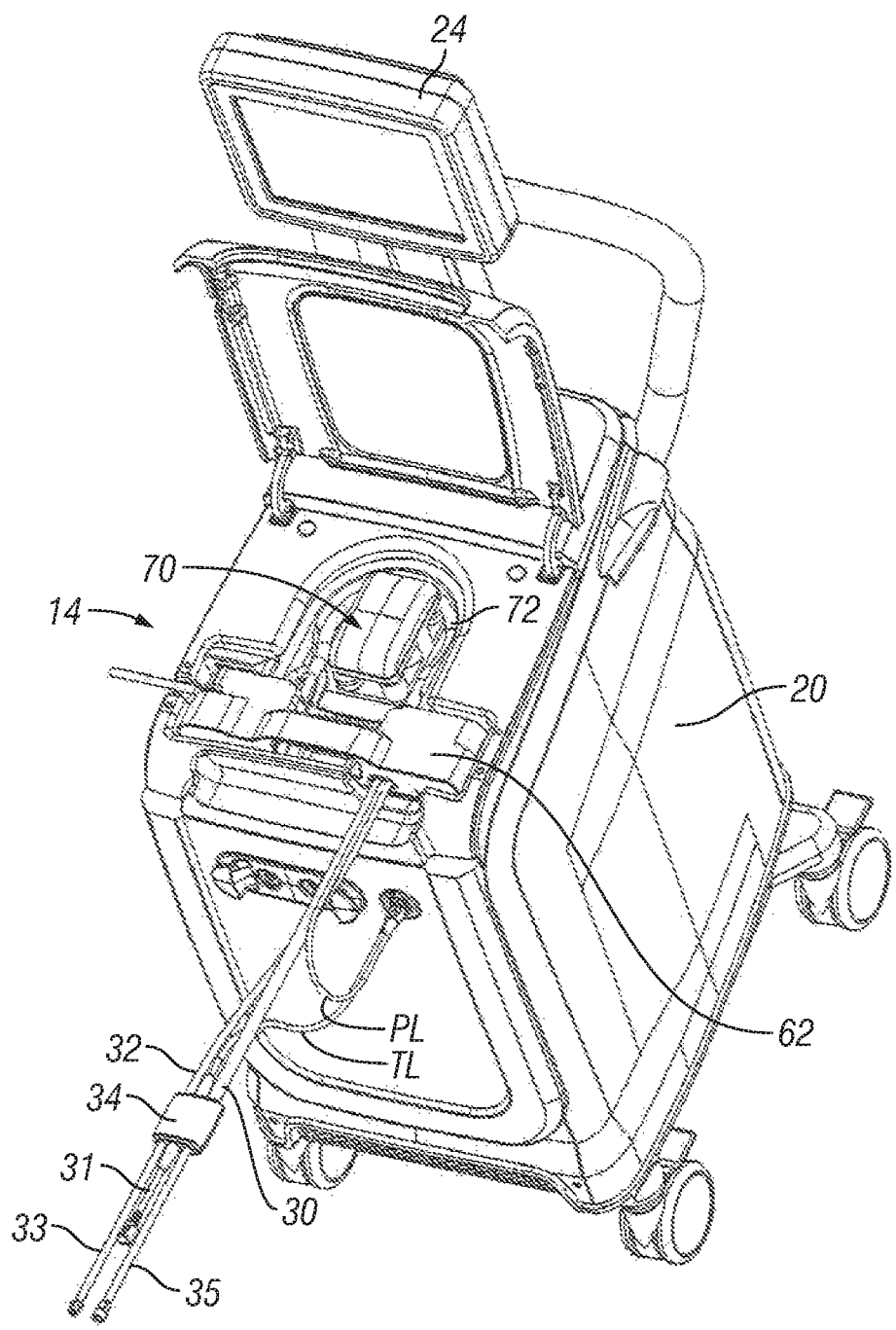
FIG. 4 is a top (perspective) view of the control console with its access cover in an open position and the tubing/cassette/sensor module assembly operatively inserted in and connected to the control console.
Figure 5:
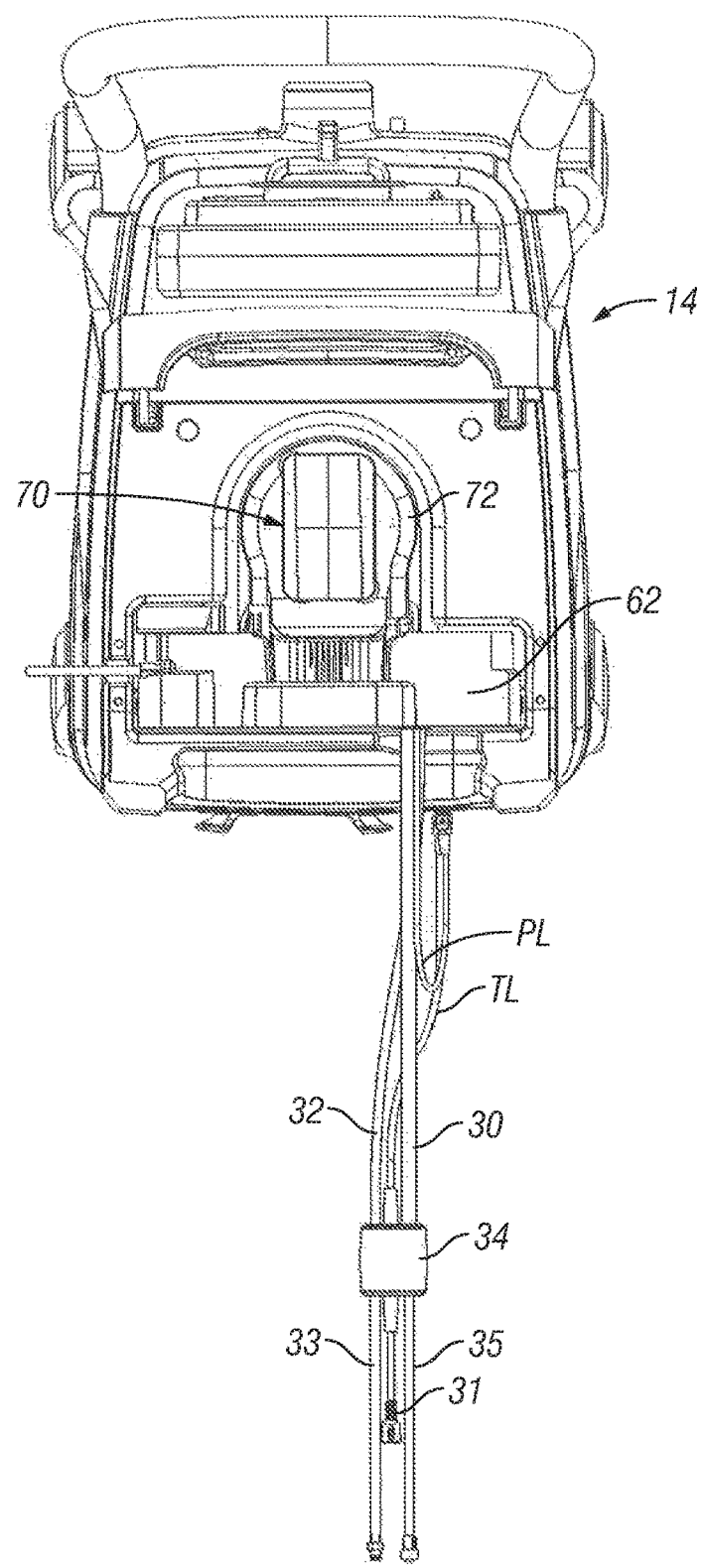
FIG. 5 is a top (plan) view of the control console with its access cover in an open position and the tubing/cassette/sensor module assembly operatively inserted in and connected to the control console.
Figure 6:
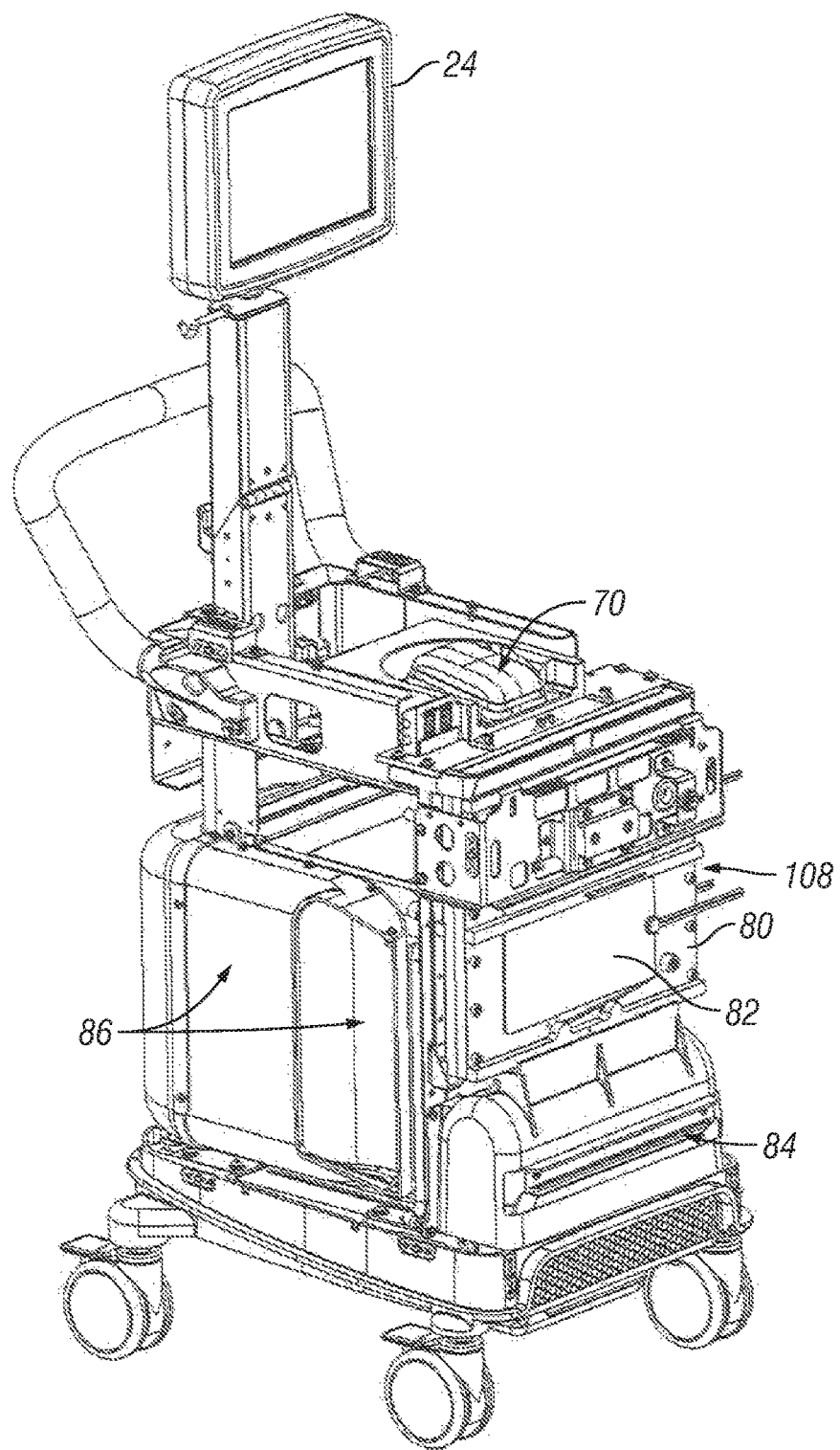
FIG. 6 is a right/front perspective view of the control console with its housing and access cover removed.
Figure 7:
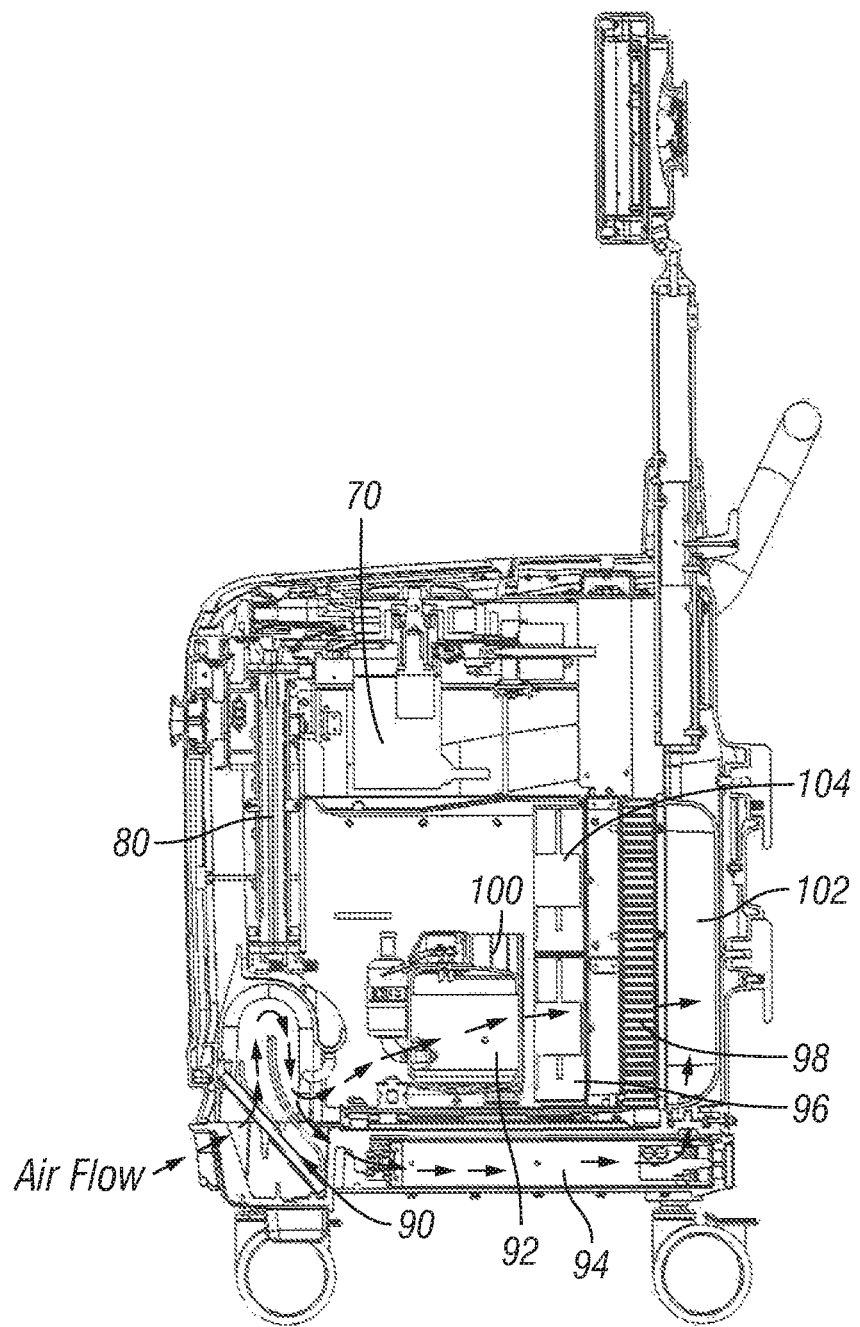
FIG. 7 is a left cross-sectional view of the control console.
Figure 8:
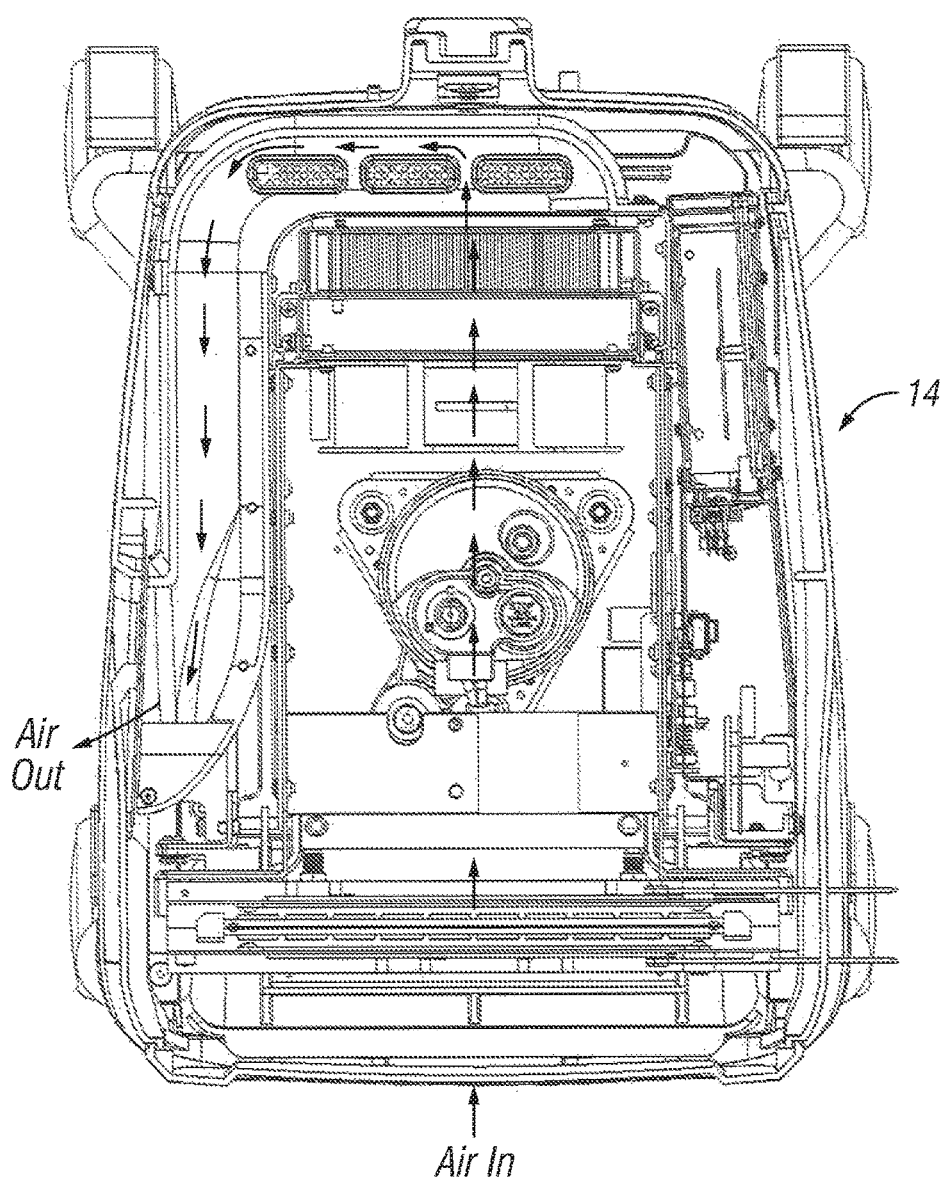
FIG. 8 is a top cross-sectional view of the control console.
Figure 9:
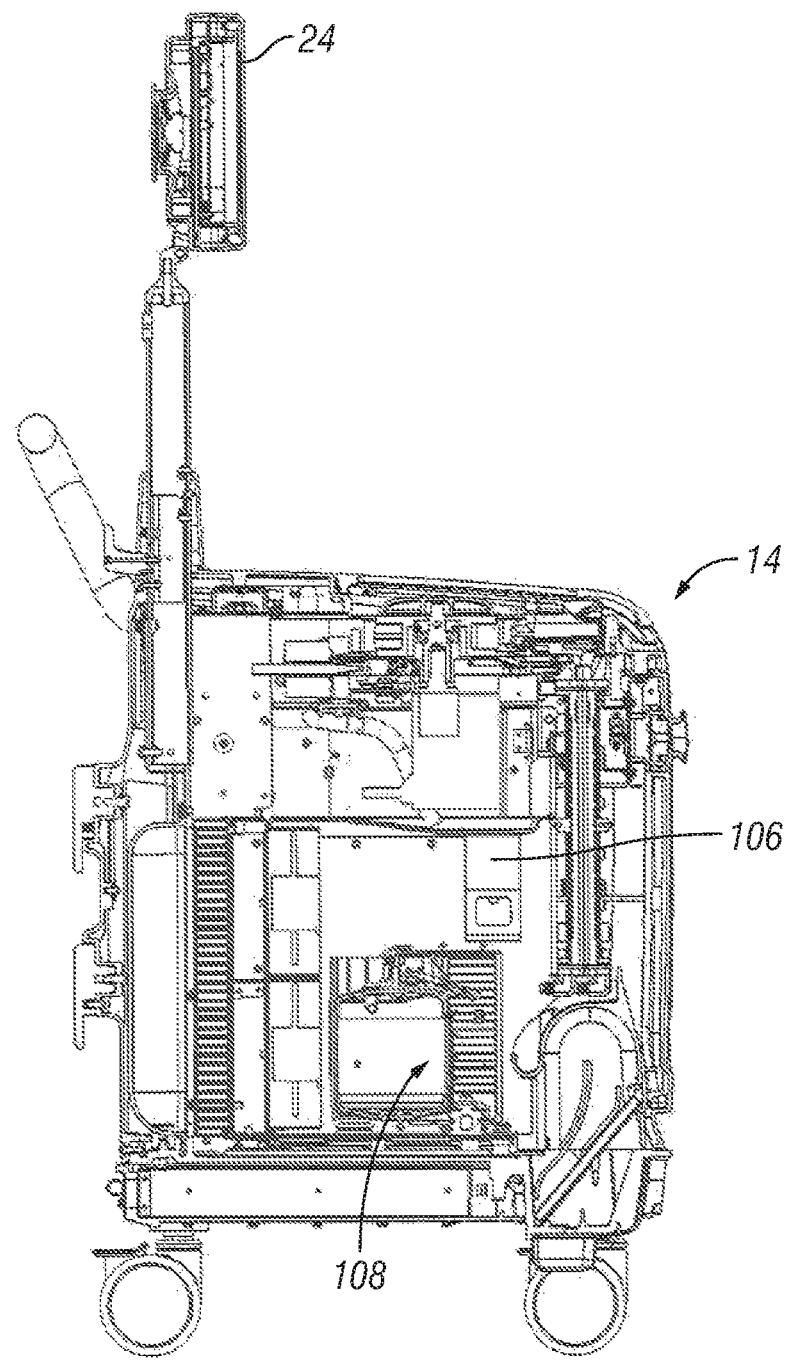
FIG. 9 is a right cross-sectional view of the control console.
Figure 10:
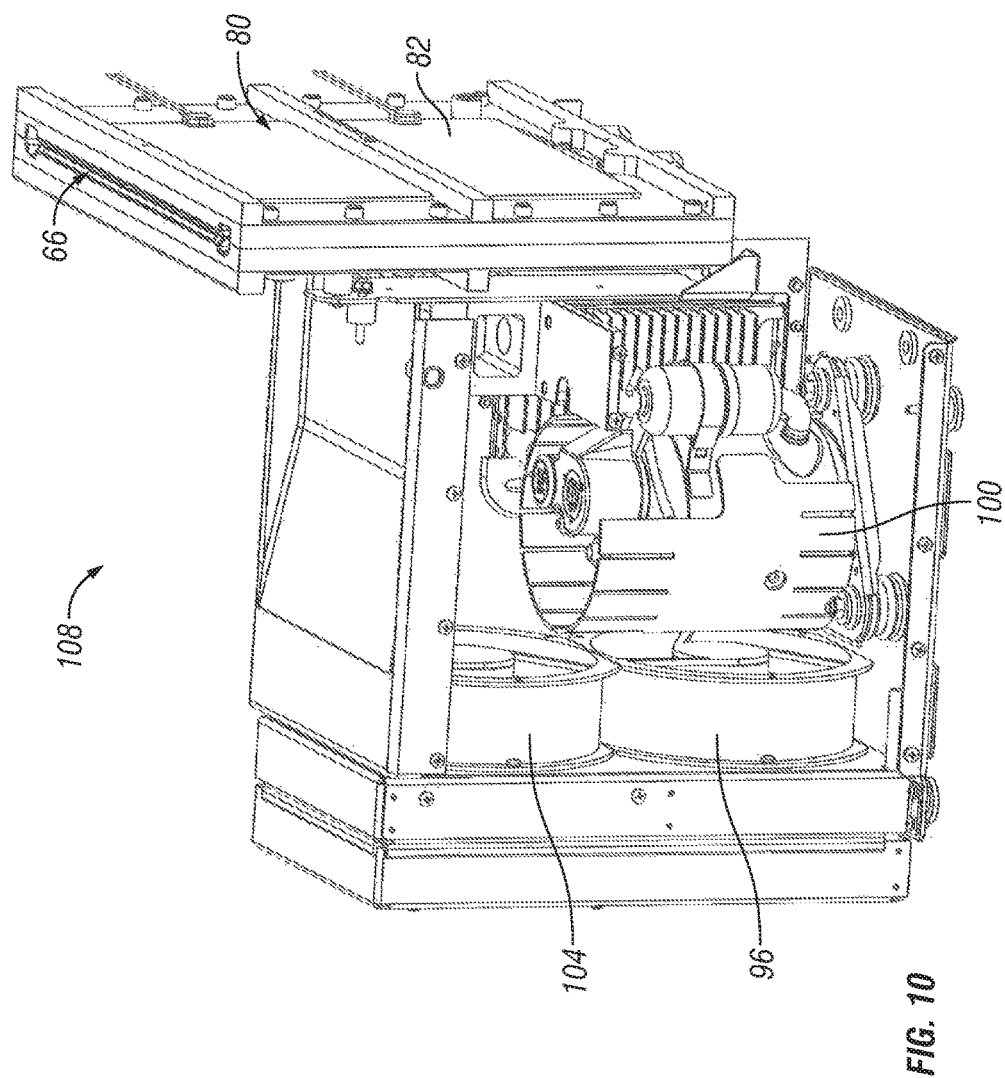
FIG. 10 is a perspective view of a thermal exchange engine component of the control console.

The tubing/cassette/sensor module assembly 60 or cassette assembly, which is seen in further detail in FIGS. 3-5, generally comprises a sensor module 34, an inflow conduit 32, inflow connector 33, outflow conduit 30, outflow connector 31, temperature lead TL, temperature lead connector 35, pressure lead PL, cassette 64, cassette housing 62 and peristaltic pump tubing 65.

Figures 2A, 2B:
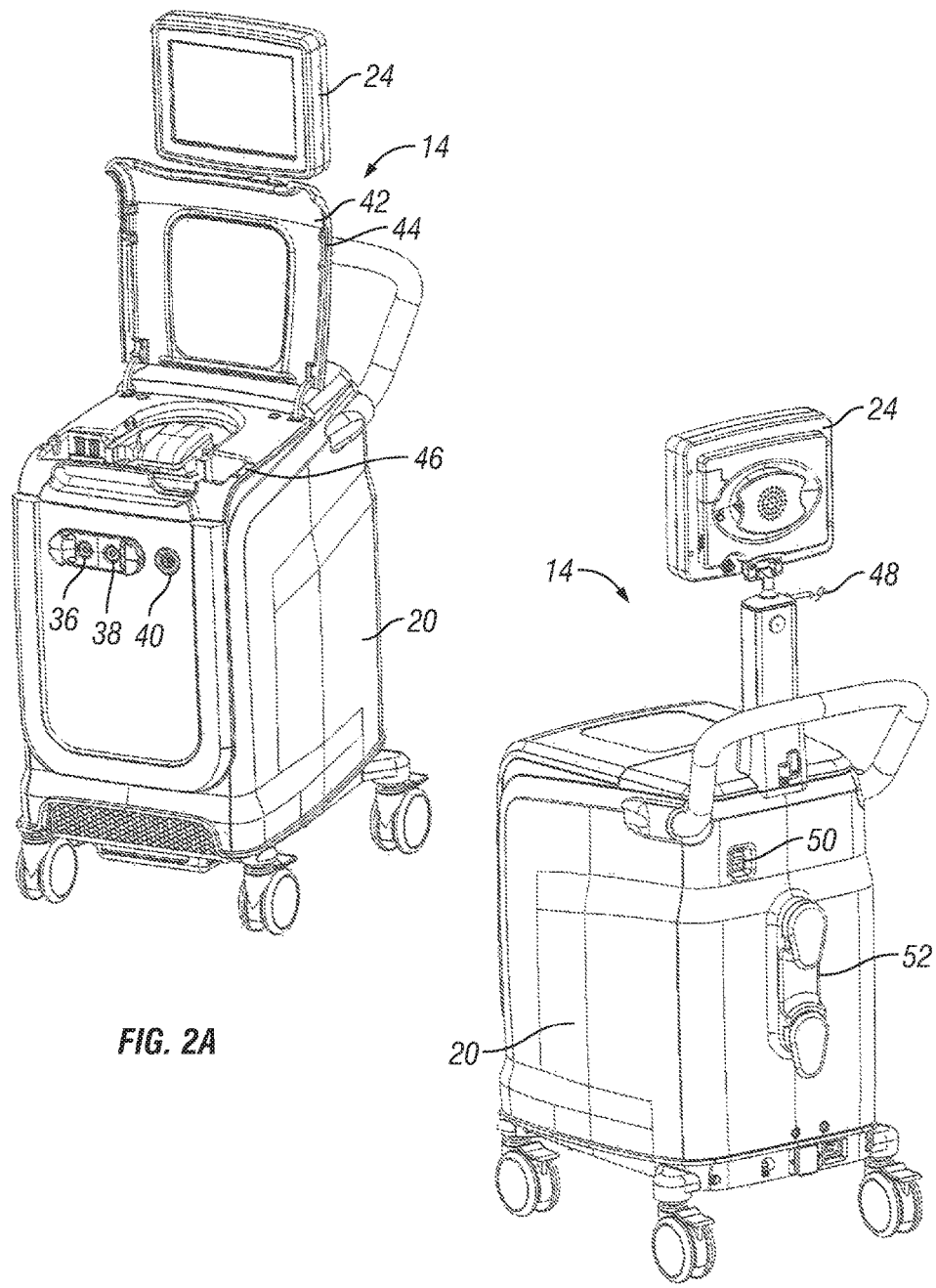
FIG. 2A is a left/front perspective view of the control console with its access cover in an open position.
FIG. 2B is a left/rear perspective view of the control console.

FIGS. 2A through 9 show further detail of the components within the housing 20 and the manner in which the tubing/cassette/sensor module assembly 60 or cassette assembly is inserted in and connected to the control console 14. As seen in FIGS. 2A through 3, the control console 14 has an openable/closable access cover 42 which, when opened, permits insertion of the cassette 64 into a cassette receiving space 66 as well as other connection of the tubing/cassette/sensor module assembly 60 or cassette assembly to other components of the system described below. A magnet 44 on the access cover 42 interacts with a magnetic sensor 46 to emit signal(s) indicating whether the access cover 42 is opened or closed. Other sensors and detection mechanisms known to persons having skill in the art may be utilized as well. The system controller located in the housing 20 may be programmed to halt running of certain components of the system when the access cover 44 is opened. On the rear of the housing 20, there is provided a power switch 50 and a power cord holder 52. A bracket 48 is provided on an upstanding portion of the housing which supports the console head 24 for hanging a bag or container of fluid.

As seen in FIGS. 3 through 5, with the access cover 42 in an open position, the cassette 64 is insertable downwardly into the cassette receiving space 66 and the pump tubing 65 is insertable into a tubing raceway 72 of pump 70.

FIGS. 6 through 10 provide partially disassembled and sectional views that reveal various components of the control console 14. The thermal exchange engine 108, includes a refrigeration system which comprises a compressor 92, stepper motor for turning an expansion valve 106, fans 96 and 104, condenser 98 and compressor heat sink 100. The heat sink may be a metallic, e.g., aluminum, cylindrical enclosure that surrounds the compressor. The heat sink is in contact with the compressor and increases the surface area of the compressor to facilitate enhances removal of heat from the compressor. The thermal exchange system is powered by power supply 94. Thermal exchange plates 80, are provided to alternately warm or cool thermal exchange fluid as it circulates through a cassette 64 that has been inserted in the cassette receiving space 66 between the thermal exchange plates. Resistance heaters 82 are mounted on the plates 80 for warming the plates 80 when operating in a warming mode and a refrigerant, such as Refrigerant R143a (1,1,1,2 Tetrafluoroethane) is compressed by the compressor 92 and circulated through the condenser 98 and plates 80 to cool the plates when operating in a cooling mode. In certain embodiments, heaters may include a thermal cutout switch for automatically turning one or more of the heaters off if the heaters were to overheat.

When operating in a cooling mode, the thermal exchange engine 108 emits heat. Fans 96 and 104 circulate air through air plenums or spaces adjacent to the thermal exchange engine 108 and over surfaces of the compressor and compressor heat sink 100 to exhaust emitted heat and maintain the thermal exchange engine 108 at a suitable operating temperature. Specifically, in the embodiment shown, air enters air intake 84 through filter 90, circulates through the device as indicated by arrows on FIGS. 7 and 8, and is exhausted through an air outlet or exhaust vent on a side of the console 14 as shown specifically in FIG. 8. The airflow pathway is specifically configured to minimize the amount of sound that escapes from the system via the airflow pathway and is audible to a user or patient. The airflow pathway includes a convoluted pathway or channels that provide reflective surfaces to contain the acoustic energy within the cooling engine enclosure. In addition, the interior of the intake and exhaust ducts and pathway or channels are lined with an acoustically absorbent material, e.g., open-celled elastomeric foam. The combination of these features minimizes the amount of sound that escapes the system, such as sound generated by the fans and compressor. For example, in certain embodiments, the operating noise level of a system may not exceed 65 dBA measured at a distance of 1 m from the system when the system is in maximum cooling and 58 dBA measured at a distance of 1 m from the system when the system is in maintenance or warming.

Figure 11:
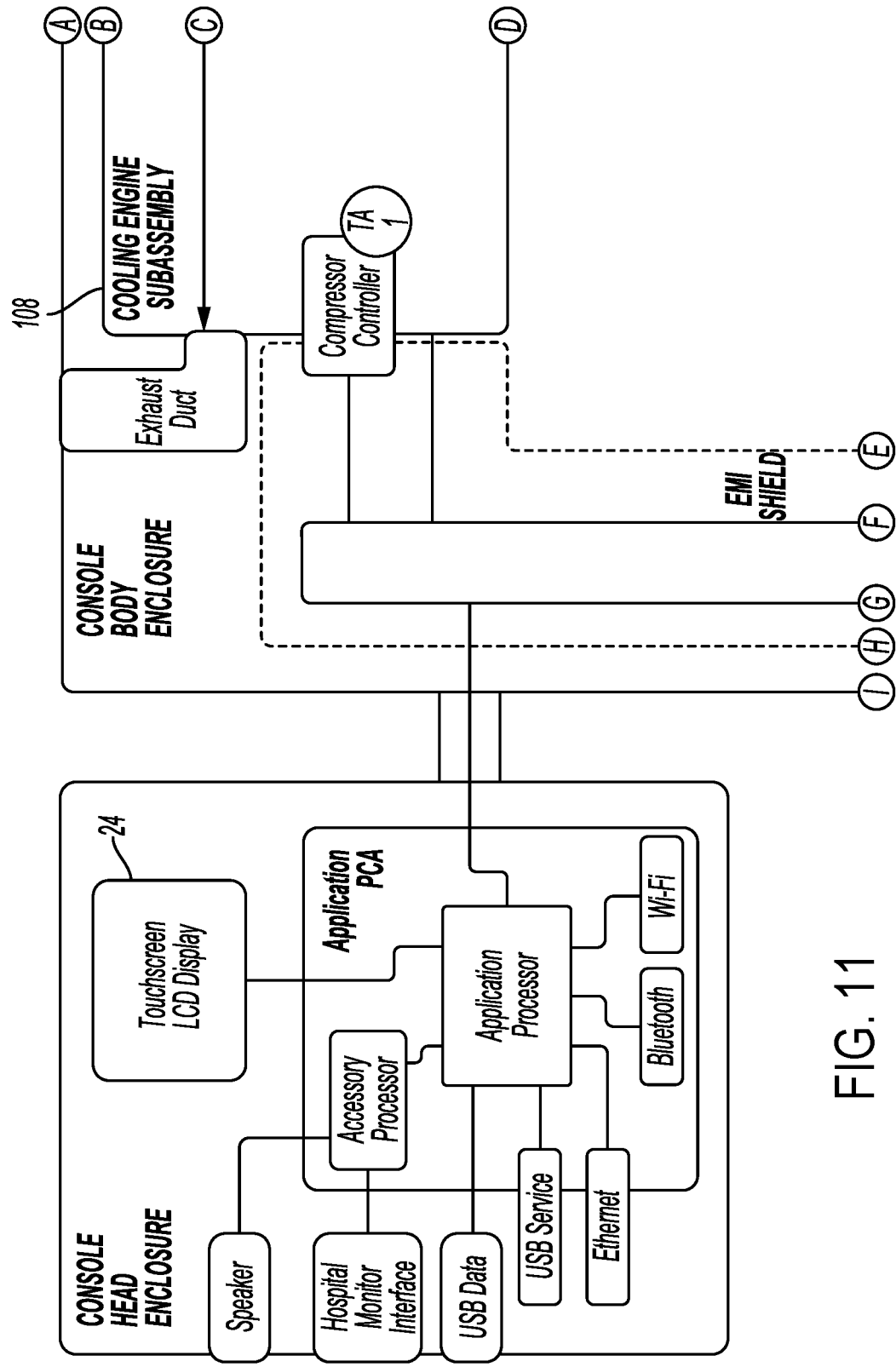
FIG. 11 is a schematic diagram of an endovascular heat exchange system.
Figure 11:
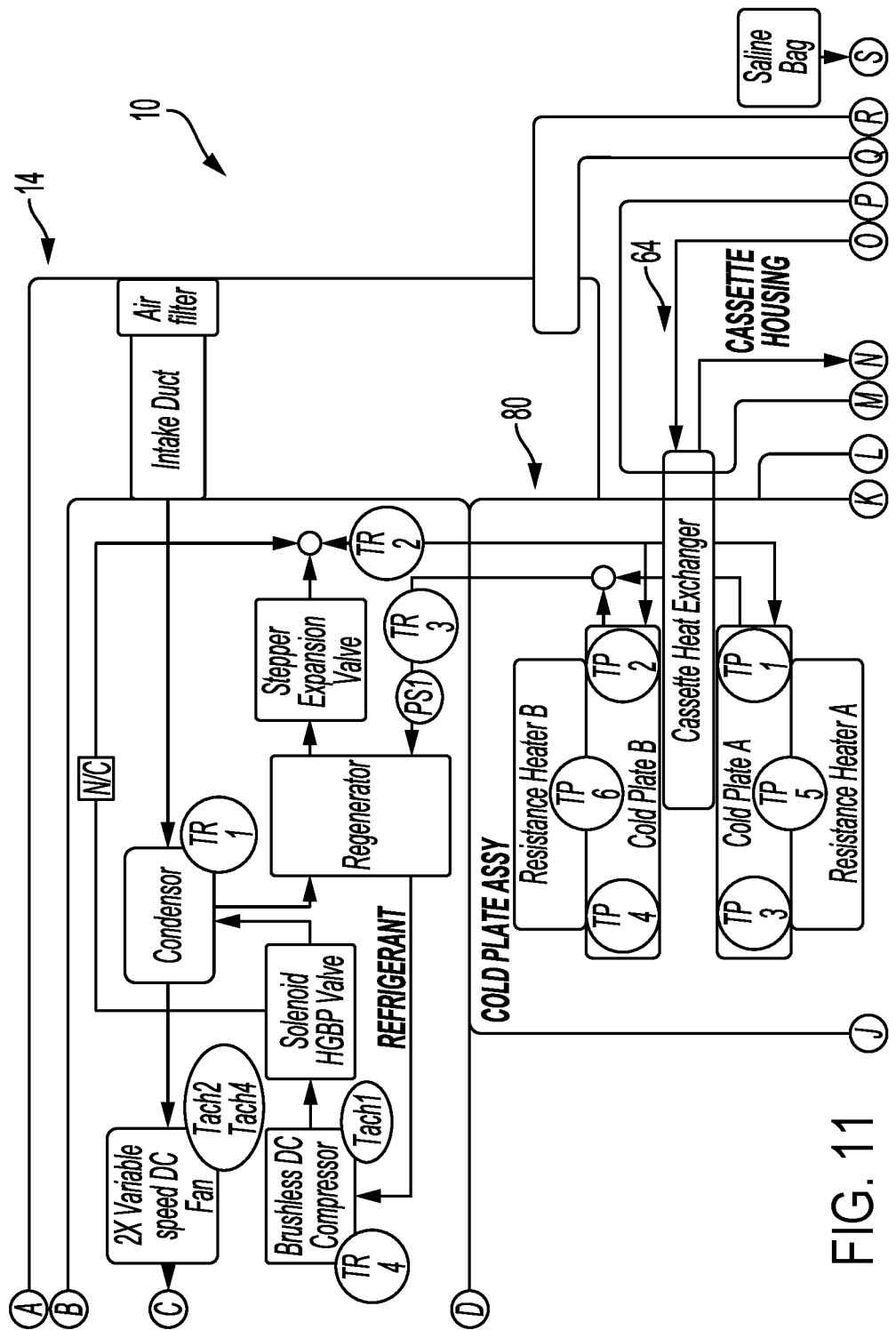
Figure 11:
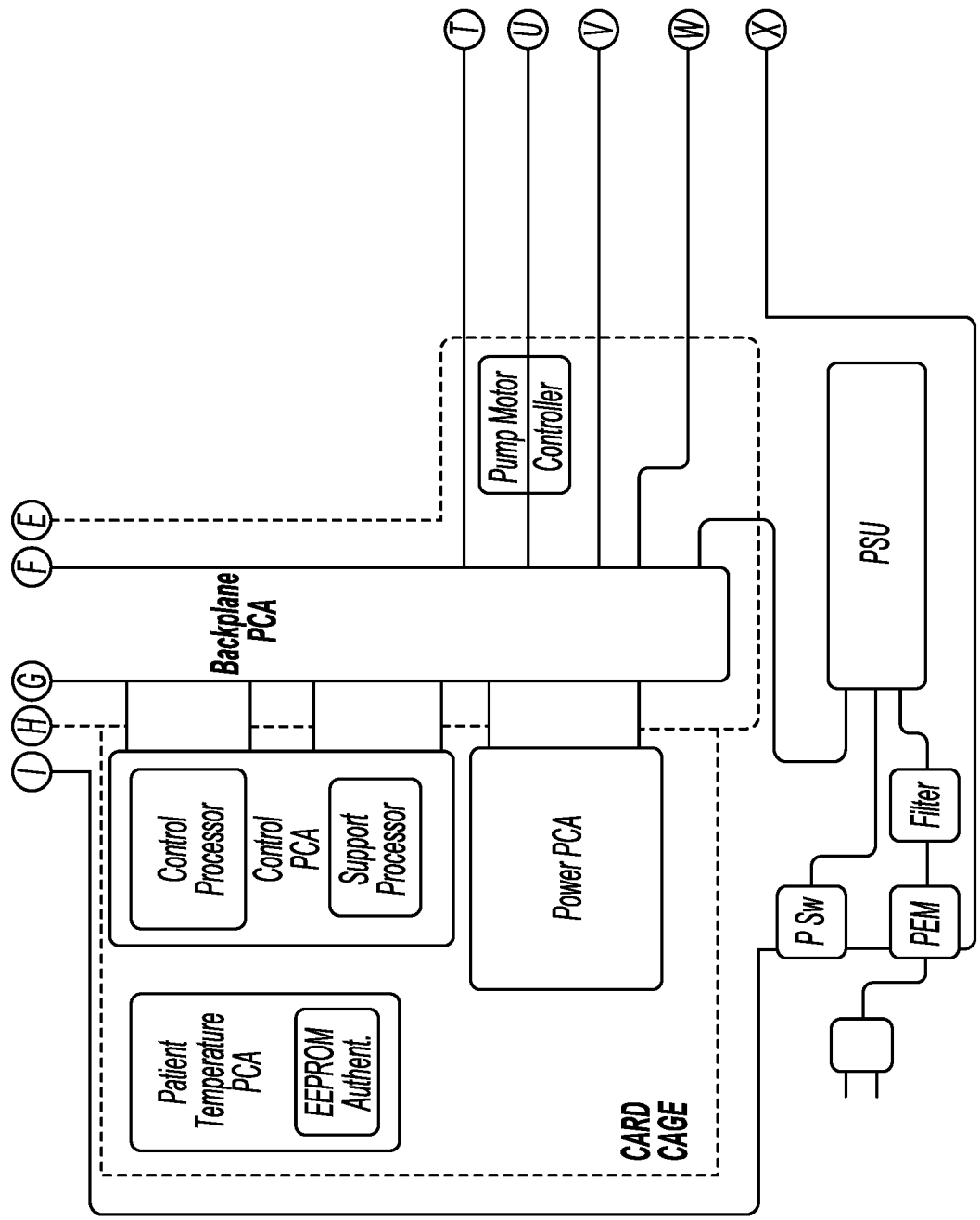
Figure 11:
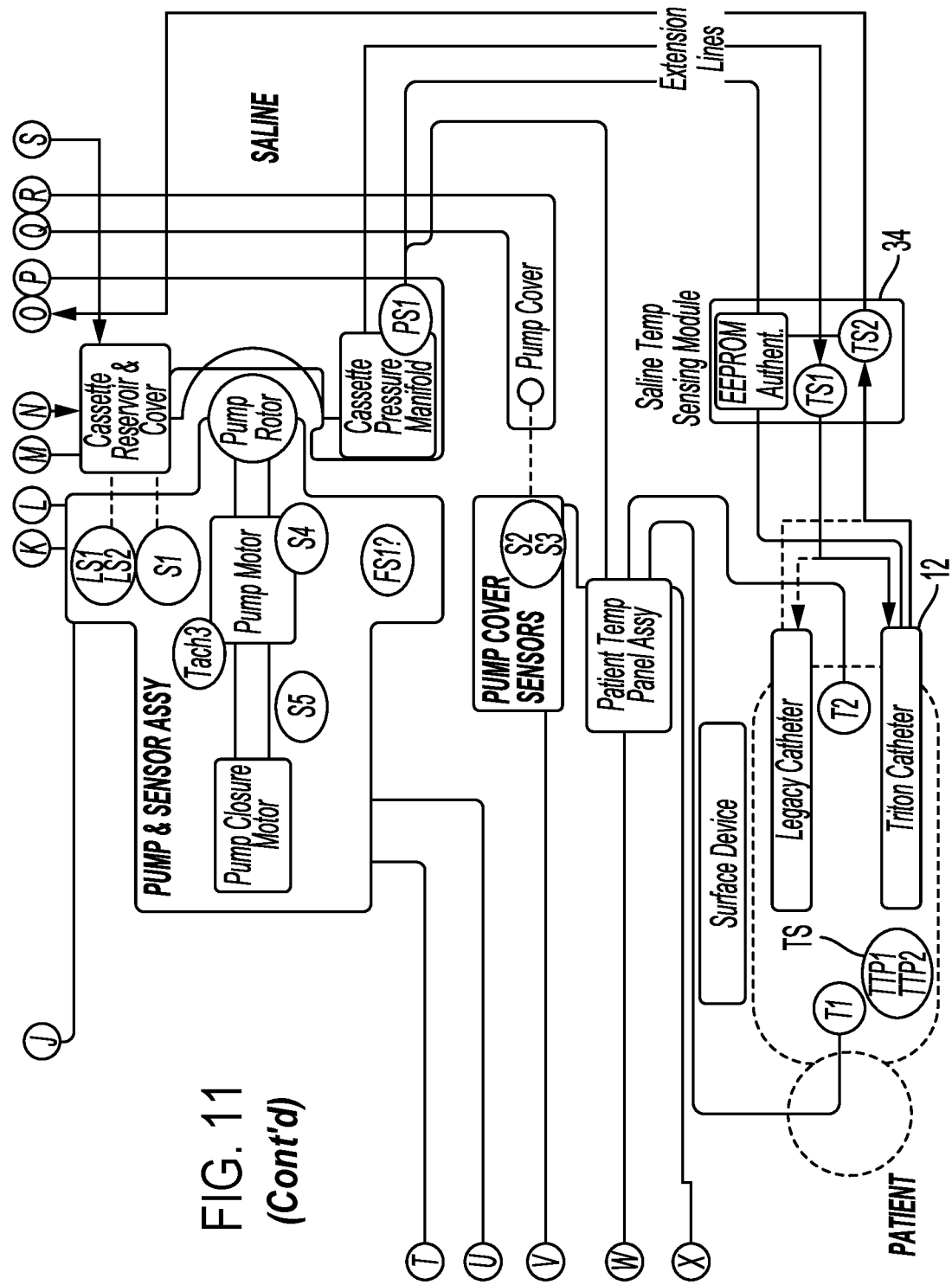

FIG. 11 is a schematic diagram of the endovascular heat exchange system 10. This schematic diagram shows major components of the system 10, including the console 14, heat exchange catheter 12, thermal exchange engine 108, console head/user interface 24, thermal exchange plates 80 and cassette 64. Additionally, this schematic diagram includes other components and functional indicators labeled according to the following legend:

FS FLOW, SALINE
FW FLOW, WATER
LS LEVEL, SALINE
LW LEVEL, WATER
PSR PRESSURE SWITCH, REFRIGERANT
PS PRESSURE, SALINE
S SWITCH
TACH TECHOMETER
TA TEMPERATURE, AIR
TR TEMPERATURE, REFRIGERANT
TP TEMPERATURE, PLATE
TS TEMPERATURE, SALINE
TW TEMPERATURE, WATER

To set up the system 10 a new tubing/cassette/sensor module assembly 60 or cassette assembly is obtained and removed from its packaging and the cassette 64 is unfolded to the opened and locked configuration. The access cover 42 of the control console 14 is opened. An "open" button is pressed on the touch screen user interface 24 causing the pump 70 to shift to its loading configuration. The cassette frame 69 and expandable vessel or bag 63 are inserted downwardly into the cassette receiving space 66 until the housing 62 abuts a front. The pump tubing is inserted within the pump raceway. The access cover 42 is then closed and a "close" button is depressed on user interface 24 causing the pump 70 to shift to the operative configuration. The user then presses a "prime" button on user interface 24 to prime the system with thermal exchange fluid from a bag or other container that has been hung on bracket 48 and connected to the system 10.

After the system has been primed, the catheter 12 is connected and inserted into the subject's body and the system 10 is operated to warm or cool the subject's body as desired.

Figure 12:
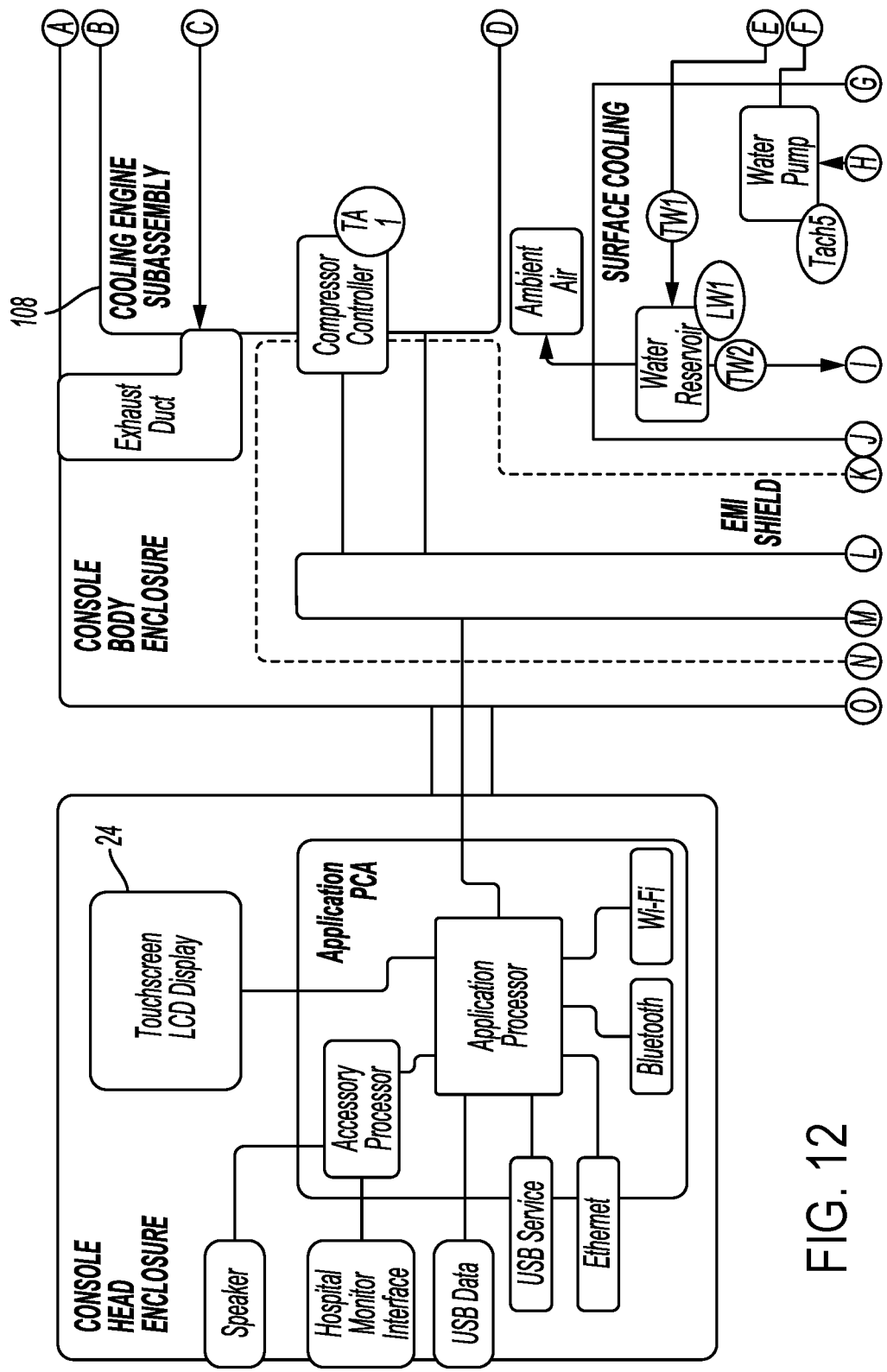
FIG. 12 is a schematic diagram of a heat exchange system capable of providing endovascular and/or body surface heat exchange.
Figure 12:
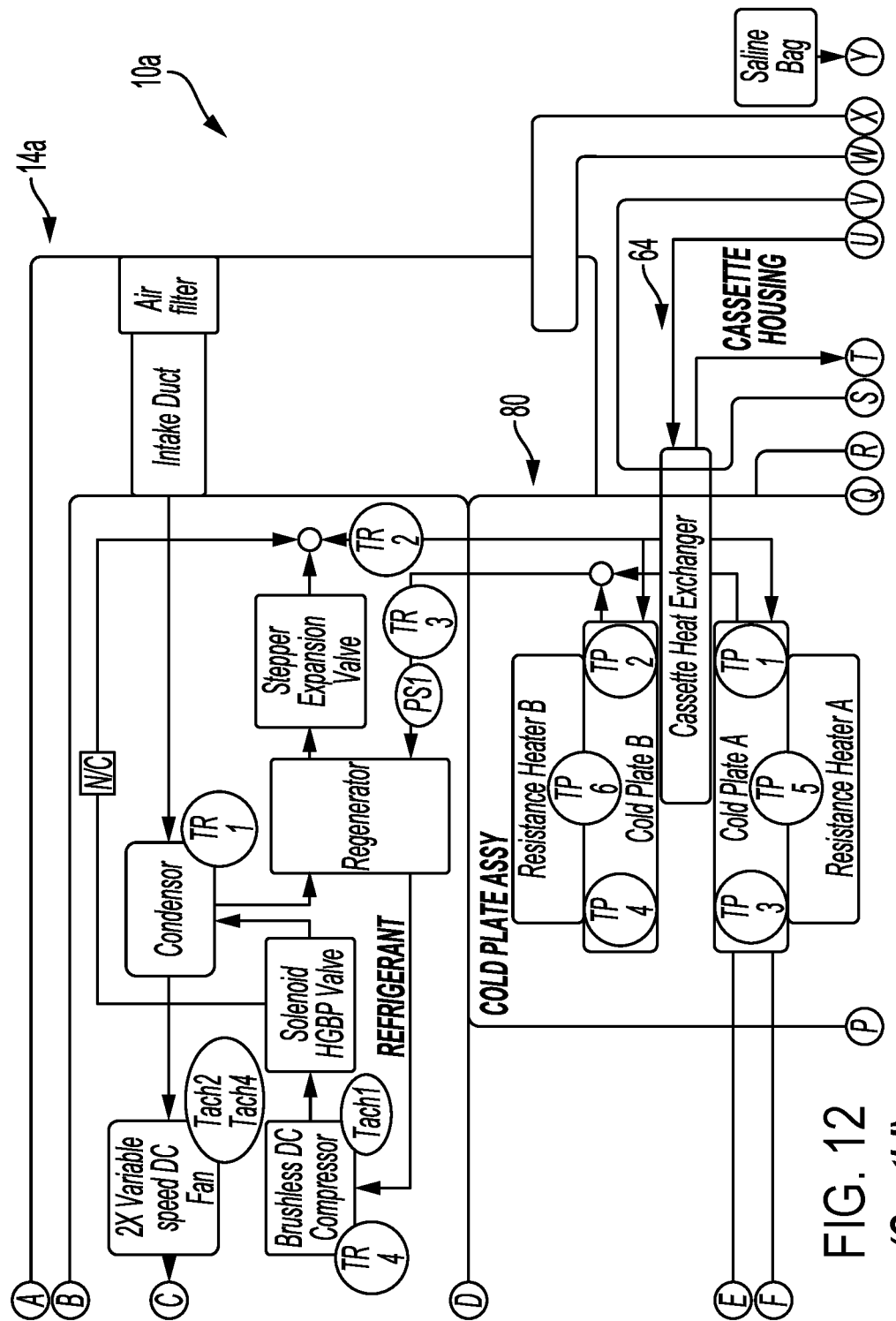
Figure 12:
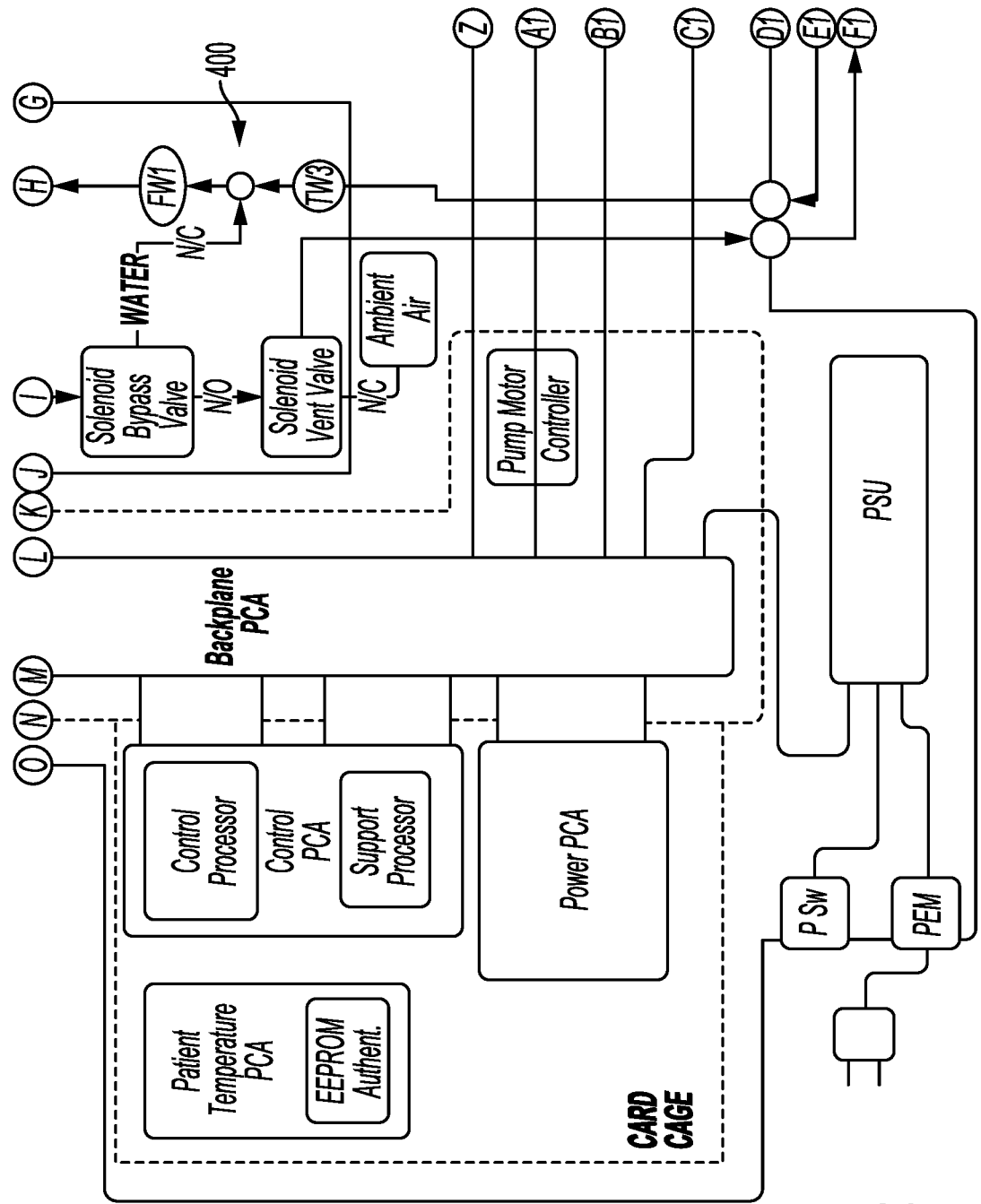
Figure 12:
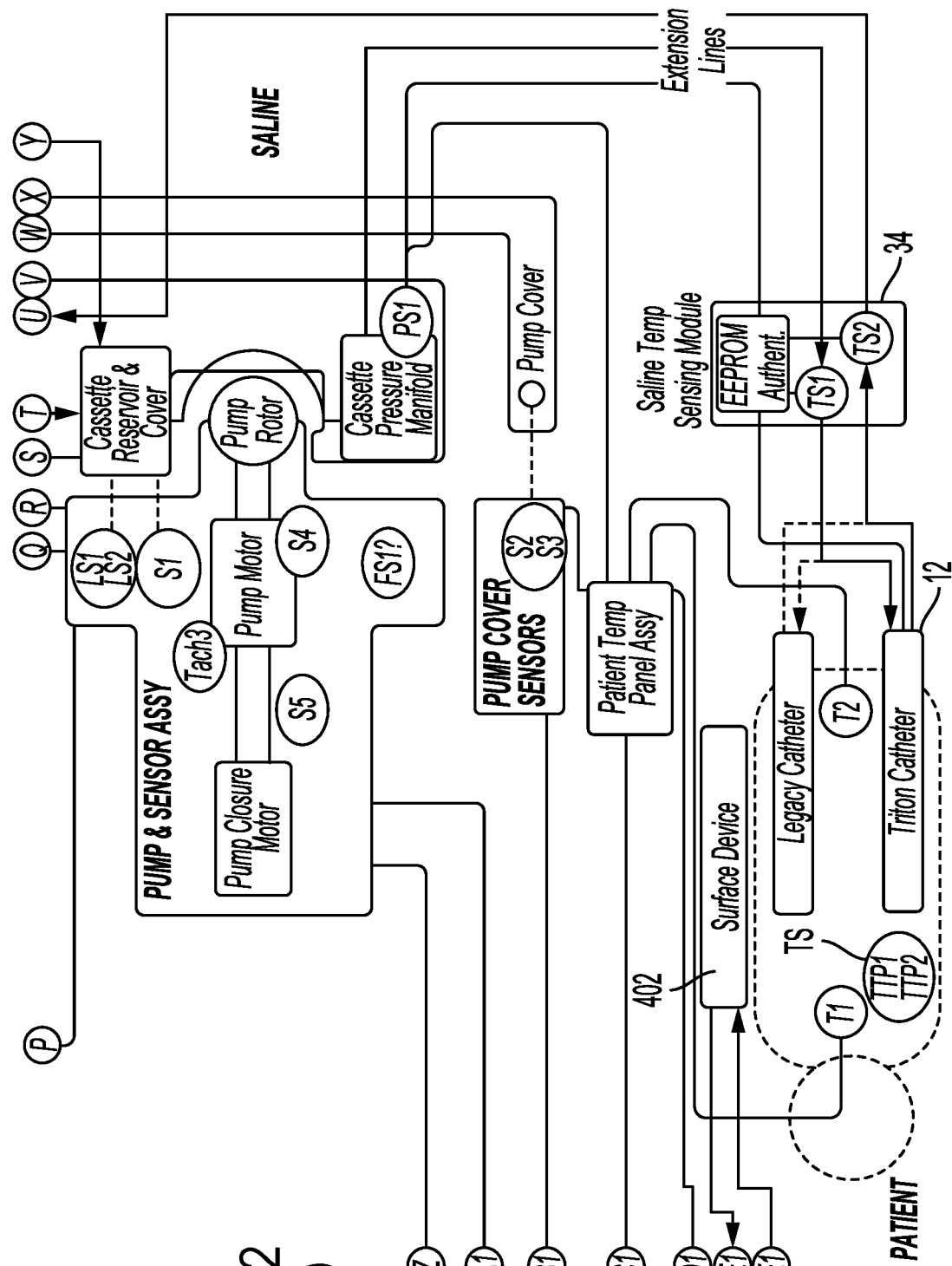

FIG. 12 is a schematic diagram of an example of a heat exchange system 10a capable of providing endovascular and/or body surface heat exchange. The system includes all of the elements described in the system 10 of FIG. 11 and, like FIG. 11, includes labeling according to the legend set forth above.

Additionally, this system 10a includes a body surface heat exchange fluid circuit 400 such that the system can provide body surface heat exchange by circulating warmed or cooled heat exchange fluid through at least one body surface heat exchanger 402, such as, for example, a heat exchange pad, blanket, garment, and the like. Such operation of the body surface heat exchange fluid circuit 400 and body surface heat exchanger 402 may be performed in addition to or instead of endovascular heat exchange. The body surface heat exchange fluid circuit includes a fluid reservoir, a pump, a bypass valve, a vent valve, thermal exchange plates and a body surface heat exchange device, e.g., a pad. A fluid, such as, for example, water, is added to the fluid reservoir. When the bypass valve is closed to the vent valve and open to the bypass line, fluid circulates from the pump, through the body surface fluid chambers in the thermal exchange plates, the reservoir, the bypass valve, and back into the pump. This allows the volume of fluid within the system to come to thermal equilibrium with the thermal exchange plates, which may be useful in preparing the device to deliver temperature management treatment to the patient. In normal operation, the bypass valve is open to the vent valve and the vent valve is closed, and fluid circulates from the pump, through the body surface fluid chambers in the thermal exchange plates, through the reservoir, bypass valve, and vent valve, to the body surface heat exchange device and then back through the pump. To drain the body surface heat exchange device, the vent valve is opened which allows air into the circuit and prevents fluid from flowing from the bypass valve. This forces fluid out of the body surface heat exchange device to the pump. The pump is a positive displacement pump capable of pumping air or liquid through the body surface fluid chambers in the thermal exchange plates, to the reservoir. The reservoir is open to ambient air (to allow excess air to escape the system if introduced by the draining process or normal operation, or to accommodate changes in fluid volume due to thermal expansion) and includes a fill port or drain. The circuit also includes body surface heat exchange fluid temperature sensors to provide feedback to the controller, and fluid temperature sensors and fluid flow sensors for use in power calculations.

In certain embodiments, one or more of the systems described herein may also include one or more physiological alarms and/or technical alarms. The physiological alarms may appear next to the patient's temp on the display screen, and may occur when the patient temperature exceeds the high or low patient temperature alarm value. Technical alarms may appear elsewhere on the display screen and may be triggered by console errors or other events, e.g., probe or catheter disconnection, saline loop overpressure, pump malfunction or open lid, and may be displayed by priority. Any of the alarms may be audible. The system may also transmit data, including patient and/or treatment data wirelessly, such as, for example, via Wifi, Bluetooth or other wireless connection. Data may also be transmitted via USB, Ethernet or wired connection. The system may be electrically powered or battery powered.

The endovascular temperature management system 10 described in various embodiments herein is a high-powered system, capable of rapidly cooling a patient.

In certain embodiments, the cassette/console is designed and configured such that it is capable of delivering less than or equal to 4 degrees centigrade working fluid or saline at a rate of greater or equal to 600 mL/min, at steady state, when up to 700 Watts (W) of heat is added to the working fluid or saline loop (e.g., heat added by the subject's body).

In certain embodiments, the cassette/console is designed and configured such that it is capable of delivering less than 4 degrees centigrade (C) working fluid or saline at a rate of 220+/−20 ml/min, at steady state, when less than or equal to 70 W of heat is added to the working fluid or saline loop (e.g., heat added by the subject's body).

In certain embodiments, the cassette/console is designed and configured such that it is capable of delivering greater than or equal to 42 degrees C. working fluid or saline at a rate of >400 mL/min, at steady state, when up to 200 W of heat is removed from the working fluid or saline loop.

In certain embodiments, the system (cassette, console, and catheter) is designed and configured such that it is capable of delivering greater than 400 Watts, or greater than or equal to 500 Watts, or greater than or equal to 600 Watts of cooling power, e.g., with less than or equal to 4 degrees C. working fluid or saline at a catheter pressure of about 60 PSI. In certain embodiments, the system may deliver from 500 to 700 W or 600 to 700 W of cooling power or about 675 W of cooling power or greater than 700 W of cooling power.

In certain embodiments, the system (cassette, console, and catheter) is designed and configured such that it is capable of delivering greater than or equal to 50 W of warming power e.g., with greater than 7 degrees C. working fluid or saline at a catheter pressure of about 40 PSI.

In certain embodiments, the system performance parameters were verified during a bench test. The bench test included placing a catheter (which is connected to a console/cassette assembly) in a rigid 22 mm ID tube, which simulates the average IVC (inferior vena cava) diameter, through which water at a temperature of 37 degrees C. is flowing at a rate of 2.5 liters per minute (simulating blood flow) over the catheter in a direction from the proximal end of the catheter to the distal end of the catheter.

In certain embodiments, in maintenance and controlled rate warming, the system may control a stable patient's temperature, as measured by console, within about 0.3 degrees C. of target when using a temperature sensor or probe on or in the catheter. During normal use and in the case of a sudden saline loop blockage, the system shall regulate and limit working fluid or saline pressure for catheters as follows: <20 C: 60 psi nominal, 90 psi limit; >=20 C: 40 psi nominal, 70 psi limit; or 40 psi nominal, 70 psi limit. The console working fluid pump and cassette shall be capable of an output up to 600 mL/min at 70 psi. Saline or working fluid pressure at the outlet of the saline pump may be measured, e.g., over a range of 0-100 psi with an accuracy of +/−5 psi over the range 10-70 psi. The system may be used concurrently with a defibrillator, electro surgical unit or other device or during an MM. The console and cassette together may be capable of delivering less than 8 degrees C. saline, at a rate of greater than or equal to 600 mL/min, within 5 minutes of turning on the console, when starting with the system equilibrated to ambient temperature. The console and cassette together may be capable of changing the temperature from 4 degrees C. to 40 degrees C. within 10 minutes.

In some embodiments of the system 10, the controller/processor(s) may be programmed to vary not only the temperature of the heat exchange fluid being circulated through the heat exchange catheter 12, but also the rate and/or frequency of such flow. One non-limiting example of this is shown in the flow diagram of FIG. 13. In this example, after the subject has reached the target temperature and the system 10 is operating to maintain the body temperature at or within a permissible variance range of the target temperature, the system 10 holds the temperature of the heat exchange fluid constant and varies the speed of the pump 70 to adjust the flow rate of heat exchange fluid through the catheter 12 as needed to maintain the body temperature. The controller monitors the pump speed. If the pump speed exceeds a predetermined limit, the controller will then cause warming or cooling of the thermal exchange plates 80 to adjust the temperature of the heat exchange fluid as needed to reduce the pump speed to the predetermined limit. This allows for optimal combination of flow rate and temperature adjustment during the maintenance phase of a treatment session. It is to be understood that this applies only so long as the system is continuing to cool or continuing to warm in order to maintain the body temperature. If it becomes necessary for the system to switch from cooling to warming or from warming to cooling, the controller will adjust the temperature of the heat exchange fluid irrespective of whether the pump speed has exceeded the limit.

For example, after the system 10 has cooled a subject to a target body temperature of 32 degrees C., the subject's body may tend to rewarm. Thus, the system will operate in cooling mode to maintain the target body temperature against the body's inherent tendency to rewarm. In doing so, the system will maintain a constant temperature of heat exchange fluid and will vary the speed of the pump 70 as needed to maintain the target body temperature. However, if it becomes necessary for the pump 70 to run at a speed that exceeds a predetermined limit, the controller will cause the cooling engine 108 to reduce the temperature of the heat exchange fluid by an amount which will allow the pump to slow to a predetermined limit while still maintaining the target body temperature.

The heat exchange catheter system 10 may incorporate pressure sensor(s) for sensing the pressure of the circulating heat exchange fluid. During a given treatment session, over-pressurization events can occur. This is when the saline pressure is above the saline pressure predetermined limit. Such over-pressurization events are typically of a transient nature and result from temporary compression or bending of the catheter 12 or associated tubing, or other causes. During a given treatment session, under-pressurization events can also occur. Such under-pressurization events occur when the Saline Pump Maximum Set Point (SPM_set) is reached, meaning the saline pump is not allowed to move any faster, but the saline pressure is below the saline pressure predetermined limit. When an over-pressurization or under-pressurization event of significant magnitude occurs, it may be desirable to adjust SPM_set. However, it is preferable not to abruptly change or overly reduce/increase the pump speed. Additionally, after a transient over-pressurization or under-pressurization event has past, it is desirable to return the speed of the pump 70 to optimal operating speeds to maintain normal pressurization of the circulating heat exchange fluid.

Figure 14:
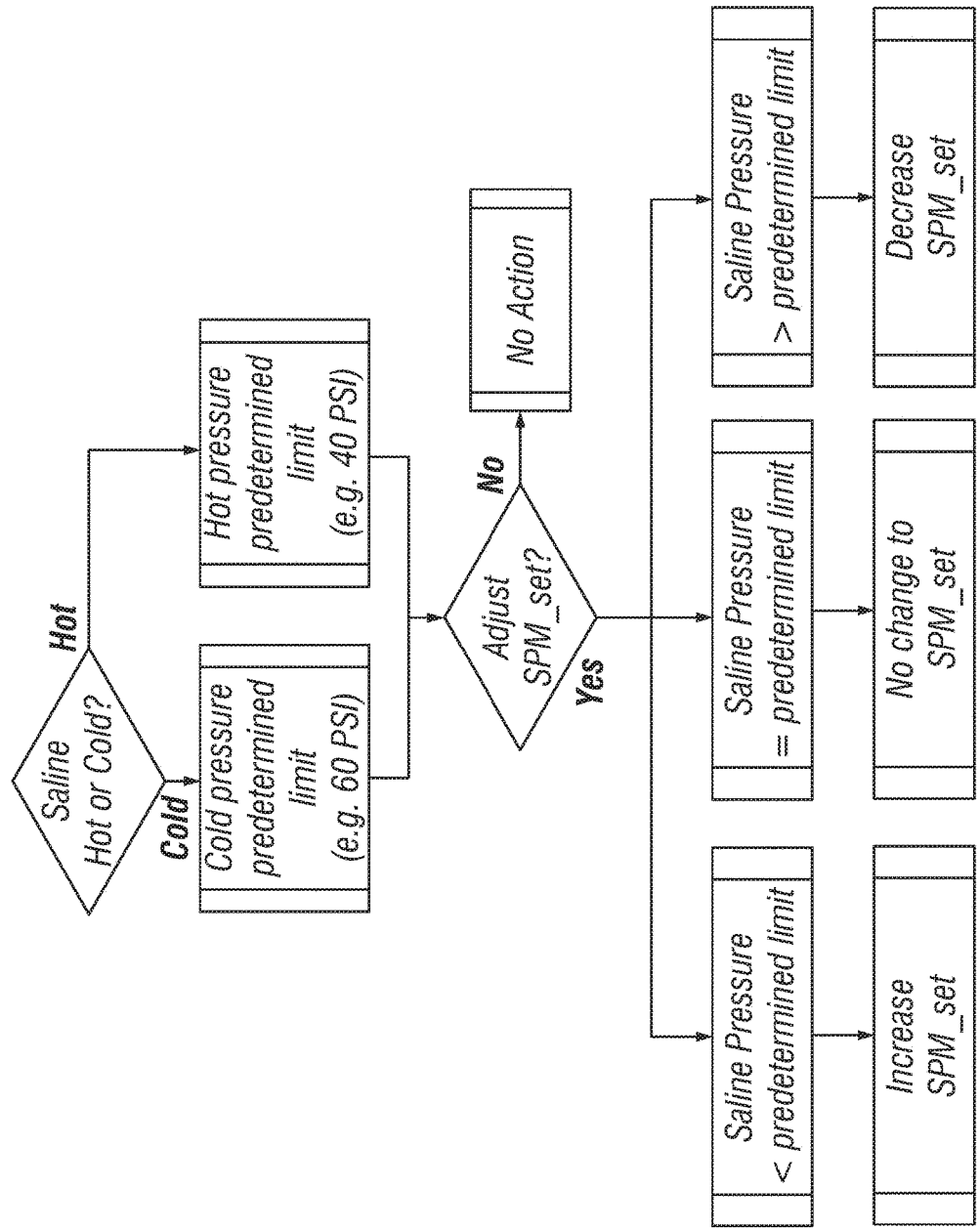
FIG. 14 is a flow diagram showing one example of a process by which a body heat exchange system may optimize pump speed and heat exchange fluid pressure during operation with either warm or cool heat exchange fluid.

FIG. 14 is a flow diagram illustrating the SPM_set adjustment protocol that some embodiments of the system 10 may be programmed to perform. The system 10 is equipped to sense the temperature of the heat exchange fluid, and the heat exchange fluid is classified as "cold" or "hot". In this non-limiting example, the predetermined limit for "cold" heat exchange fluid is set at 60 pounds per square inch (psi) and the predetermined limit for "hot" heat exchange fluid is set at 40 psi. The SPM_set will only be adjusted if the saline pressure is above the predetermined limit or the saline pump set point is equal to SPM_set. The controller will cause the SPM_set to decrease if the saline pressure is above the pressure predetermined limit, and will cause the SPM_set to increase as the saline pressure is below the pressure predetermined limit. There may be a maximum and minimum limit of the SPM_set, and the SPM_set cannot exceed those limits (e.g., max of 100% and min of 10%).

Optionally, the controller/processor(s) may also be programmed to store the most recent SPM_set for "cold" and "hot" heat exchange fluids. Thus, when the saline temperature threshold is crossed, the system 10 will switch from "cold" mode to "hot" mode, or vice versa, and upon doing so may recall and apply the recently calculated SPM_set setting for that temperature. In this example, the SPM_set adjustment protocol repeats every three seconds, however other intervals could alternatively be used.

The heat exchange system described above may be modified so that it may be powered by one or more batteries, allowing the system to be operated during transport and/or transported to and operated at a location where a source of alternating current may not be available. Further, the various embodiments and examples of such a battery powered heat exchange system may be configured to automatically provide direct current from the one or more batteries in the event that the heat exchanger, while connected to an alternating current source, experiences a loss of alternating current power.

Battery or rechargeable battery may refer to one or more batteries or rechargeable batteries; unless a person of ordinary skill would understand that a specific example is referring to a single battery, battery cell, rechargeable battery, non-rechargeable or rechargeable battery cell. In one or more of the embodiments described herein, a rechargeable battery and/or battery may be utilized.

Various types of batteries or rechargeable batteries, such as, for example, ones using lead-acid, nickel-cadmium and lithium-ion cells and the like can be used to power the portable heat exchange system described herein. While any of the above rechargeable battery types may be used, it is advantageous to utilize a battery chemistry that results in a battery having a very low total internal resistance to ensure extended and reliable operation of the battery when the battery is under a constant power drain. One such battery chemistry having a low internal resistance is lithium-ion chemistry.

The various embodiments set forth below, along with the accompanying drawings, describe a transportable battery system in the context of using three lithium-ion batteries. It will be understood that the embodiments shown and described are exemplary, and systems utilizing only one battery, and systems that utilize more than three batteries, or systems employing one or more batteries using different battery chemistry, are contemplated to be used, and such use does not depart from the intended scope of the disclosed heat exchange system.

While lithium-ion (Li-Ion) batteries are capable of providing the voltage and current required to operate the heat exchange system described for extended periods, care must be taken during both the discharge, and recharge, of Li-Ion batteries to ensure that the batteries continue to function for their desired lifetimes. For example, it is well known that Li-Ion battery cells should not be over-charged, nor should they be over-discharged. One exemplary system for monitoring the charging and recharging of such batteries is described in U.S. Pat. No. 9,099,877, which is incorporated herein in its entirety.

Examples of Li-Ion batteries suitable for powering the system are the Autopulse (AP) 100S battery, model number 8700-0752-01, and the AP NXT battery. The AP 100S battery includes 11 cells (A123 System ANR26650), and provides 36.3 volts at 2.5 Amp-hours, or 90.97 Watt-hours. The AP 100S dimensions are 29.2 centimeters (cm) in length×8.1 cm in width×5.7 cm high (11.5"×3.2"×2.2") and weighs approximately 3.0 pounds (1.4 kilograms). The AP Next battery has 12 cells (A123 System ANR26650), providing 39.6 volts at 2.5 Amp-hours and 99 Watt-hours. The AP NXT dimensions are 214 centimeters (cm) in length×135 cm in width×61 cm high (11.5"×3.2"×2.2") and weighs approximately 3.0 pounds (1.4 kilograms).

In certain embodiments, a rechargeable battery may have a height dimension of 2.3" or 2.4", a width dimension of 3.2" or 8.5", and a length dimension of 11.5" or 5.4".

As will be described in more detail below, the batteries are inserted into a battery receiver or case that mounts onto a housing of the system. Alternatively, the batteries may be mounted directly onto a housing of the system without a receiver or case. In one or more embodiments, the receiver or case is sized to receive a battery having the dimensions of one of the batteries described above. Such sizing is advantageous in that it assists in ensuring that that a proper battery is used to power the system. Moreover, the connections or terminals of the batteries may be configured so that only the proper battery may be connected to the electronics of the system. Such connections helps to ensure that an improper or counterfeit battery is not used to try to power the system, and such a battery could cause damage to the electronics of the system, rendering the system inoperable or incapable of operating the system long enough to provide proper treatment while a patient is being transported.

The batteries described above are capable of providing enough power to continue to cool a patient at maximum cooling while the patient is being transported. For example, such a battery needs to be able to store enough energy so that it can continue to operate the system to provide maximum cooling in the range of 400-700 watts of cooling power during a transport lasting up to 20 minutes, and at times, as long as 30 minutes. In other embodiments, the battery should provide enough energy to power the heat exchange system in maintenance mode to provide at least 200 watts of cooling power for times that may extend beyond 30 minutes.

In other embodiments, the rechargeable battery may be capable of storing enough energy to run the system so that the heater/cooler may provide at least 150 watts for at least 10 minutes. In another embodiment, the rechargeable battery is capable of powering the system so that the system may provide at least 50 watts of cooling power, or 150-700 watts of cooling power for at least 10 minutes, e.g., for 10 to 90 minutes, or 400-700 watts of cooling power for at least 10 minutes, e.g., for 10 to 90 minutes, or 600-700 watts of cooling power for at least 10 minutes, e.g., for 10 to 90 minutes. In other embodiments, the rechargeable battery is capable of powering the system to provide maximum cooling power for at a period of time in the range of 10-20 minutes.

In some embodiments, the batteries are designed to be inserted into, and received by, the bays of a battery receiver or tray, and remain in place during an entire treatment of a patient. In some instances, however, it may become necessary to replace a faulty rechargeable battery during treatment of a patient, a process called hot-swapping. As will be discussed below, the transport battery process may adjust the current being drawn from each remaining battery to adjust for the loss of the faulty battery, and re-adjust operation of the system when a replacement battery has been installed.

Figure 15A:
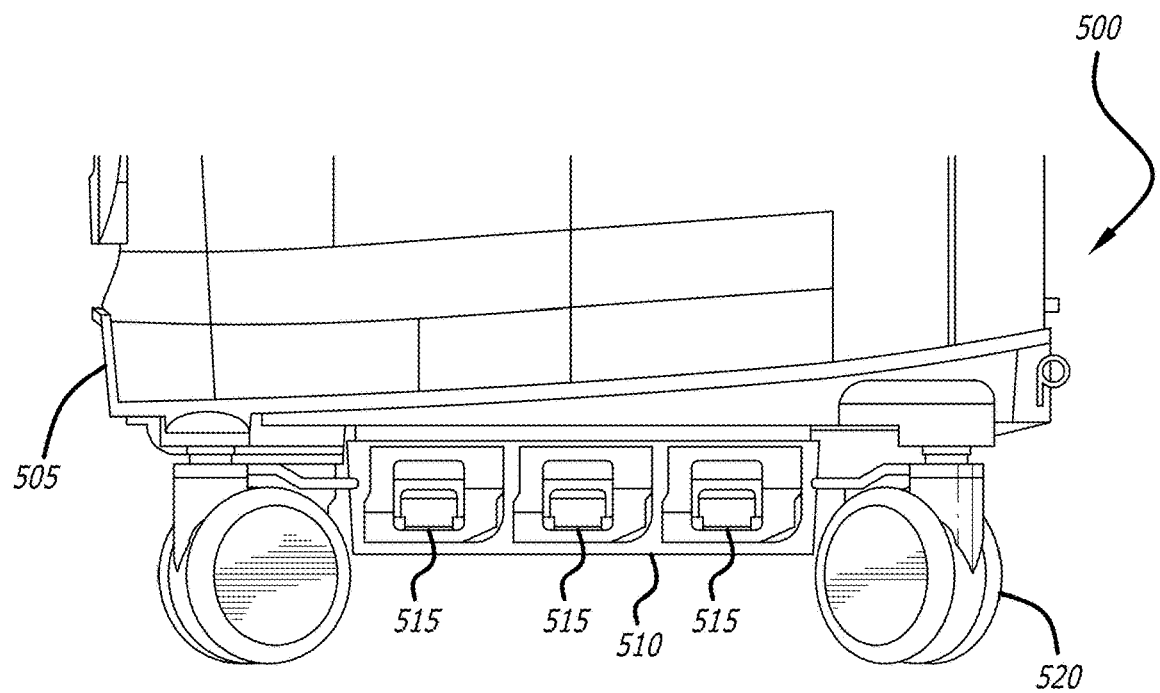
FIG. 15A is a side view of a lower portion of an embodiment of a transportable endovascular heat exchange system configured to be powered using both alternating current and direct current provided by one or more removable batteries.
Figure 15B:
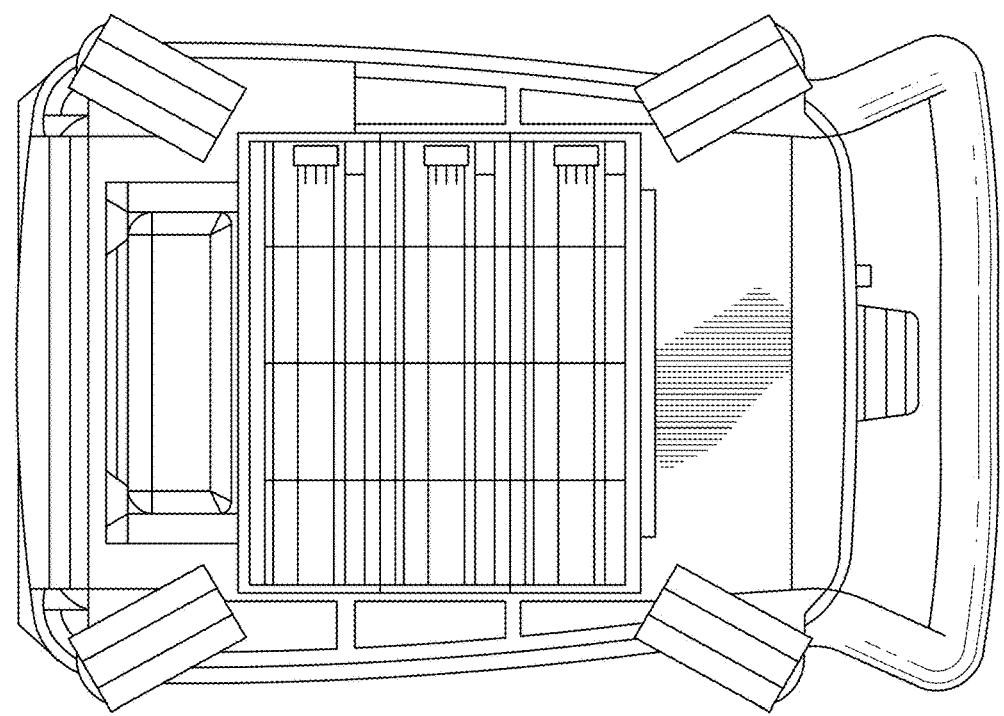
FIG. 15B is bottom view of the transportable heat exchange system of FIG. 15A.

Referring now to FIGS. 15A and 15B, a battery receiver or tray 510 configured to receive and hold one or more batteries 515 is mounted to a bottom surface of housing 505 of an embodiment of the endovascular heat exchange system 500 described above. Also shown are a number of wheels 520 mounted on the bottom of the housing. It will be understood that the details or design of the housing 505 and the receiver 510 may be changed or re-configured as needed. For example, the housing and included components may re-configured to provide a compact system amendable to transport by medical personnel.

Figure 16:
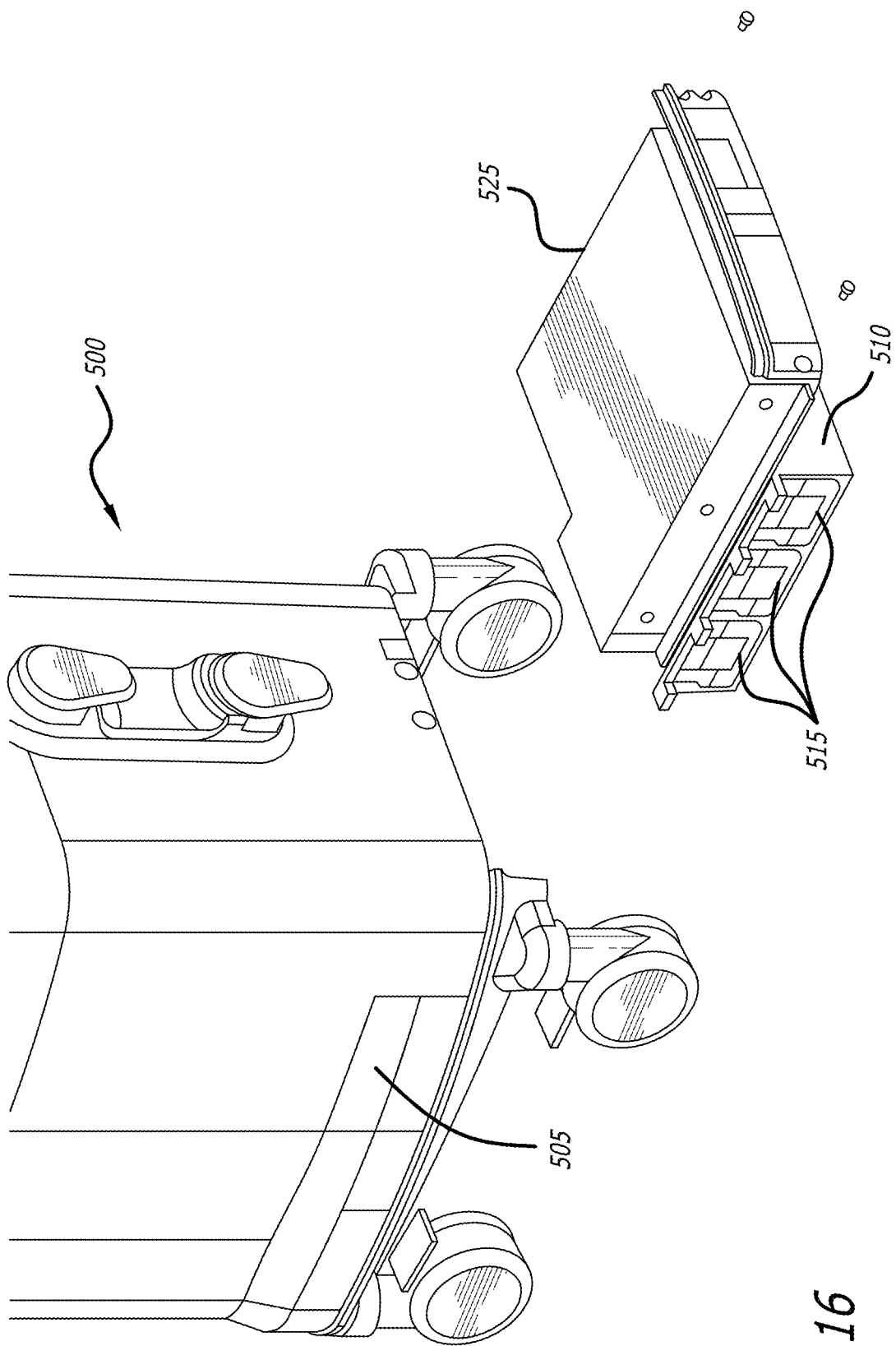
FIG. 16 is a perspective view of an embodiment of the transportable heat exchange system of FIGS. 15A and 15B showing a removable battery management system and batteries configured to slide in and out of the bottom of the transportable heat exchange system.

FIG. 16 illustrates an embodiment of the system 500 showing the battery receiver or tray 510 mounted to a bottom surface of a battery management system and/or power supply unit 525. The battery receiver 510 may be mounted to a bottom surface of the battery management system or power supply unit, e.g., with screws, latches, clamps or other fasteners. The assembly may be mounted to the heat exchange system in a manner that allows for sufficient clearance from the ground, to avoid contact with the ground and damage to the batteries resulting therefrom. In this embodiment, the power supply unit (PSU) 525 includes rails (not shown) that may be received within a track system (not shown) mounted to the bottom of the housing 505. This allows the receiver/PSU assembly to be removably mounted to the housing 505 by engaging the rails of the receiver/PSU assembly with the track system of the housing to hold the receiver/PSU assembly in place. Suitable additional hardware features may be included in either the receiver/PSU assembly or the track system of the housing to ensure that the system 500 may be moved without dislodging the receiver/PSU assembly from the housing. Those skilled in the art will understand that the rail/track mounting system described is only one possible embodiment, and that other mounting and locking systems may be used and are contemplated to be within the scope of the presently disclosed heat exchange system.

Individual batteries may be removed from the receiver while the receiver and power supply unit are mounted to the housing. The battery bays or slots may be accessible via an opening or openings located on the same or different sides of a receiver. Optionally, the power supply and receiver with batteries may be removed. The receiver may be detached from the power supply after or before the assembly is removed from the console/housing.

In another embodiment, a battery may be configured to be part of or integral to the system console or battery receiver and only be removed after the battery receiver is first removed from the housing. In such an embodiment, the battery may be fully charged and shipped together with the heat exchange system. For example, a battery with a capacity up to 100 Watt-hour may be fully charged and shipped while in the heat exchange system using various shipping methods including airfreight, whereas the same battery may need to be fully discharged if shipped by itself. A heat exchange system may be shipped with a charged battery and be able to power on immediately, and/or the charged battery may provide power during transportation of the console, e.g., in an ambulance, and for monitoring specific parameters. In some embodiments, an additional battery or batteries may be added when the shipped system arrives at its destination.

The battery receiver 510 may be formed of a durable material, such as, for example, sheet metal or durable plastic, such as, for example, a fiber filled plastic material. Moreover, while the receiver is depicted as being a unitary structure having one or more bays to hold the batteries, each bay could be an individual structure, with each bay separated from an abutting bay by the walls of the individual structure and/or each bay individually removable from the system. In other embodiments, such as in the illustrated unitary structure, each bay may be separated by a wall to isolate each battery from an abutting battery.

In some embodiments, each of the cells of the Li-Ion battery may be contained in a housing that is configured to include all of the electronics, circuits and/or processors needed to manage charging, discharging, over-charge protection, and over-current protection of the battery. Other circuits, such as those disclosed in U.S. Pat. No. 9,099,877, incorporated herein in its entirety, may also be contained in the battery housing.

In one embodiment, all of the circuits and processors needed to operate and manage the functions related to the battery or batteries may be disposed in the PSU assembly 525. Where this is the case, such circuitry, either in whole or in part, may be omitted from the housing of the battery, since it would be redundant. In another embodiment, some of the circuits used to operate and manage the battery may be included in the receiver/525, and others may be enclosed in the battery housing.

Figure 17:
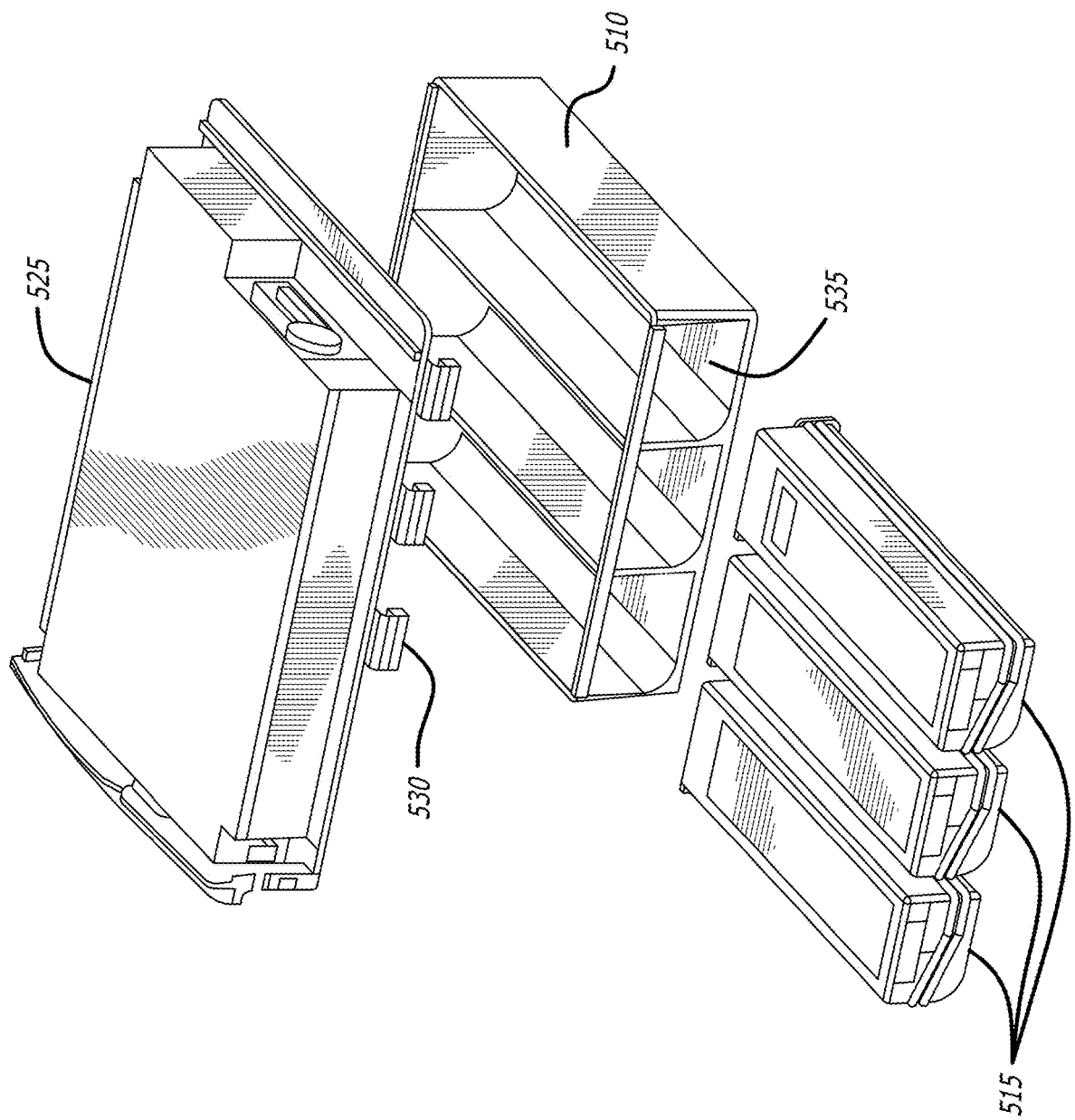
FIG. 17 is an exploded top perspective view of one embodiment of a removable battery management system.
Figure 22:
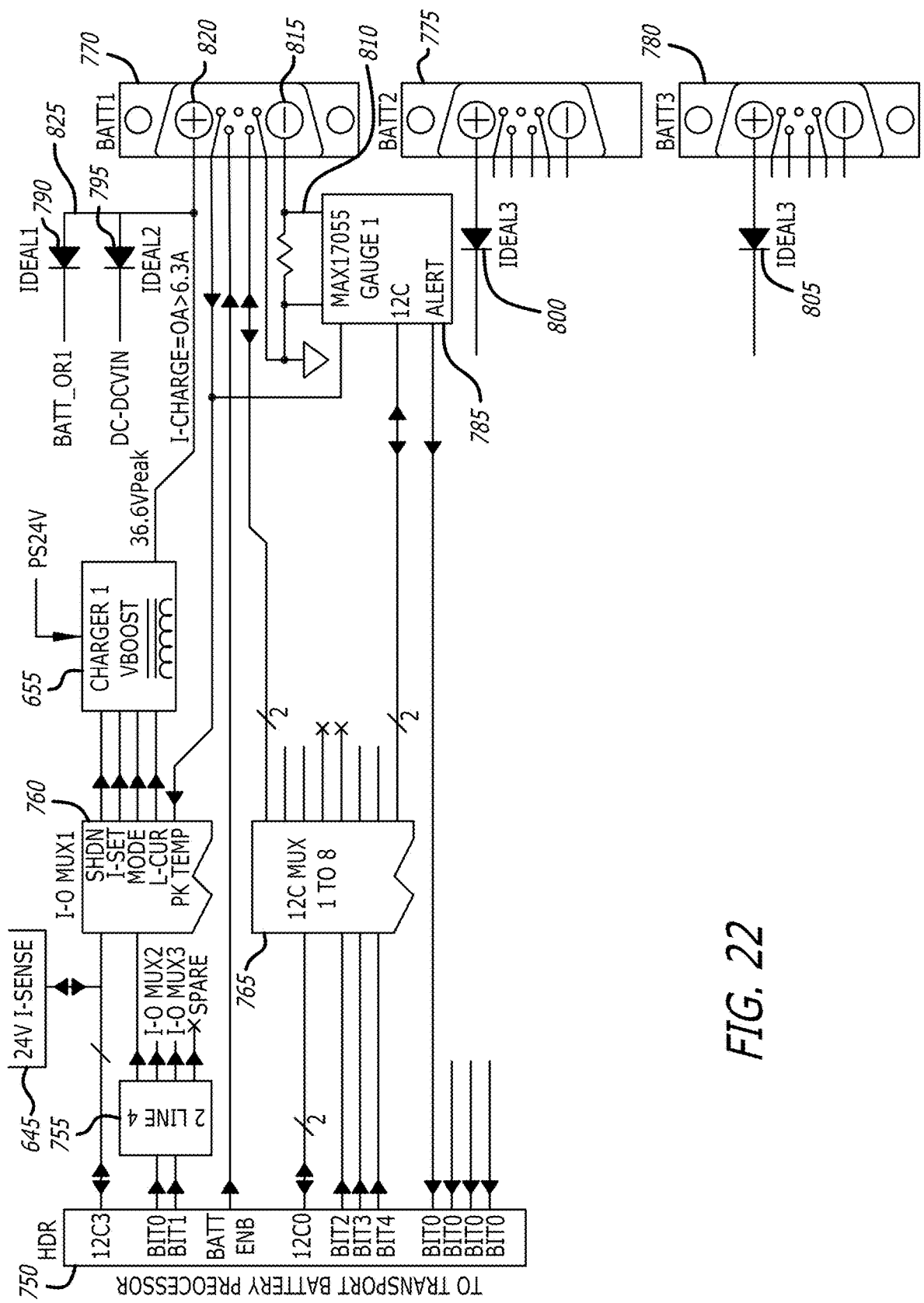
FIG. 22 is a schematic diagram of an embodiment of a charging circuit for charging and resynchronizing a rechargeable battery.

FIG. 17 is an exploded view of an embodiment of the receiver/PSU assembly of FIG. 16 illustrating the cooperation of the receiver 510 and the battery management system or PSU 525. Also depicted is one example showing three rechargeable batteries 515 that are configured for insertion into the receiver 510. In this exemplary embodiment each of the three batteries shown may be inserted into its own bay 535. Various mechanisms or systems may be utilized to lock the inserted battery into the bay (e.g., a latch, clamp or other restraining or holding mechanism), and also provide electrical connectors that engage with electrical connectors of the battery when the battery is inserted into the bay. An example of one type of connector that may be used is shown in FIG. 22 used to connect the batteries to their charging circuits. Depending on the number of lines that need to be connected, other types of terminal connectors or line connectors may be used. Alternatively, connectors that are custom configured to connect the battery or batteries to the system may be used, such male and female types configured to be connected to one and another in a manner that ensures that the various systems, and the batteries, are connected properly.

Also shown in FIG. 17 are flex circuits 530 used to engage connectors of the battery to provide electronic connection and communication between one or more processors or computers that are used to operate the exemplary heat exchange system. In some embodiments, the flex circuits 530 may be configured to connect to a connector or connectors disposed on or in a surface of the battery receiver or tray 510. As shown above, the heat exchange system 500 may include one or more processors that control the operation of the heat exchange system, and may also be configured to communicate with one or more processors included within a battery housing which are used to control the operation of the battery.

In some embodiments, each battery, or housing enclosing a battery, may include a connector or connectors for connecting the battery to the heat exchange system. Such connectors may include a positive and negative terminal, as well as terminals for connection of various communication lines to corresponding lines in the heat exchange system. In some embodiments, such connectors may be configured to engage appropriate connectors mounted in or on a surface of the bay, so that inserting the battery into the bay results in engagement of the battery connector or connectors to the bay connector or connectors. A battery that lacks the correct configuration of connector or connectors will not be able to connect to the system, even if the battery is physically capable of being inserted into the bay.

Figure 18:
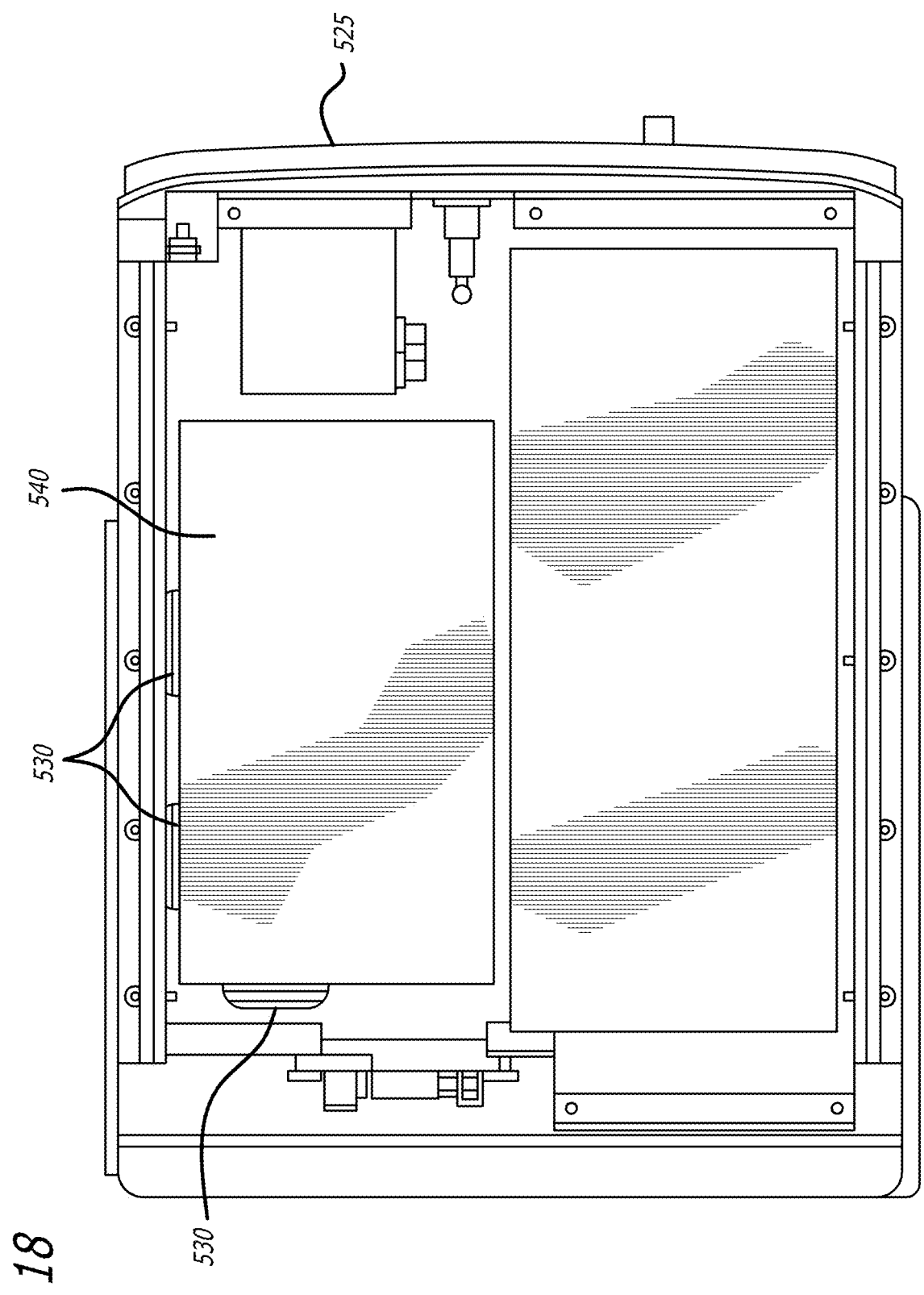
FIG. 18 is a top view of an embodiment of a battery management system tray.

FIG. 18 is a top view of an exemplary embodiment of the PSU 525 illustrating the connection of flex circuits 530 with battery PCA board 540 to provide power and/or communications between the one or more batteries and the remainder of the systems of the heat exchange system.

Figure 19:
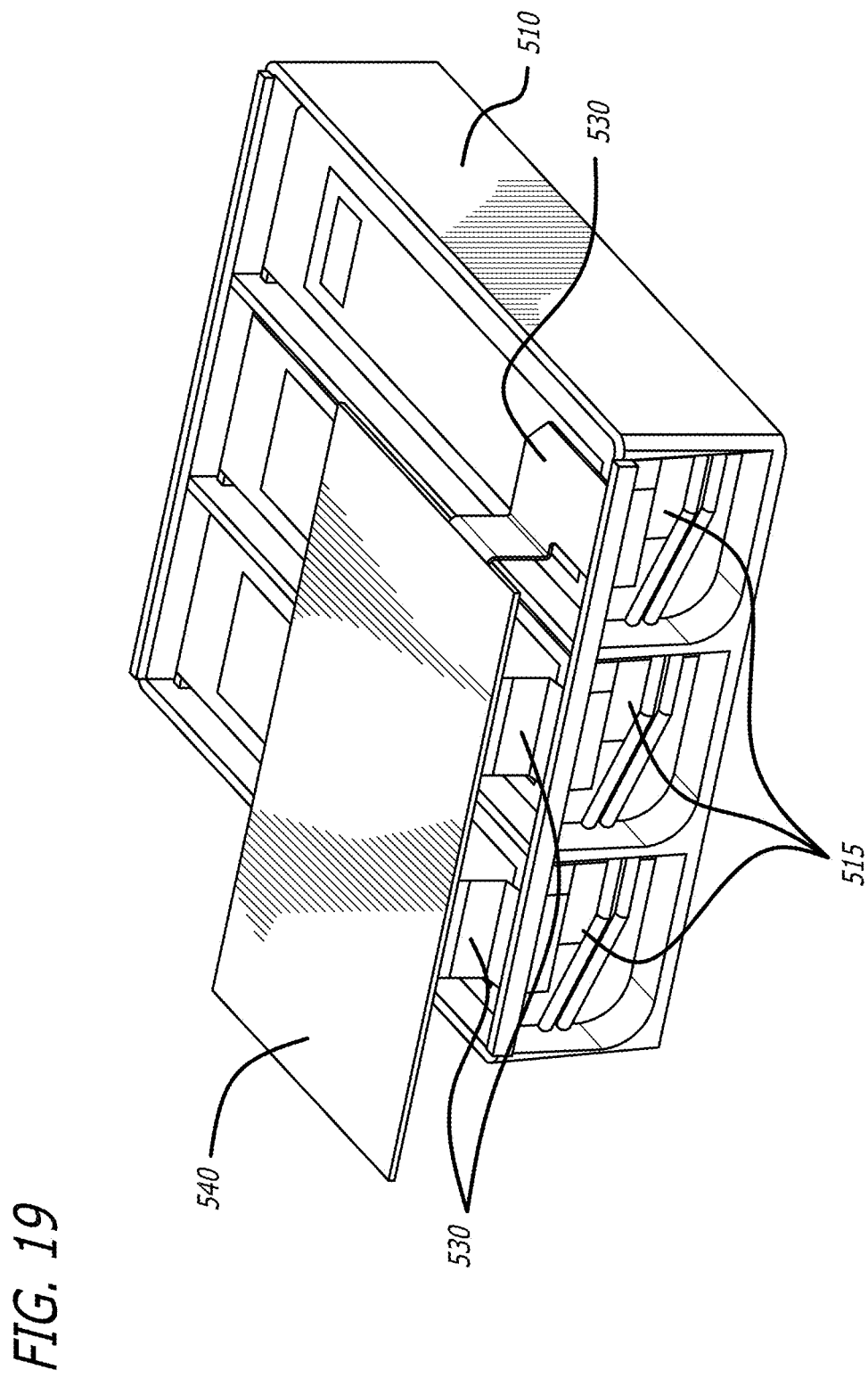
FIG. 19 is a top perspective view of a top of an embodiment of battery receiver showing interconnections with a battery PCA board.

FIG. 19 is top perspective drawing of one arrangement of the batteries within the battery receiver with a top cover of the battery receiver removed to illustrate one method of using flex circuits 530 to connect each of the batteries 515 to the battery PCA board 540.

Figure 20:
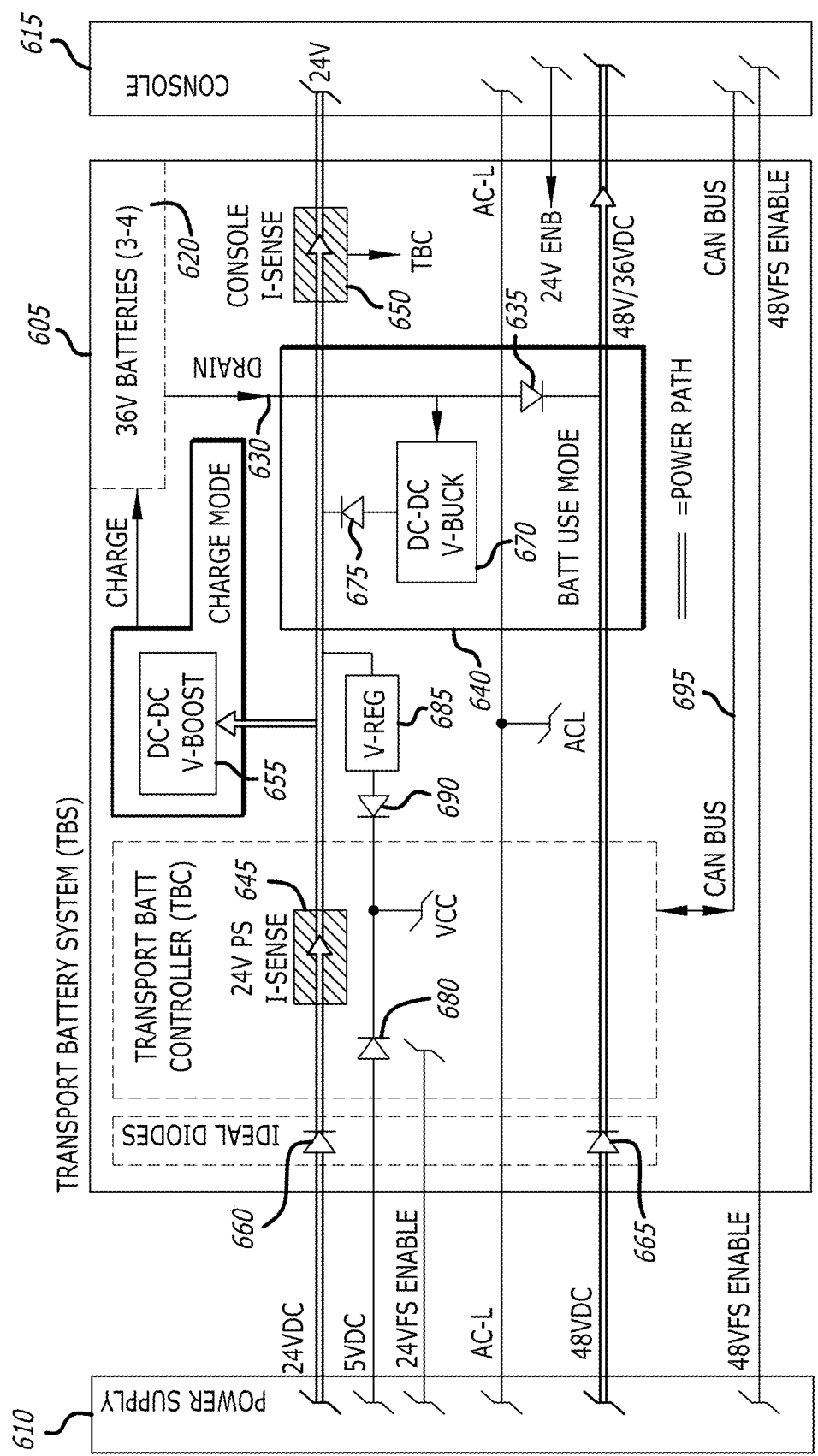
FIG. 20 is a schematic diagram illustrating components of an embodiment of a transport battery system.

FIG. 20 is a schematic diagram depicting various components of an example of a battery management system to be used with a transportable rechargeable battery system and/or transportable heat exchange system. A battery management system or transport battery system (TBS) 605 receives power from power supply 610, and supplies power to a control console 615. As shown, various power and communication lines are used to connect the various components of the system. For example, power supply 610 provides 24 VDC, 5 VDC, and 48 VDC to the TBS.

The TBS includes a transport battery controller (TBC) 625 that will be described more fully below. The TBC includes at least one processor and other circuitry that controls the operation of the TBS, including monitoring and controlling the various charging and discharging operations of the batteries, along with various circuits designed to protect the batteries, and monitor the capacity of the battery or batteries.

When the heat exchange system is being operated using direct current supplied by the batteries 620, power is supplied over a drain line 630 to the 48V/36 VDC line through diode 635.

A circuit 640 monitors a battery use mode of the system. Exemplary modes contemplated are set forth in the following table. The mode of the system varies depending on whether the heat exchange system is powered on and connected to alternating current.

source, 24 VDC power flows from the power supply through ideal diode 660, through sensing circuit 645, and provides 24 VDC power to the console 615 as well as to voltage boost circuit 655 to charge the rechargeable batteries 620.

When batteries 620 are being used instead of alternating current to power the heat exchange system, power is drawn from the batteries through the drain line that also flows into the 48 VDC line through diode 635. The drain line also provides battery power to a DC-DC voltage buck converter circuit, which steps down the 36 VDC being supplied by the batteries to 24 VDC, while stepping the current up. The stepped down 24 VDC output of buck converter 670 flows through diode 675 and into the 24 VDC line to provide 24 VDC power to the console through console current sensing circuit 650.

Power supply 610 also provides the TBC with 5 VDC through diode 680 when the power supply is connected to an alternating current source. When no alternating current is available from the power supply, 5 VDC is supplied to the

| AC Mains Connection State | Power Switch Status | Description |
|---|---|---|
| Not connected | Off | In this state, there is no console operation. The batteries will not be in an operating state and no power is delivered to the console. |
| Not connected | Power switched from Off to On (T) | System powers the display only to confirm operator's intention to Power ON the system on battery only. After confirmation, the system will start normally; if no confirmation is received in a prescribed time, the system will power off completely. |
| AC is suddenly lost (T) | Off | In this state, any battery charging activity will cease. The batteries will then switch to an inactive state and no power will be delivered to the console. |
| AC is lost (T) | On | In this state, the console will continue operation. As it is expected to be mainly used for transport, the compressor is expected to change to minimum speed (charger will need to inform the system or system will need to query the charger on a regular basis; or use the "AC lost" line for indication). From this state the console will then be running on battery power. |
| Present | On | In this state, the console will operate normally. The TBS monitors 24 VDC current to the console from the power supply and current available for charging the battery. The current available for the charging is calculated and adjusted based on the current demands from the power supply. Throttling limits the total current draw from the 24 V supply to 10 Amps. The power supply can tolerate short duration over loading, so the calculations may be made periodically, such as every second or as determined by the TBS. |
| Present | Power switched from On to Off | Transition state that occurs when the switch is turned off. The TBS continues to charge the batteries if charging is needed. The TBS senses the switch state change and stops power delivery to the console and the console shuts down. |
| Present | Power switch remains Off | As above, in this state the console will have no power and there is no 48 VDC to the console. The TBS controls the 24 VDC supply to charge the batteries, if needed. |
| AC is restored | Power switch is On | If the system was in "transport mode", the console will continue to operate normally. If the charger was in a non-maintenance state (e.g. max cooling), that state may be restored by confirmation. This is a transition state and proceeds into Present-On. |

(T)—transition state

A sensing circuit 645 in communication with the 24 VDC line monitors the current being drawn on the power supply by the system, and provides a signal to the TBC representative of the current sensed by circuit 645. There is also a console current sensing circuit 650 that monitors the current being supplied to the console. The console current sensing circuit communicates with the 24 VDC line and is located between the console and a DC-DC Voltage Boost circuit 655. When power is being supplied by an alternating current TBC by tapping the 24 VDC line which is being supplied with 24 VDC by the buck circuit 670 through a voltage regulating circuit 685 and diode 690.

Because of the arrangement of diodes 660, 680, 690, and 675, when current is supplied by the power supply 610, the only time that power flows from the batteries into the 24 VDC line is when no power is being supplied by power supply 610. This arrangement has at least two advantages: 1) it allows the batteries (or battery) to be charged when the heat exchange system is being powered by alternating current, and 2) allows automatic change over to the batteries when the alternating current supply is interrupted. In the exemplary transport battery system 605 shown, the changeover may occur without requiring the intervention by, or notification to, a processor or processors or without manual intervention.

Also shown is an AC-L line that may supply a signal indicating a supply of alternating current has been interrupted. For example, when alternating current is supplied, the AC-L line may be held high; when the alternating current supply is interrupted, the AC-L line may go low, which can be detected by a processor monitoring that line. As will be described below, the processor may then send a signal to a display device indicating that alternating current has been lost, and that the system is now operating on battery power.

An electronic communication bus, such as, for example, a CAN (Controller Area Bus) bus 695 shown in FIG. 20 may connect the TBC to one or more processors or systems located in the console 615. A CAN bus is a robust bus standard designed to allow microcontrollers and devices to communicate with each other in applications without a host computer. Such a bus provides for sending signals representing various operating states, operating data, information, and/or commands between the various processors, system, and subsystems of the battery system and the other systems of the heat exchange system. Such communications will typically be enabled by using one or more communication protocols as are readily known in the art.

Figure 21:
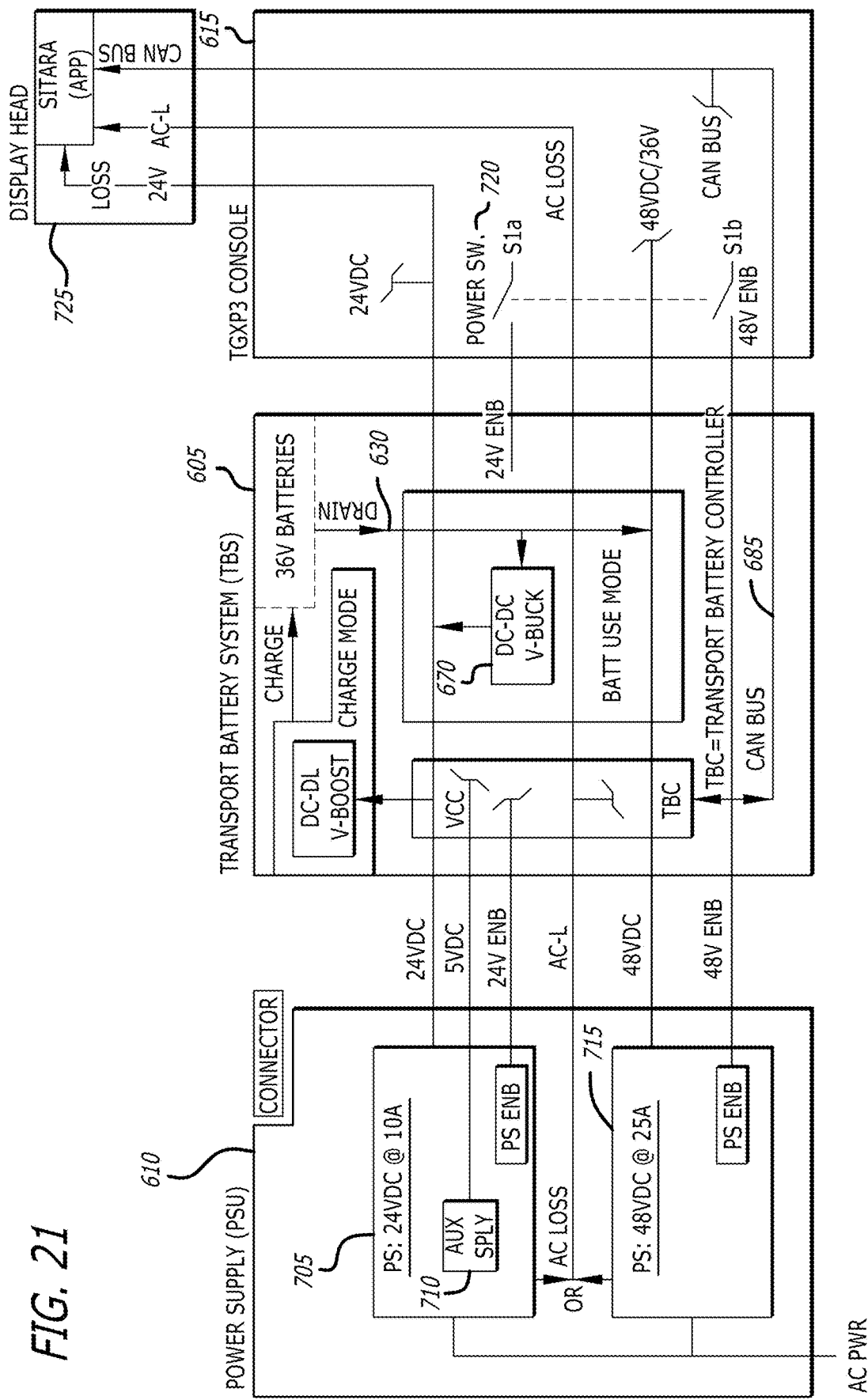
FIG. 21 is a schematic diagram illustrating one embodiment of interconnections between a power supply and a console and the transport battery system of FIG. 20.

FIG. 21 is a schematic diagram of an embodiment showing additional details of a PSU and battery management system for managing the operation of a rechargeable battery or batteries used to power a transportable heat exchange treatment system. As shown in FIG. 20, there is a power supply unit (PSU) 610 having power supplies for supplying 24 VDC and 48 VDC to the various systems of the heat exchange system. The 24 VDC power supply 705 is configured to receive alternating current power from a suitable source. The 24 VDC power supply converts the alternating current to direct current, and reduces the voltage output to 24 volts, and delivers 24 volts at a current of up to 10 amps to the 24 VDC line. The 24 VDC supply 705 also includes circuitry and components, shown as AUX SPLY 710, which further reduces the output voltage to 5 VDC.

The PSU also has a 48 VDC power supply 715, which includes circuitry and components configured to convert alternating current to direct current, and to output 48 VDC at up to 25 amps current to the 48 VDC line.

FIG. 21 also illustrates one embodiment of a console 615 that receives power from the PSU 610, as well as from the TBS 605. Console 615 includes a power switch 720. Power switch 720 may be a mechanical switch arrangement that directly controls the PSU, or in other embodiments may be a combination of a mechanical switch or switches and a relay circuit. Power switch 720 has a power-on state and a power-off state.

In another embodiment, power switch 720 communicates with the PSU electronically through a 24V ENB line and a 48V ENB line. When power switch 720 is in the on state, a signal is transmitted over the 24V ENB line to activate the 24 VDC power supply 705. A signal is also transmitted over the 48V ENB line to activate the 48 VDC power supply 715. The transmitted signal may be continuous, or may be maintained only long enough to activate the 24 VDC and 48 VDC power supplies. In one example, for example, activation of the power supply switch into the power-on state may cause the voltage of the 24V ENB and 48V ENB lines to go high. When the 24V ENB and 48V ENB lines go high, the 24 VDC and 48 VDC power supplies are turned on. Alternatively, activating the power supply switch to the power-off state may cause the voltage on the 24V ENB and 48V ENB lines to go low. When the 24V ENB and 48V ENB lines go low, the 24 VDC and 48 VDC power supplies are turned off.

Also shown in FIG. 21 is a display 725. Display head 725 includes various indicators such as indicator lights, analog displays, digital displays, alarms or a combination of one or more of each of those lights, alarms and displays. Such displays are used to inform the operator of the transportable heat exchange system regarding various operating states and parameters related to the operation of the system. The display head, or the console 615, may also include various other devices or systems to alert the operator that one or more subsystems of the heat exchange system need attention or corrective action.

FIG. 22 is a schematic diagram of one embodiment of a charging circuit configured to charge the battery or batteries powering the various embodiments of the disclosed transportable heat exchange system. Where FIG. 22 depicts elements that are similar to those depicted in previous diagrams, those elements retain their original reference numerals.

An interface 750, which may be a connector, or may simply represent a plurality of communication lines on a bus, connects various components of the charging circuit with a transport battery processor (not shown) which monitors and controls the charging circuit. While only one embodiment of the charging circuit is shown communicating with battery1 770, it will be understood that a separate charging circuit, similar to the circuit connected to battery1, is connected to battery2 795 and battery3 780. In this manner, the charging of each battery may be separately monitored and controlled by the transport battery processor.

Communication lines I2C3, BT0, and BT1 communicate with vboost charger 655 to control the charging and discharging of battery1 770. As shown, lines BT0 and BT1 transmit signals to the charger 655 through a 2-line-4 multiplexer 755. Line A0 transmits the signal to IO MUX 1 760. Line I2C3 is used to both transmit signals to, and receive signals from I-O MUX1 760. I-O MUX1 also receives a signal from battery1 770 on a THERM line.

There is also shown in FIG. 22 a gas gauge circuit 785, such as that distributed by Mouser Electronics. This gas gauge circuit provides a signal to the transport battery processor interface 750 over line MAXBG1 (alert), and transmits and receives communication from the transport battery processor over line I2C (I2C) through I2C MUX 765. Gas gauge circuit 785 monitors the current being drawn or stored into battery1 770 across I-sense resistor 810 connected to a communication line of battery 770 and a negative power terminal 815 of battery1 770.

Also shown is a communication line BATT ENB that provides signals to an IN DEV terminal of battery 770. A communication line originating from a battery connector line THERM provides signals both to I-O MUX 760 and to gas gauge 785.

The positive terminal 820 of the battery is shown providing power to ideal diodes 790, 795, such as a model number LTC4355 ideal diode distributed by Linear Technology Corporation. The ideal diodes are used to control the flow of current through their associated lines. Additional ideal diodes 800 and 805 are connected to the positive terminals of batteries 775 and 780, respectively.

In one embodiment, the console may include a battery or a rechargeable battery in addition to the battery or batteries mounted in the battery receiver or tray described above. This embodiment allows the console to be shipped without batteries mounted in the receiver, but still be functional as soon as the system is put into service after shipment. As will be described below, this additional battery may also be maintained in a fully charged condition and only used to power the system when the battery or batteries contained in the battery receiver are drained or are being synchronized.

In one embodiment, the system is configured to power on to provide treatment if the system is connected to an external direct current source, such as 12 volt direct current source provided by an automobile or truck battery system or portable battery. External systems that provide 24 volt or 48 volt direct current may also be used to power the system. When the system is connected to such an external direct current source, the system may control itself to operate the system and/or charge the system rechargeable battery or batteries, provided the direct current source is capable of providing sufficient current to operate the system and charge the rechargeable battery or batteries of the system. Where sufficient current is available to both operate the system and charge the rechargeable battery or batteries, the system will control itself so that the external direct current is used to only power the system. Alternatively, the system monitors the current needs of the console, and only provides current remaining after the needs of the console are met to charge the rechargeable battery or batteries of the system.

The transport battery system described herein provides for maintaining of the operation of the heat exchange system when alternating current is either not available or if the supply of alternating current is interrupted. Such situations occur when the system is transported to a patient who is being evaluated at a location remote from a treatment facility, such as in an emergency where paramedics arrive in an ambulance at the patient's location and it is determined that the patient needs to be transported to the remote treatment facility. Another situation arises when a patient, already being treated in a treatment facility, needs to be moved to another location within the treatment facility, and it is desired to continue temperature management during the relocation process.

In accordance with the various embodiments described above, changing over from alternating current to battery provided direct current occurs automatically at the time that the alternating current supply is disconnected from a source of alternating current, without first needing to turn the heat exchange system off to switch over to battery power. As described with reference to the exemplary system depicted in FIG. 20, power is supplied by the batteries 605 only when neither 24 VDC nor 48 VDC is being supplied by power supply 610. Ideal diodes 660 and 665, act as short circuits, or closed switches, when they are forward biased. When power from the power supply 610 is interrupted because the power supply has been disconnected from an alternating power source, power flow through those diodes ceases, and they prevent backwards flow of power back into the power supply circuitry.

Similarly, while power is being supplied on the 48 VDC line, ideal diode 635 prevents power from flowing from the 48 VDC line back into the batteries because ideal diode 635 is reverse biased by the 48 VDC. However, when current flow from the power supply on the 48 VDC line ceases because connection to the alternating power source has been interrupted, 36 volt current flow from batteries 605 is allowed to flow through ideal diode 635 into the 48/36 VDC line. This transfer from power supply 610 to batteries 605 is automatic and does not need an intervention by the transport battery processor.

As described above, in the event that the connection to the alternating current source is interrupted, a signal provided by the power supply on the AC-L line will be received by the transport battery processor, which will then control an indicator on the console or display to inform an operator of the change in status of the power supply. Additionally, in some embodiments, the processor may control a display to inform the operator of a value related to the amount of remaining energy in the battery or batteries. In other embodiments, there may be a separate display for each battery being used to power the heat exchange system to assist the operator in managing the current being drawn from the batteries during transport so as to maintain operation of the heat exchange system for as long as the transport of the patient requires.

The various embodiments of the system described herein provide for charging the battery or batteries while the system is connected to a source of alternating current, even when the system is not being used. When the system is used while on battery power, the transport battery processor monitors the amount of current drawn from the batteries, and indicates the amount of capacity remaining for each battery on a display visible to the operator of the system. This capacity value, representing the amount of energy remaining in the battery at any given time, is stored in a memory in communication with the processor, and/or displayed to the operator of the system. In this manner, the system may be turned off and stored until the next time the system is needed.

In most cases, the system may be reconnected to an alternating current source, which will proceed to recharge the batteries, and reset the capacity value for each battery in the memory. However, there may be times when the system may be disconnected from an alternating current source for sufficient time so that the actual amount of energy stored in the battery will be less than the stored battery capacity due to current loss from battery. Thus, if the system is needed, it is possible that the actual capacity of the battery will be less than the indicated or stored capacity.

In some embodiments, the processor may monitor the current draw on the 24-volt DC line, and adjust the current available for charging the battery in accordance with the power needs of the console to limit the current draw on the 24-volt direct current output to 10 amps. In some embodiments, the processor adjusts the current available to charge the battery periodically, at an interval of in the range of 0.1 to 10.0 seconds. For example, if the console is consuming all of the available current, the processor will not provide any current to charge the battery or batteries.

In some embodiments, the processor may control the speed of the compressor of the refrigeration system cooling the heat exchange fluid to change to a low speed when the system is disconnected from the alternating current source. In other embodiments, the processor controls the compressor to operate at the same speed it was operating when the alternating current source was disconnected. During such a loss of alternating current supply, the processor may also provide an indication to an operator that the connection to the alternating current source was lost, and in some embodiments, also provide an indication to an operator of the system of the amount of battery capacity remaining available to the system. Such an indication may be displayed on the console of the system; additionally, the processor may cause an audible and/or visual indication, alert, or alarm, of the loss of alternating current power or of the amount of battery capacity remaining available to the system to the operator.

In another embodiment, the transport battery processor or other system processor monitors the operation of the system and alters or selects the operating mode of the system when the system is disconnected from an alternating current supply in accordance with the power needs of the system. For example, the processor monitors the current usage of the system utilizing one or more sensors such as depicted by sensor 650 (FIG. 20), and calculates a remaining battery capacity value by subtracting the current usage from the a battery previous battery capacity value, and depending on the amount of battery capacity or stored energy that is available from the rechargeable battery or batteries, the processor may control the system to operate in a cooling mode, warming mode, a maintenance mode, a full power MAX cooling mode, or other operating mode, or the processor may alter the rate of cooling or warming.

In one embodiment, the system determines how much battery capacity or stored energy is available when disconnected from an alternating current source, and dependent on an input from an operator, for example, by entering a value representative of how far or how long a patient must be transported by entering the value into an appropriate input on the console, such as a key pad or other device, adjusts the operating mode accordingly to ensure that the patient treatment can be maintained for the length of time needed to complete transport of the patient. For example, given the available battery capacity or stored energy, the system may determine that the system cannot be operated in a MAX cooling mode for the required transport time, and automatically place the system in a maintenance mode. Alternatively, the system may operate at a reduced level of cooling instead of attempting to operate in the MAX cooling mode.

In one embodiment, the processor, as described above, is configured to monitor the power needs of the system and/or energy level or capacity of the battery using various sensors disposed throughout the system to measure the status of various operating parameters of the system and/or battery parameters. The processor is responsive to the signals received from these sensors to control the operation of the system. In this way, the processor and sensors form part of a closed feed-back system for controlling the system to achieve a desired treatment regimen during transport of a patient, In one embodiment, a look-up table accessible by the processor may contain data indicative of what operating modes can be used depending on duration of transport and/or battery capacity or charge level. For example, if the duration is 20 minutes, the processor may access the table and depending on the operating mode of the system desired, may indicate that that operating mode cannot be continued for the entire expected duration of the transport, and either recommend another operating mode to the operator, or automatically altering the operating mode and notifying the operator of the change. Alternatively, the processor may automatically alter some other operating parameter, such as, for example, pump speed or fluid flow to ensure that the desired operating mode can be maintained for the expected duration of the transport.

Such embodiments are advantageous in that the system is capable of configuring itself to optimize treatment to the patient as a function of both treatment duration and available battery capacity or stored energy. For example, the system may determine that the available battery capacity or stored energy will be able to operate the system at a reduced cooling or maintenance mode for a greater period of time than the system could be operated at MAX cooling.

In another embodiment, the system may monitor the battery capacity or energy consumption rate and alter the operating mode of the system when the battery capacity reaches a threshold capacity to prolong the operation of the system. For example, if transport takes longer than anticipated, the system may alter the operating mode to reduce power consumption by the system to prolong battery life. In another embodiment, the system may limit the operating mode that the system can be operated in depending on the amount of energy remaining in the rechargeable battery or batteries. For example, if the amount of energy remaining in the rechargeable battery or batteries is below a selected threshold, the system may only allow the system to be operated in a maintenance or reduced cooling mode, and prohibit operation of the system in a MAX cooling mode.

One advantage of the transport management system described above is the ability to manage charging of the battery or batteries so that at least one battery is always available to power the system in the case where the system needs to re-learn, or synchronize the stored capacity of each rechargeable battery being used to power the system. In such embodiments, the transport battery processor or system processor may also maintain an archive memory of the capacity of each battery when at the time that battery capacity is last synchronized, along with a time stamp indicting the date and/or time that the synchronization process was completed.

In one embodiment, the transport battery processor analyzes the current and voltage being supplied by a battery when the battery is being used to power the system, and makes a determination as to whether the capacity indicated on a so-called gas gauge display is accurate. If the processor determines that the gas gauge display is not accurate, the processor will submit that battery to a synchronization process, described more fully below.

In another embodiment, the transport battery processor monitors usage of the battery, and in accordance with the time stamp associated with the last time the battery capacity and gas gauge were synchronized, determines whether the battery should be re-synchronized.

If the processor determines that a battery needs to be synchronized, the processor will allow the system to drain the battery until its stored energy is essentially exhausted. The processor will then control the charging system to recharge the battery until the battery no longer accepts any energy. During the charging process, the processor monitors the amount of energy being stored in the battery, and when the battery is fully charged, stores the new value for the battery's capacity in the memory, with an appropriate time stamp. In some embodiments, the memory will retain the capacity value and timestamp of each synchronization of the battery. These embodiments are advantageous because a log of values related to the operational health of the battery can be analyzed to determine when a battery needs to be replaced, rather than synchronized again. In other embodiments, the new capacity value and time stamp replaces the old capacity value and time stamp.

Because it is important to keep at least one battery available to power the system, if needed, while the other one or more batteries are being synchronized, the transport battery processor may use various charging strategies to synchronize the batteries that need it. For example, when more than one transport battery needs to be synchronized, the transport battery processor may synchronize each of the batteries at different times so that at least one battery is always available to power the system. In another example, the processor may determine the measured voltage of each of the batteries, and then draw current from the battery or batteries having the highest measured voltage until the voltage of the battery or batteries are drawn down to the level of the voltage of the battery undergoing synchronization. In another example, the transport battery processor may defer synchronizing any battery until the heat exchange system is not in operation. In still another embodiment, the transport battery processor may control the system to charge a battery being synchronized at a different current than the other battery or batteries that are currently being charged when the heat exchange system is connected to an alternating current source.

In certain embodiments, the transport battery processer may control the system to charge or synchronize one or more batteries only when the alternating power supply is connected to a source of alternating current. In another embodiment, transport battery processor may control the system to charge or synchronize one or more batteries while the system is being used to treat a patient, or when the system is not being used to treat a patient, but the system is powered on. In another embodiment, the processor may control the system to charge and/or synchronize a battery or batteries when the system is powered off.

Figure 23:
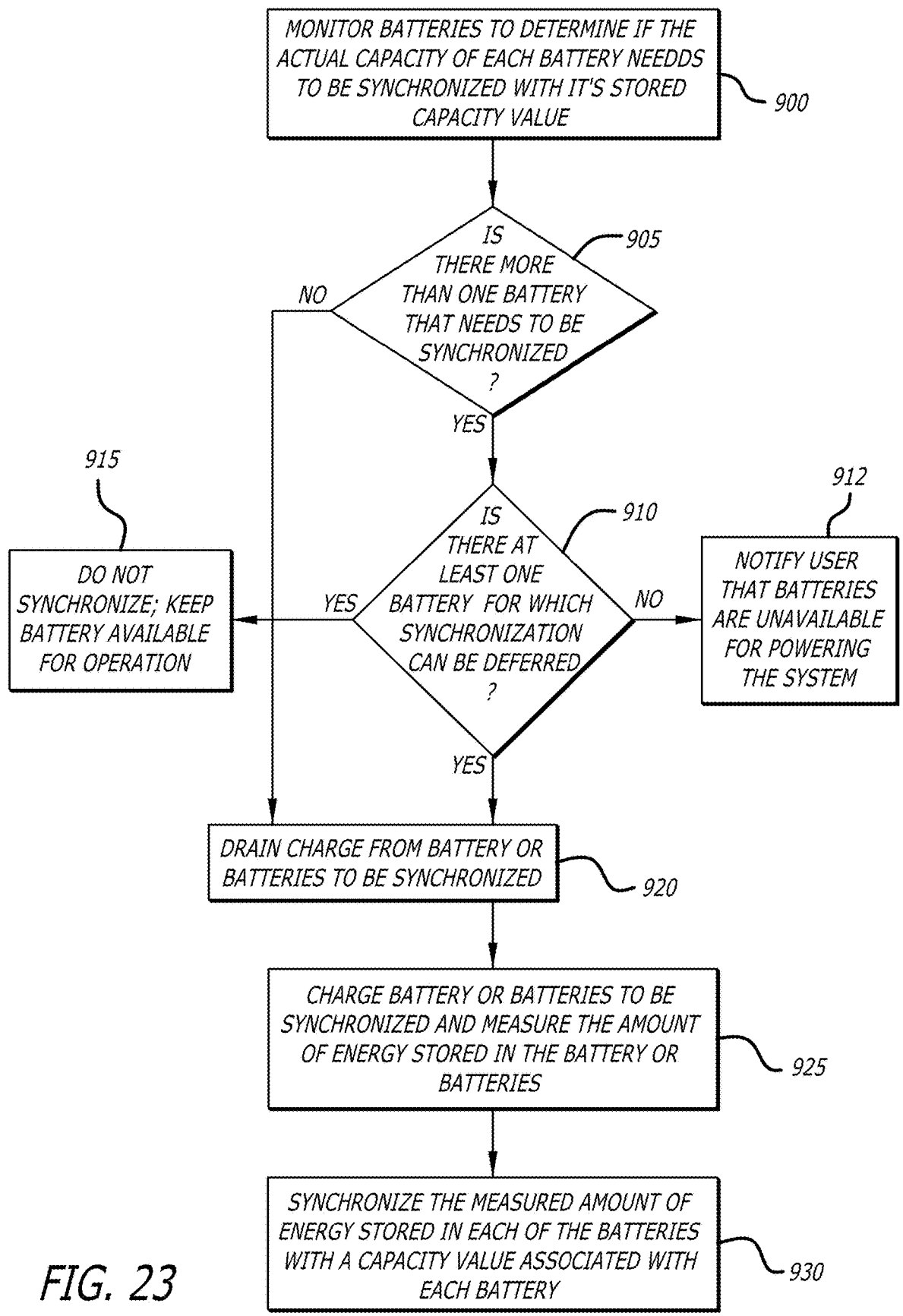
FIG. 23 is a flow chart diagram one embodiment of a process for resynchronizing a stored memory representative of a capacity of a rechargeable battery with an actual measured capacity of the rechargeable battery.

FIG. 23 is flow diagram illustrating one embodiment of a method of staggering the synchronization of one or more batteries as set forth above. In this embodiment, the transport processor monitors the batteries of the system to determine if one or more of the actual capacity of each battery needs to be synchronized with its capacity value stored in a memory in box 900.

The processor determines where more than one battery needs to be synchronized in box 905. If so, the processor determines whether there is at least one battery for which synchronization can be determined in box 910. If result of box 905 is no, then the process branches to box 920. If the result of box 910 is yes, that is, that there is at least one battery for which synchronization can be deferred, then the processor identifies that battery as such in box 915, and proceeds to the process of box 920, where it begins the synchronization process on the one or more batteries identified as needing synchronization. In box 920, the processor controls the battery or batteries to be synchronized to allow those battery or batteries to be drained of their charge. When the battery or batteries have been discharged in box 920, the processor controls a charging circuit to recharge the battery or batteries, and measures the amount of energy being stored in each battery until each of the battery or batteries is fully charged in box 925. When the charging process is completed for a battery, the processor determines a measured capacity for the battery from the measured amount of energy stored in the battery during the charging process. The process then synchronizes the measured capacity of the battery with the capacity value stored in the memory associated with the processor in box 930, and may also cause an indication of the newly synchronized capacity value to be displayed on a console display or gas gauge indicator.

In another embodiment, the system/processor is configured to optimize battery charging based on the operating power needs of the system when the system is connected to a source of alternating current. For example, when the system is connected to an alternating current source, the system may alter the amount of current provided to charge the battery as a function of the amount of current needed to power the system to provide treatment to a patient or otherwise operate the system. In one exemplary embodiment, the system may determine how much current is available from the source of alternating current, and alter the charging mode of the system for the battery to ensure that adequate current is provided to the system to provide for patient treatment without altering the treatment mode of the system. In another embodiment, the system may be configured to trickle charge the battery or batteries when the system is being used to treat a patient, but change to full or high speed charging mode when the system is powered off, or when the system is in stand-by mode.

For example, the processor, as described above, is configured to monitor the power needs of the system and/or energy level or capacity of the battery using various sensors disposed throughout the system to measure the status of various operating parameters of the system and/or battery parameters. The processor is responsive to the signals received from these sensors to control the charging of the rechargeable batteries. In this way, the processor and sensors form part of a closed feedback system for controlling the system to achieve a desired treatment regimen during transport of a patient, while determining whether to charge, and in which charging mode to use, one or more of the rechargeable batteries while the treatment is ongoing.

In one embodiment, a look-up table accessible by the processor may contain data indicative of what charging modes can be used depending how much power is being drawn from the battery or batteries, and how much current is available from the alternating power source. For example, if the current draw of the system is below a certain threshold, the processor will charge the battery in a full mode, a speed charge mode, or a trickle mode. The processor may also respond to changes in the power draw of the system to automatically alter the charging mode and notify the operator of the change.

In some implementations, an example heat exchange system is configured to change to a low-power operating mode. In certain implementations, the heat exchange system may be a system such as heat exchange system 10 described herein, or any heat exchange system manufactured by ZOLL Medical Corporation or ZOLL Circulation, Inc., e.g., ZOLL's Thermogard XP® temperature management system or ZOLL's Thermogard XP3 temperature management system. The heat exchange system 10 can use a low-power operating mode when the heat exchange system detects that external power is disconnected, detects that a battery is low, or otherwise determines that power should be conserved. The heat exchange system 10 can operate in a low-power mode when power is supplied by the transportable battery system described previously. The heat exchange system 10 can operate in a low-power mode when the power is supplied by an uninterruptable power supply (UPS).

In an aspect, when the heat exchange system 10 is disconnected from a source of alternating current, the heat exchange system 10 can draw power from a transport battery system (e.g., TBS 605 of FIGS. 20-21), as previously described. The TBS detects that external power is no longer available and provides DC power to the console. In some implementations, the TBS 605 provides either or both 24V and 36V power to the heat exchange system 10. The TBS 605 can generate a low-power signal to indicate to the heat exchange system 10 that the TBS 605 is operating on battery power rather than power from an external power source. In response to receiving the low-power signal, the control console 14 is configured to adjust operation of the heat exchange system 10 for controlling the heat exchange device (e.g., catheter 12, body surface heat exchanger 402, or other heat exchange device previously described). The heat exchange system 10 changes operation to operate in a low-power mode, described further in relation to FIGS. 25-26.

Figures 24A, 24B:
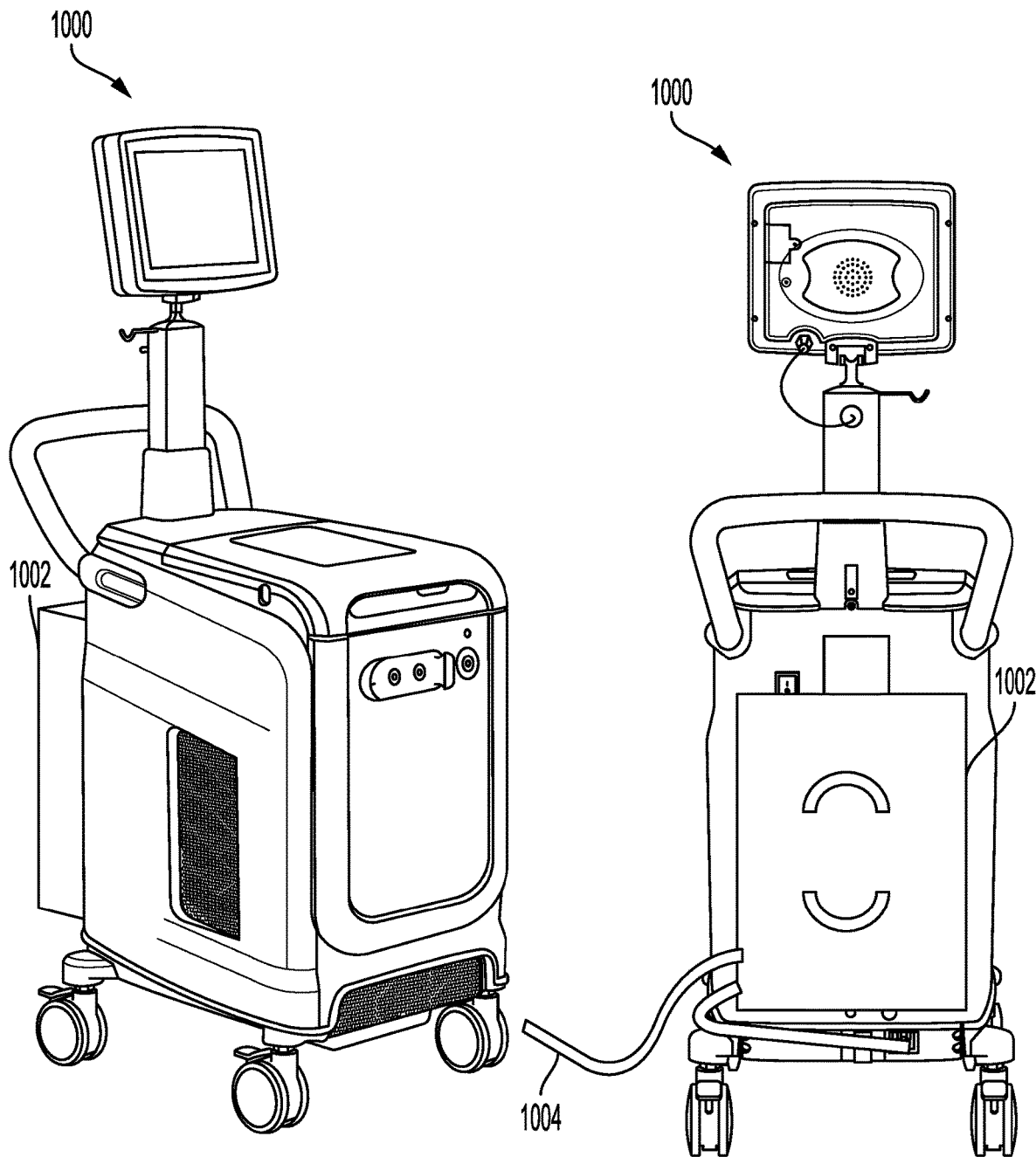
FIGS. 24A-B are perspective views of the heat exchange system with an uninterruptable power supply (UPS).

FIGS. 24A-B are perspective views of an example heat exchange system 1000 with an uninterruptable power supply 1002 (UPS). The heat exchange system 1000 can include the heat exchange system 10 describe previously with respect to FIG. 1. In certain implementations, the heat exchange system 1000 may be any heat exchange system manufactured by ZOLL Medical Corporation or ZOLL Circulation, Inc., e.g., ZOLL's Thermogard XP® temperature management system or ZOLL's Thermogard XP3 temperature management system. Generally, the heat exchange system 1000 is configured to interface with the UPS 1002 as a source of power. Generally, the UPS 1002 receives AC power from a source of alternating current (e.g., by line 1004 shown in FIG. 24B). The UPS 1002 converts the AC power to DC power and the DC power back to AC power. If wall power is insufficient to source the load required by the heat exchange system 1000, the UPS 1002 draws power from a battery supply and converts this DC power into AC power, which is fed into the heat exchange system. The UPS 1002 is configured to provide a low-power signal to a control console (e.g., control console 14 previously described in relation to FIG. 1). The control console is configured to change operation of the heat exchange system 1000 for heating and cooling a heat exchange device (e.g., catheter 12, body surface heat exchanger 402, or other heat exchange device previously described).

When a heat exchange system (e.g., heat exchange system 10 of FIG. 1, heat exchange system 1000 of FIGS. 24A-B, etc.) receives a signal indicating a low-power operating mode, the heat exchange system adjusts operation of a heat exchange device in order to draw less power while still managing patient temperature. Generally, to consume less power, a processor (e.g., a controller of the control console) of the heat exchange system is configured to reduce a speed of a compressor (e.g., compressor 92 previously described in relation to FIGS. 6-10) or to switch between an ON and OFF state of the compressor.

As previously stated, a processor of the control console can be configured to control the speed of the compressor of the refrigeration system cooling the heat exchange fluid to change to a low speed when the system is disconnected from the alternating current source. The compressor can be configured to cycle between an ON state and an OFF state at a slower rate than during operation with full power. The result is that the heat exchange system 10 has a coarser control of a temperature of the heat exchange device (and the patient being cooled by the heat exchange device), but less power is used to cool the patient and maintain the cooled body temperature of the patient. Generally, the heat exchange system 10 allows the heat exchange device, and the patient, to warm to a higher temperature than what would occur during full-power operation by turning the compressor off. Upon the patient or heat exchange device reaching a threshold temperature as measured by a temperature sensor, the processor of the heat exchange system 10 controls the compressor to turn the compressor back on and cool the patient down back to a cooled state. When the patient reaches the cooled state, the compressor is turned off, and the cycle repeats.

Cyclical operation of the compressor uses less power than full time operation of the compressor. Generally, the compressor speed is adjusted to slow or hasten the cooling process, but the compressor remains active during full power operation. However, during the low-power mode, the compressor can be switched between being deactivated entirely and operating at a fixed lowest speed for maintaining patient temperature. Generally, the patient temperature is maintained between a lower threshold temperature and an upper threshold temperature. When the patient temperature drops below the lower threshold value, the processor causes the compressor to deactivate. The heat exchange system 10 allows the heat exchange device to warm, and thus warm the patient. The lower threshold temperature can be set to a value representing a temperature when the patient begins to be cooled too much. In some implementations, the lower threshold temperature can be set to a slightly higher temperature to save additional power. When the patient temperature rises above the upper threshold temperature, the compressor is reactivated to cool the heat exchange device and the patient.

The values of the upper threshold temperature and the lower threshold temperature are determined based on how much cooling power should be provided to the patient for maintaining patient body temperature in a cooled state. The upper threshold value and the lower threshold value can also be based on the physical (e.g., hardware or operational) parameters of the heat exchange device and heat exchange system 10, such as a size of cooling plates, heat transfer coefficient of the heat exchange device, material of the cold plates, and so forth. The upper and lower threshold values can be set based on the physiology of the patient. For example, the upper and lower threshold values can be based on the desired temperature for maintaining the patient, a patient metabolism, effects of warming by other heat exchange device or the environment, and so forth. In some implementations, the temperature of the cold plates are used as proxy values for measuring cooling power delivered to the patient. In some implementations, the lower temperature threshold for the plates is approximately 5 degrees C. for maintaining a patient at 32 degrees C. In some implementations, the upper temperature threshold for the plates is approximately 16 degrees C. for maintaining a patient at 32 degrees C. While cold plate temperature values are used for setting thresholds in this example, other temperature values (such as a temperature value read from a temperature sensor) can be used to set the threshold. The exact values of those thresholds can also vary based on the particular physical parameters of the heat exchange system 10.

Generally, during low-power operation, a heater system can be deactivated to save additional power. The heater system is used in combination with cold plates of the heating/cooling system. When the patient temperature is too low, the heater system in communication with cold plates of the heat exchange system 10 is configured to activate to warm the cold plates slightly. The heater system can include heating coils. The heat exchange system 10 generally uses the heater system for fine-tuning control of the temperature of the cold plates and thus the temperature of the heat exchange device and patient. However, when the heat exchange system 10 is operating in a low-power mode, the heater system can be deactivated. Instead of activating the heater system, the compressor is deactivated, as previously described.

A profile of operation of the compressor can be generated for the low-power mode of the heat exchange system 10. Generally, the profile can predict a battery capability for operating the heat exchange system 10 under given conditions. The prediction can receive values for the operational parameters of the heat exchange system 10, a desired temperature for maintaining the patient, patient parameters, and so forth. In response to receiving these inputs, logic of the data profile can produce an estimate of how long the heat exchange system 10 can operate using the battery.

In one example, the profile can include a cycle periodicity for the compressor. The profile includes how long the compressor is in the ON state and the OFF state for maintaining patient temperature. In some implementations, the processor of the heat exchange system 10 measures the temperature of the cold plates at intervals and turns the compressor to an ON state or OFF state as previously described. In some implementations, the processor of the heat exchange system 10 measures the temperature of the cold plates or coolant, e.g., glycol or a refrigerant, at intervals and uses the measured temperature to turn the compressor to an ON state or OFF state. In some implementations, the processor can raise the upper temperature threshold based on an amount of battery power remaining in order to extend operation of the heat exchange system 10 as long as possible. A projection of how long the heat exchange system 10 can run in the low-power mode with the remaining battery power can be shown in a display to the user. The heat exchange system 10 can, using the control console 14, present to the user how long the heat exchange system 10 can operate using the battery under the profile. In some implementations, the user can adjust the profile (e.g., by adjusting one or more parameters of the profile such the plate temperature thresholds) and receive an update showing how battery life is extended or shortened.

Generally, the profile calculates the effects of the cycle times on battery life and projects how much power will be consumed if the profile is followed. If the amount of remaining battery power is known, the profile projects when the battery power will expire. For example, a profile can include the following schedule estimate for operation of the system in low power. Given a battery capacity of 90 W-hours, a power draw of 150 W at 1800 rpm for a cooling compressor, 100 W of non-compressor power draw, estimates of cooling plate cool rates, patient thermal load, and plate temperature thresholds of 5 and 16 degrees C., the following schedule is projected. In a first cycle, the compressor is off for about 5 minutes causing the plates to warm from 5 degrees C. to 16 degrees C. The compressor is turned on for about 8 minutes to cool the cold plates until the plates are again 5 degrees C. This cycle runs two times before battery power is expired. This allows the heat exchange system 10 to operate for about 26 minutes on battery power, when under typical operation only about 15 minutes or less of operation would be available. If more battery capacity is available, the cycle repeats three or more times. If the non-compressor power draw is lower than 100 W, the number of cycles can be extended even further.

In some implementations, profile can be used to guide operation of the heat exchange system 10, rather than simply estimate battery life. For example, the profile can include a timing diagram or scheme for turning the compressor ON and OFF over time. The profile can indicate durations of ON/OFF periods, temperature thresholds, W/cycle, a number of cycles, and so forth. The heat exchange system 10 may use the profile to maximize battery life.

In an aspect, a portable system for managing the temperature of a patient during transport includes a heater/cooler configured to be in fluid communication with a heat transfer catheter configured for insertion into a patient or a heat transfer surface pad and a control console (e.g., control console 14) comprising a processor configured to control operation of the heater/cooler. In some implementations, a processor of the console is configured to receive a low-power signal indicating that a connection to a source of alternating current (e.g., an external supply of power) is interrupted and power is supplied by a battery. The processor is configured to cause the heater/cooler to operate in a low-power mode in response to receiving the low-power signal. An alternating current power supply is configured to provide power to the control console and the heater/cooler. The alternating current power supply is configured to receive power from a source of alternating current and provide direct current to the heater/cooler, control console, and other portions of the heat exchange system 10. In certain implementations, the alternating current power supply is configured to send the low-power signal to the processor. In some implementations, another device besides the alternating current power supply can be configured to provide the low-power signal to the processor. In some implementations, an uninterruptable power supply (UPS) is configured to provide alternating current to the alternating current power supply and receive power from the source of alternating current. In some implementations, the processor is configured to receive a low-power signal sent by the UPS indicating a connection to the source of alternating current is interrupted and a UPS battery is supplying power. In some implementations, the portable system includes at least one battery, wherein the processor is configured to switch to receive power from the battery in response to receiving the low-power signal. In some implementations, the processor causes the heater/cooler to operate in a low-power mode comprises causing a compressor of the heater/cooler to cycle between an ON state and an OFF state, as described in relation to FIGS. 25-26.

Figure 25:
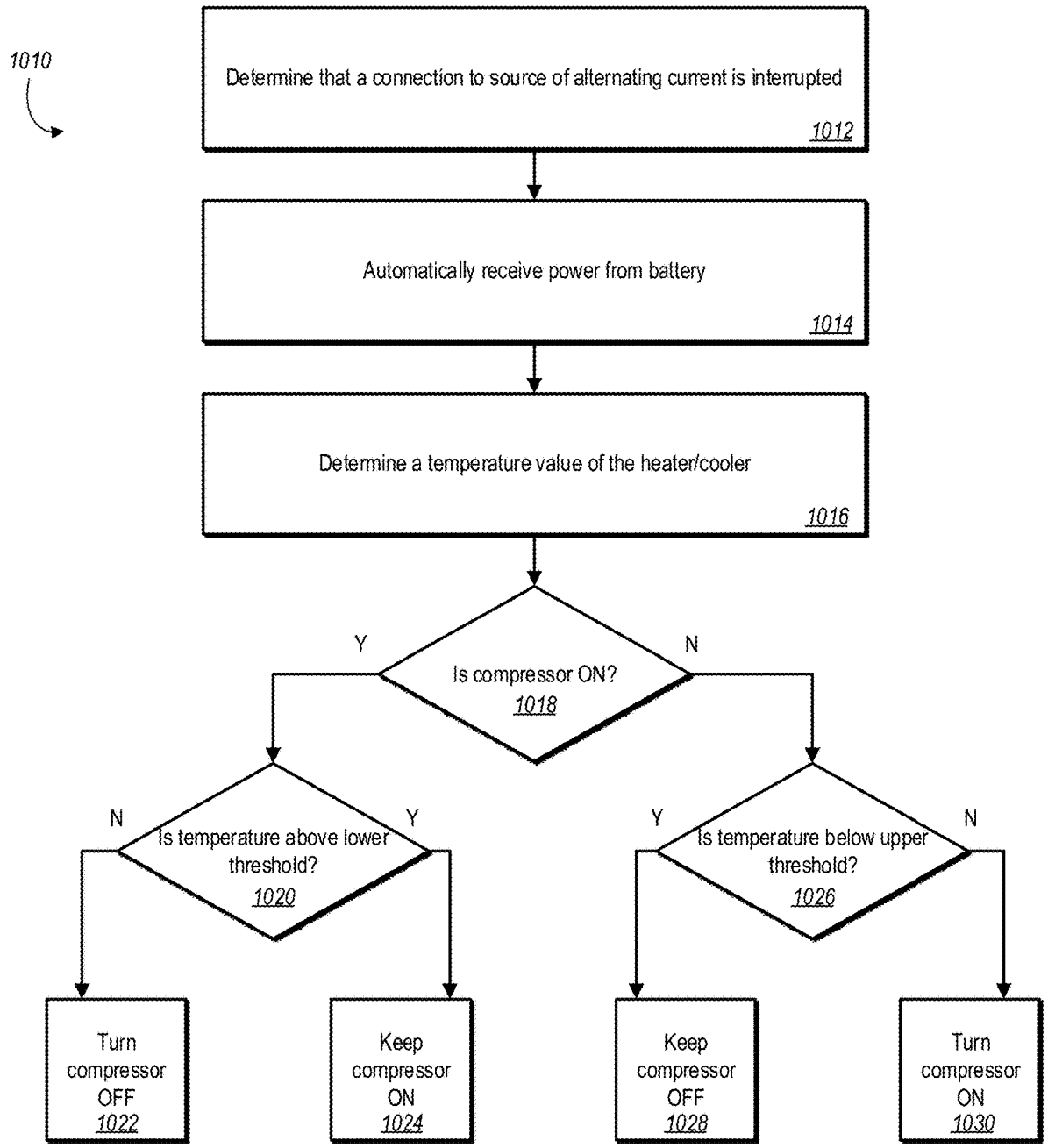
FIGS. 25-26 are flow chart diagrams of example processes for operation of the control console in a low power mode.
Figure 26:
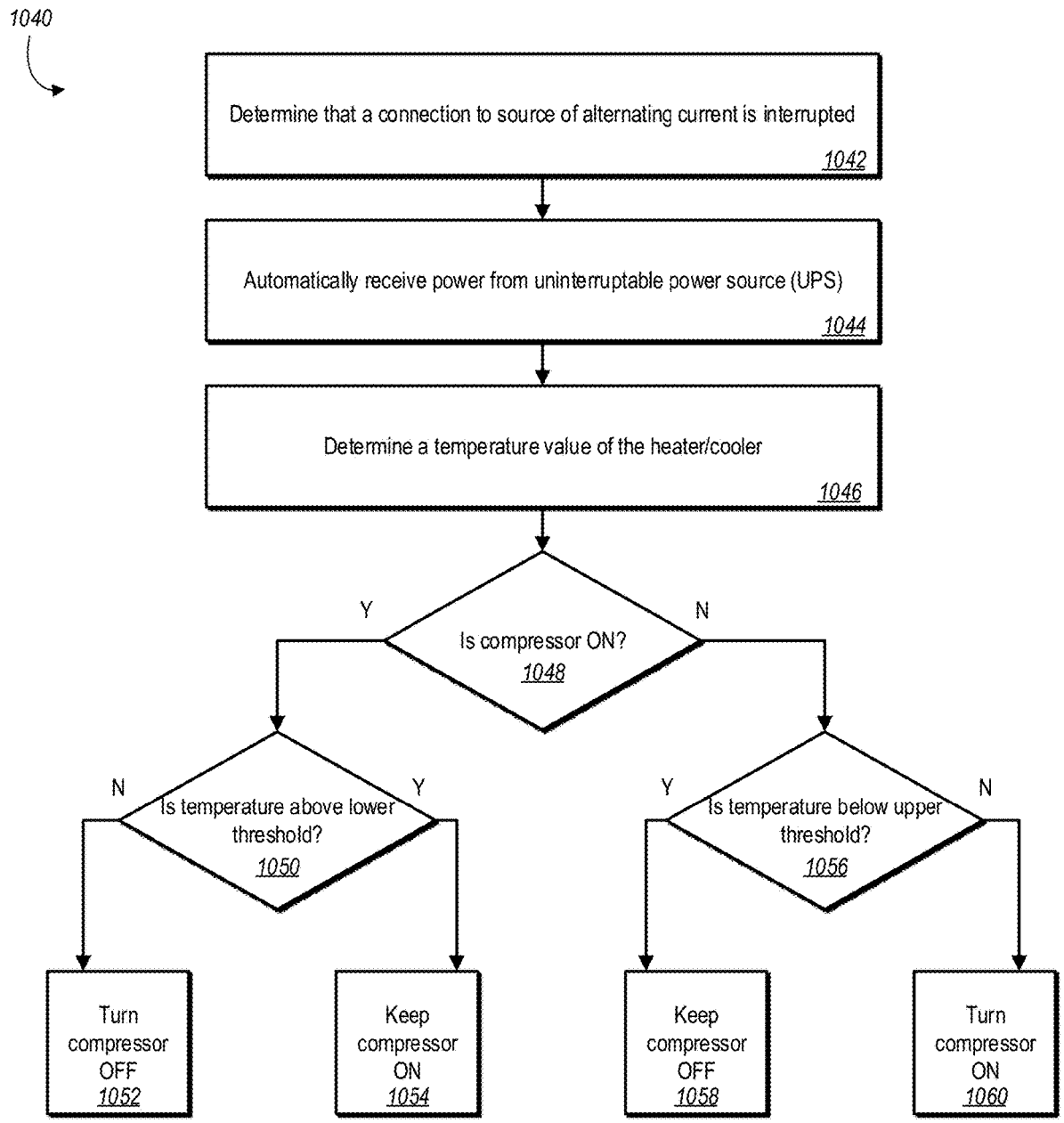

FIGS. 25-26 are flow chart diagrams of example processes for operation of the heat exchange system in a low power mode. Turning to FIG. 25, process 1010 shows a heat exchange system (e.g., heat exchange system 10 or 1000 described previously) configured to cause the heater/cooler to operate in a low-power mode in response to determining that a connection to an external supply of alternating current is interrupted. In an example, a portable system for managing the temperature of a patient during transport includes the heater/cooler configured to be in fluid communication with a heat transfer catheter configured for insertion into a patient or a heat transfer surface pad. The control console of the heat exchange system includes a processor configured to control operation of the heater/cooler. The alternating current power supply is configured to provide direct current to the control console and the heater/cooler. The alternating current power supply is configured to receive power from the source of alternating current. The alternating current power supply is configured to provide a low-power signal to the processor indicating that a connection to the source of alternating current is interrupted. The processor is configured to cause the heater/cooler to operate in a low-power mode in response to receiving the low-power signal from the alternating current power supply. The processor, in response to receiving the low power signal, determines (1012), that the connection to the external power supply is interrupted. The processor automatically switches to receive (1014) power from a battery, e.g., one or more transportable rechargeable batteries as described herein or other batteries or rechargeable batteries. The processor causes the heater/cooler to operate in a low-power mode. To do this, the processor causes a compressor of the heater/cooler to cycle between an ON state and an OFF state. To cycle the compressor, the processor is configured to determine (1016) a temperature value associated with the heater/cooler. For example, the temperature can be a temperature of cooling plates in the heater/cooler. The processor determines (1018) whether the compressor is ON or OFF. If the compressor is ON, the processor determines (1020) whether the temperature is above a lower temperature threshold. As previously described, the lower temperature threshold corresponds to a low cutoff temperature for maintaining a patient at a hypothermic state. The lower temperature threshold can be a static value, be a function of patient physiological parameters and/or the desired target temperature of the patient, and/or be a function of operating parameters of the heater/cooler, such as a size of the cold plates, a compressor speed, and so forth. If the temperature is above the lower threshold, the compressor is kept ON (1024). If the temperature is below the lower threshold, the patient is getting too cold, and the compressor is turned OFF (1022).

Similarly, if the compressor is OFF, the processor checks the temperature and compares (1026) the temperature to the upper threshold temperature. The upper threshold temperature can be determined in a similar manner as the lower threshold temperature. For example, the upper threshold temperature can be a static value, be a function of patient physiological parameters and/or the desired target temperature of the patient, and/or be a function of operating parameters of the heater/cooler, such as a size of the cold plates, a compressor speed, and so forth. If the temperature is below the upper threshold, the patient is still being maintained at an acceptable hypothermic state, and the compressor can be kept OFF (1028). If the temperature is not below the upper threshold, the patient is getting too warm, and the compressor is turned ON (1030). In some implementations, the lower temperature threshold for the plates is approximately 5 degrees C. for maintaining a patient at 32 degrees C. In some implementations, the upper temperature threshold for the plates is approximately 16 degrees C. for maintaining a patient at 32 degrees C. While cold plate temperature values are used for setting thresholds in this example, other temperature values (such as a temperature value read from a temperature sensor) can be used to set the threshold. The exact values of those thresholds can also vary based on the particular physical parameters of the heat exchange system 10.

Turning to FIG. 26, process 1040 shows an example of heat exchange system (e.g., heat exchange system 10 or 1000 described previously) configured to cause the heater/cooler to operate in a low-power mode in response to determining that a connection to an external supply of alternating current is interrupted. In an example, a portable system for managing the temperature of a patient during transport includes the heater/cooler configured to be in fluid communication with a heat transfer catheter configured for insertion into a patient or a heat transfer surface pad. The control console of the heat exchange system includes a processor configured to control operation of the heater/cooler. The alternating current power supply is configured to provide power to the control console and the heater/cooler. The alternating current power supply is configured to receive power from an uninterruptable power supply (UPS). The UPS is configured to provide a low-power signal to the processor indicating that a connection to the source of alternating current is interrupted. The processor is configured to cause the heater/cooler to operate in a low-power mode in response to receiving the low-power signal from the UPS. The processor, in response to receiving the low power signal, determines (1012), that the connection to the source of alternating current is interrupted. The UPS automatically switches to providing power from a battery of the UPS. The battery of the UPS can also supplement the power from the source of alternating current when the source is not enough for the load of the system. The processor, in response to receiving the low-power signal from the UPS, causes the heater/cooler to operate in a low-power mode. To do this, the processor causes a compressor of the heater/cooler to cycle between an ON state and an OFF state. To cycle the compressor, the processor is configured to determine (1046) a temperature value associated with the heater/cooler. For example, the temperature can be a temperature of cooling plates in the heater/cooler. The processor determines (10484) whether the compressor is ON or OFF. If the compressor is ON, the processor determines (1050) whether the temperature is above a lower temperature threshold. As previously described, the lower temperature threshold corresponds to a low cutoff temperature for maintaining a patient at a hypothermic state. The lower temperature threshold can be a static value, be a function of patient physiological parameters and/or the desired target temperature of the patient, and/or be a function of operating parameters of the heater/cooler, such as a size of the cold plates, a compressor speed, and so forth. If the temperature is above the lower threshold, the compressor is kept ON (1054). If the temperature is below the lower threshold, the patient is getting too cold, and the compressor is turned OFF (1052).

Similarly, if the compressor is OFF, the processor checks the temperature and compares (1056) the temperature to the upper threshold temperature. The upper threshold temperature can be determined in a similar manner as the lower threshold temperature. For example, the upper threshold temperature can be a static value, be a function of patient physiological parameters and/or the desired target temperature of the patient, and/or be a function of operating parameters of the heater/cooler, such as a size of the cold plates, a compressor speed, and so forth. If the temperature is below the upper threshold, the patient is still being maintained at an acceptable hypothermic state, and the compressor can be kept OFF (1058). If the temperature is not below the upper threshold, the patient is getting too warm, and the compressor is turned ON (1060). In some implementations, the lower temperature threshold for the plates is approximately 5 degrees C. for maintaining a patient at 32 degrees C. In some implementations, the upper temperature threshold for the plates is approximately 16 degrees C. for maintaining a patient at 32 degrees C. While cold plate temperature values are used for setting thresholds in this example, other temperature values (such as a temperature value read from a temperature sensor) can be used to set the threshold. The exact values of those thresholds can also vary based on the particular physical parameters of the heat exchange system 10.

Although the disclosed heat exchange system has been described above with reference to certain examples or embodiments, various additions, deletions, alterations and modifications may be made to those described examples and embodiments without departing from the intended spirit and scope of the disclosed heat exchange system. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any embodiment or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims. The disclosure is limited only by the scope of the appended claims.

What is claimed is:

1. A portable system for managing the temperature of a patient during transport, comprising:
a heater/cooler configured to be in fluid communication with a heat transfer surface pad or a heat transfer catheter configured for insertion into a patient;
a refrigeration circuit having a compressor configured to cool a heat exchange fluid circulating between the heater/cooler and the heat transfer surface pad or heat transfer catheter;
a pump for circulating heat exchange fluid between the heater/cooler and the heat transfer catheter or surface pad;
an alternating current power supply configured to provide power to the system when the alternating power supply is connected to a source of alternating current;
a processor configured to monitor the alternating current power supply and to cause an indication to be displayed on an indicator on a console if the alternating current power supply connection to the source of alternating current is interrupted;
wherein the system is configured to be connected to at least one rechargeable battery, the at least one rechargeable battery configured to provide power to the system when the alternating power supply is not connected to a source of alternating current;
wherein the at least one rechargeable battery is capable of powering the system such that the system can deliver at least 50 watts of cooling power;
wherein if the system is powered on and wherein the connection to the alternating current source is interrupted, the system automatically switches to receiving power from the at least one rechargeable battery;
wherein the processor, responsive to the interruption of the connection to the alternating current source, transmits a signal to the indicator to alert an operator of the system to the interruption of the connection to the alternating current source and also provides an indication to the operator of the amount of energy remaining in the at least one rechargeable battery,
wherein the alternating current power supply has a direct current output used to charge the at least one rechargeable battery, wherein the processor monitors a current draw on the direct current output, the processor adjusting the current to charge the battery in accordance with the power needs of the console so as to limit the current draw from the direct current output to the battery, and
wherein when the alternating current power supply connection to the source of alternating current is interrupted, the processor adjusts the speed of the compressor of the refrigeration circuit, while maintaining an operation of the pump for circulating heat exchange fluid between the heater/cooler and the heat transfer surface pad or heat transfer catheter.

2. The system of claim 1, wherein the at least one rechargeable battery provides 90-100 Watt-hours.

3. The system of claim 1, wherein the at least one rechargeable battery is capable of powering the system such that the system can deliver at least 150 watts of cooling power for at least 10 minutes.

4. The system of claim 3, wherein the at least one rechargeable battery is capable of powering the system such that the system can deliver 150-700 watts of cooling power for 10-90 minutes.

5. The system of claim 4, wherein the at least one rechargeable battery is capable of powering the system such that the system can deliver 600-700 watts of cooling power for at least 10 minutes.

6. The system of claim 1, wherein when the alternating current power supply is connected to the alternating current power source, the processor controls the alternating current power supply to provide power to the system to operate the system and also to provide power to charge the at least one rechargeable battery.

7. The system of claim 1, further comprising a portable housing and a battery pack, wherein the at least one rechargeable battery is mounted in the battery pack, and the battery pack is mounted to the portable housing.

8. The system of claim 1, wherein the system automatically switches from the alternating current supply to the battery to provide power to the system without interruption.

9. The system of claim 1, wherein the processor, responsive to the interruption of a connection with the alternating current source, controls the compressor to a low speed and to monitors a current draw by the system, and monitors an amount of stored energy in each of the at least one batteries and provides an indication of the amount of energy remaining in each of the at least one batteries to be displayed individually on the console to the operator.

10. The system of claim 6, further comprising a main power switch, the main power switch configured to provide power to the console when the main power switch is in a power on state, and to interrupt power to the console when the main power switch is in a power off state.

11. The system of claim 10, wherein if the alternating current supply is connected to the alternating current source, and the main power switch is in the power off state, the alternating current source provides power to a charging circuit to charge the at least one rechargeable battery.

12. The system of claim 1, wherein the direct current output of the alternating current power supply is a 24 volt direct current output, the 24 volt direct current output being used to power the console and to charge the at least one rechargeable battery, and wherein the processor monitors a current draw on the 24 volt direct current output, the processor adjusting the current to charge the battery in accordance with the power needs of the console so as to limit the current draw from the 24 voltage direct current output to 10 amps.

13. The system of claim 1, wherein the processor adjusts the current available for charging the at least one rechargeable battery at least once a second.

14. The system of claim 1, wherein the processor adjusts the current available for charging the at least one rechargeable battery at a periodic time interval, the periodic time interval being in a range of 0.1 to 10.0 seconds.

15. The system of claim 1, wherein the processor is operably connected to the at least one rechargeable battery via a communication bus, the communication bus having a connector for the at least one rechargeable battery, the connector configured to engage a connector disposed on the at least one rechargeable battery.

16. The system of claim 1, wherein the processor is configured to cause the heater/cooler to operate in a low-power mode when the alternating current power supply connection to the source of alternating current is interrupted.

17. The system of claim 16, further comprising a compressor connected to the heater/cooler, the compressor configured to cool the heater/cooler, wherein causing the heater/cooler to operate in a low-power mode comprises causing the compressor to cycle between an ON state and an OFF state.

18. The system of claim 17, wherein the processor is configured to monitor a temperature of the heater/cooler;
   wherein the processor is configured to cycle the compressor to the ON state when the temperature exceeds an upper threshold and until the temperature is below a lower threshold; and
   wherein the processor is configured to cycle the compressor to the OFF state when the temperature is below the lower threshold and until the temperature exceeds the upper threshold.

19. The system of claim 1, further comprising an uninterruptable power supply (UPS), wherein automatically switching to receiving power from the at least one rechargeable battery comprises:
   automatically supplying power from a battery of the UPS when the alternating current source is interrupted or is insufficient for a load of the system; and
   wherein the processor is configured to receive signal sent by the UPS indicating that the UPS is supplying power from the battery; and
   wherein the processor is configured to cause the heater/cooler to operate in a low-power mode in response to receiving the signal.

* * * * *

UNITED STATES PATENT AND TRADEMARK OFFICE
CERTIFICATE OF CORRECTION

| | | |
|---|---|---|
| PATENT NO. | : 11,865,035 B2 | Page 1 of 1 |
| APPLICATION NO. | : 16/835232 | |
| DATED | : January 9, 2024 | |
| INVENTOR(S) | : Dabrowiak et al. | |

It is certified that error appears in the above-identified patent and that said Letters Patent is hereby corrected as shown below:

In the Drawings

Figure 13:
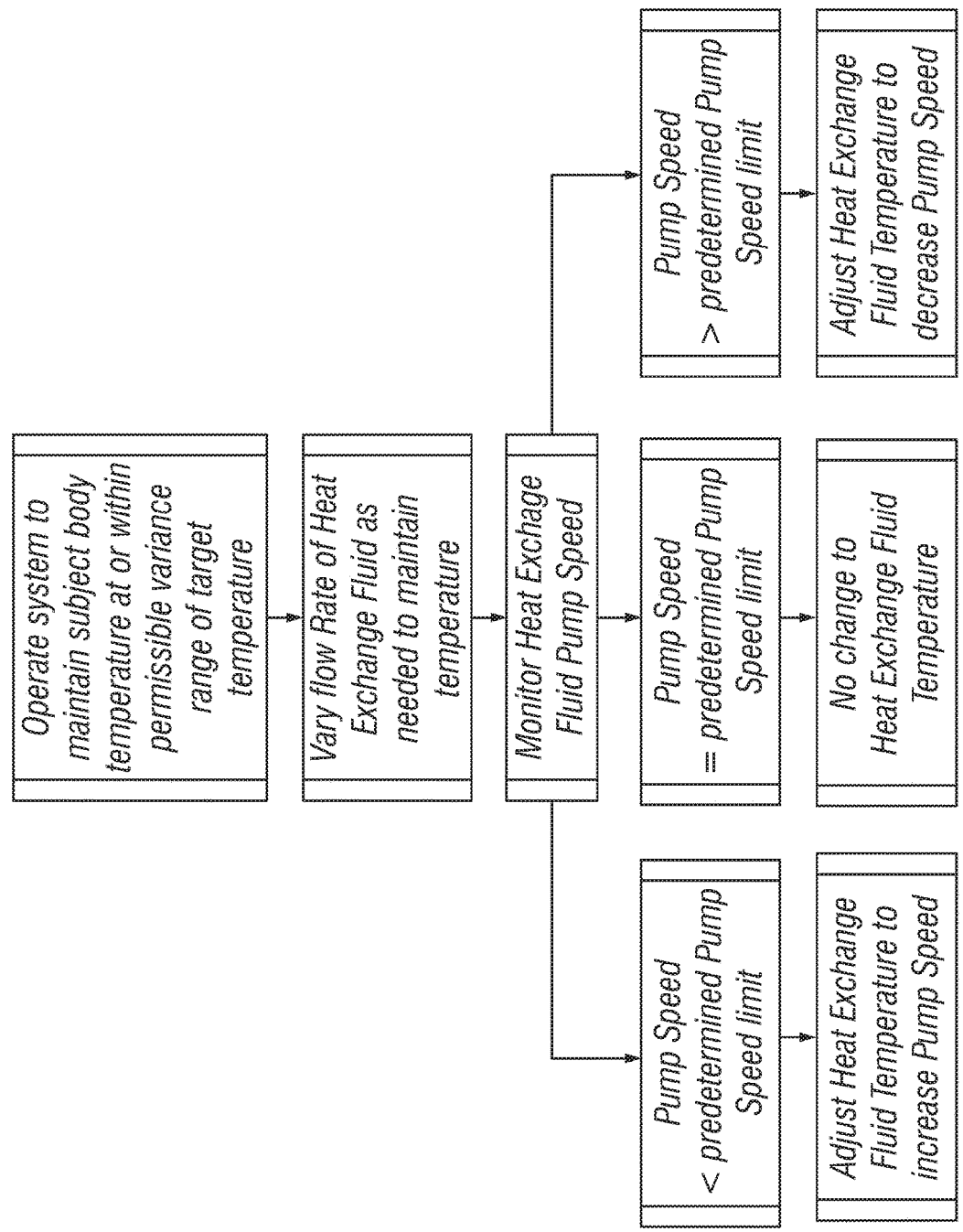
FIG. 13 is a flow diagram showing one example of a process by which a body heat exchange system may combine variations in heat exchange fluid flow rate with variations in heat exchange fluid temperature for precise maintenance of a target body temperature.

Sheet 19 of 32, FIG. 13, Line 11, delete "Exchage" and insert -- Exchange --.

Sheet 28 of 32, FIG. 22, y axis, delete "PREOCESSOR" and insert -- PROCESSOR --.

Sheet 29 of 32, (Reference Numeral 900) FIG. 23, delete "NEEDDS" and insert -- NEEDS --.

In the Specification

Column 6, Line 47, delete "in in" and insert -- in --.

Column 7, Line 17, delete "batteries" and insert -- batteries. --.

Column 17, Line 16, delete "TECHOMETER" and insert -- TACHOMETER --.

Column 19, Line 30, delete "MM." and insert -- MRI. --.

Column 21, Line 66, delete "that that" and insert -- that --.

Column 31, Line 12, delete "the a" and insert -- the --.

Column 31, Line 46, delete "patient," and insert -- patient. --.

Column 31, Line 53, delete "that that" and insert -- that --.

Signed and Sealed this
Twenty-ninth Day of October, 2024

Katherine Kelly Vidal
*Director of the United States Patent and Trademark Office*